(12) United States Patent
Teng et al.

(10) Patent No.: US 11,547,099 B2
(45) Date of Patent: Jan. 10, 2023

(54) TRANSGENIC MICE

(71) Applicant: Crescendo Biologies Limited, Cambridge (GB)

(72) Inventors: Yumin Teng, Cambridge (GB); Joyce Young, Cambridge (GB); Brian McGuinness, Cambridge (GB); Mike Romanos, Cambridge (GB); Marianne Brueggemann, Foxton (GB)

(73) Assignee: Crescendo Biologies Limited, Cambridge (GB)

( * ) Notice: Subject to any disclaimer, the term of this patent is extended or adjusted under 35 U.S.C. 154(b) by 86 days.

(21) Appl. No.: 15/520,627

(22) PCT Filed: Oct. 22, 2014

(86) PCT No.: PCT/GB2014/053146
§ 371 (c)(1),
(2) Date: Apr. 20, 2017

(87) PCT Pub. No.: WO2016/062990
PCT Pub. Date: Apr. 28, 2016

(65) Prior Publication Data
US 2018/0362666 A1    Dec. 20, 2018

(51) Int. Cl.
*A01K 67/00* (2006.01)
*A01K 67/027* (2006.01)
*C12N 15/85* (2006.01)
*C07K 16/00* (2006.01)
*C07K 16/46* (2006.01)

(52) U.S. Cl.
CPC ...... *A01K 67/0275* (2013.01); *A01K 67/0278* (2013.01); *C07K 16/00* (2013.01); *C07K 16/46* (2013.01); *C12N 15/8509* (2013.01); *A01K 2217/05* (2013.01); *A01K 2217/052* (2013.01); *A01K 2217/07* (2013.01); *A01K 2217/072* (2013.01); *A01K 2217/075* (2013.01); *A01K 2217/15* (2013.01); *A01K 2227/105* (2013.01); *A01K 2267/01* (2013.01); *C07K 2317/569* (2013.01); *C07K 2317/92* (2013.01); *C12N 2015/8518* (2013.01); *C12N 2800/206* (2013.01); *C12N 2830/30* (2013.01)

(58) Field of Classification Search
CPC ............ A01K 67/0276; A01K 67/0275; A01K 67/0278; A01K 2217/05; A01K 2217/07; A01K 2217/15; A01K 2227/105
See application file for complete search history.

(56) References Cited

U.S. PATENT DOCUMENTS

2014/0283150 A1    9/2014 Bradley et al.
2015/0133641 A1*   5/2015 Germaschewski .... C07K 16/00
                                                    530/387.3

FOREIGN PATENT DOCUMENTS

| GB | 2398784 A1 * | 9/2004 | .......... A61K 67/027 |
|----|---|---|---|
| GB | 2495083 A | 4/2013 | |
| GB | 2502127 A | 11/2013 | |
| JP | 2003-501103 A | 1/2003 | |
| WO | WO 2000/076310 A1 | 12/2000 | |
| WO | WO 2011/072204 A | 6/2011 | |
| WO | WO 2013/045916 A1 | 4/2013 | |
| WO | WO 2014/093908 A2 | 6/2014 | |
| WO | WO 2014/141192 A1 | 9/2014 | |
| WO | WO 2015/143414 | 9/2015 | |

OTHER PUBLICATIONS

Naito et al. J Reprod Fert 113:137-143, 1998 (Year: 1998).*
Raina etall. Gene 96-100, 2015 (Year: 2015).*
Ollo et al. PNAS 78(4):2442-2446, 1981 (Year: 1981).*
Dolatshad et al. Mammalian Genome 26:598-608, 2015 (Year: 2015).*
Yin et al. Genetics and Molecular Research 11 (1):355-369, 2012 (Year: 2012).*
Janssens et al., Generation of heavy-chain-only antibodies in mice. Proc Natl Acad Sci USA. Oct. 10, 2006;103(41):15130-5. Epub Oct. 2, 2006.
Murphy, VelocImmune: Immunoglobulin Variable Region Humanized Mice. In: Recombinant Antibodies for Immunotherapy. 2009. Chapter 8, pp. 100-107. Cambridge University Press. Ed: Little.
Third Party Observations under Article 115 EPC for European Application 14790686.1 dated Apr. 13, 2018.
Grounds for opposition. Filed in EP Patent 3209698 opposition proceedings on Jun. 5, 2019 as "D10" by Opponent Regeneron Pharmaceuticals. 41 pages.
Garrett et al., Chromatin architecture near a potential 3' end of the IgH locus involves modular regulation of histone modifications during B-Cell development and in vivo occupancy at CTCF sites. Mol Cell Biol. Feb. 2005;25(4): 1511-25.
Gillies et al., A tissue-specific transcription enhancer element is located in the major intron of a rearranged immunoglobulin heavy chain gene. Cell. Jul. 1983;33(3):717-28.
Ma et al., Human antibody expression in transgenic rats: comparison of chimeric IgH loci with human VH, D and JH but bearing different rat C-gene regions. J Immunol Methods. Dec. 31, 2013;400-401:78-86. doi: 10.1016/j.jim.2013.10.007. Epub Oct. 30, 2013.

(Continued)

*Primary Examiner* — Marcia S Noble

(74) *Attorney, Agent, or Firm* — Wolf, Greenfield & Sacks, P.C.

(57) ABSTRACT

The invention relates to nucleic acid constructs for expression in mice for the production of heavy chain only antibodies and $V_H$ domains, transgenic mice, related methods and uses.

11 Claims, 33 Drawing Sheets

Specification includes a Sequence Listing.

(56) References Cited

OTHER PUBLICATIONS

Macdonald et al., Precise and in situ genetic humanization of 6 Mb of mouse immunoglobulin genes. Proc Natl Acad Sci USA. Apr. 8, 2014;111(14):5147-52. doi: 10.1073/pnas.1323896111. Epub Mar. 25, 2014.

Mendez et al., Functional transplant of megabase human immunoglobulin loci recapitulates human antibody response in mice. Nat Genet. Feb. 1997;15(2):146-56. Erratum in: Nat Genet Aug. 1997;16(4):410.

Genbank Accession No. V10523. Dec. 6, 2013. Gillies et al. 1 page.

Genbank Accession No. AF446347.1. Feb. 14, 2002. Schrader et al. 1 page.

Murphy et al., Janeway's Immunobiology. Seventh edition. Chapter 4. 2008; pp. 171-175.

Schrader et al., Role for mismatch repair proteins Msh2, M1h1, and Pms2 in immunoglobulin class switching shown by sequence analysis of recombination junctions. J Exp Med. Feb. 4, 2002;195(3):367-73.

Figure 7:
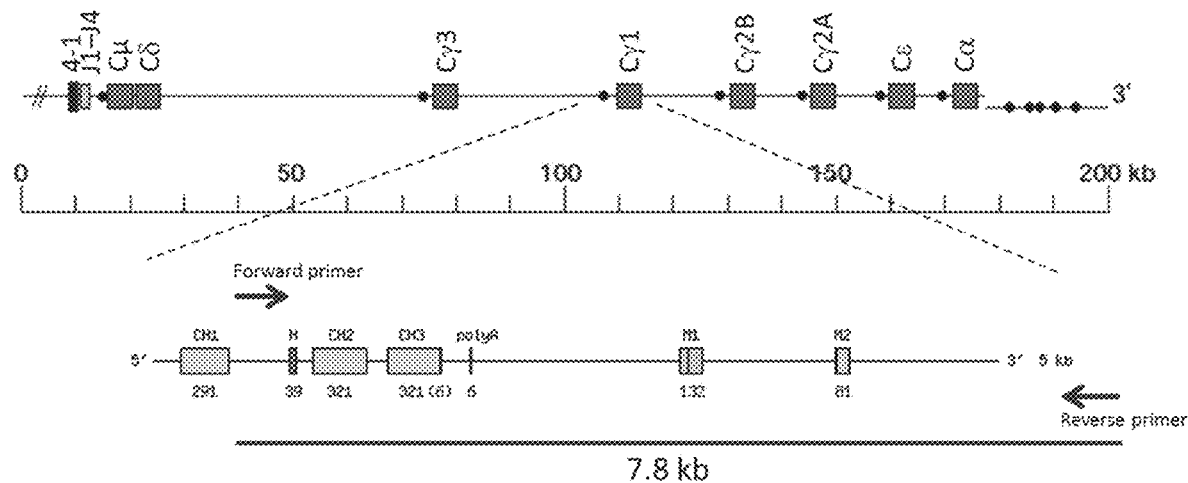

Sequence alignment of mouse μ enhancer database sequence with sequences from Figure 7 of D6. Filed in EP Patent 3209698 opposition proceedings on Jun. 5, 2019 as "D7" by Opponent Regeneron Pharmaceuticals. 2 pages.

Sequence alignment of mouse μ switch region database sequence with sequences from Figure 7 of D6. Filed in EP Patent 3209698 opposition proceedings on Jun. 5, 2019 as "D10" by Opponent Regeneron Pharmaceuticals. 2 pages.

[No Author Listed] Response to Opposition to EP3209698B1 in the name of Crescendo Biologies, Inc. Apr. 11, 2019. 33 pages.

Arif, Takeda adds a $790M discovery deal to an ongoing R&D overhaul. Takeda Pharmaceuticals Press Release. Oct. 10, 2016. Retrieved from https://www.takeda.com/newsroom/newsreleases/2016/Crescendo-Biologics-and-Takeda-Enter-Collaboration-for-Humabody-based-Therapeutics. 1 page.

Johnston et al., The crescendo mouse drug discovery platform: a transgenic mouse generating high affinity fully human antibody fragments for therapeutic use. Transgenic Res. Oct. 2014;23(5):891.

Matsuda et al., The complete nucleotide sequence of the human immunoglobulin heavy chain variable region locus. J Exp Med. Dec. 7, 1998;188(11):2151-62.

Figure 1:
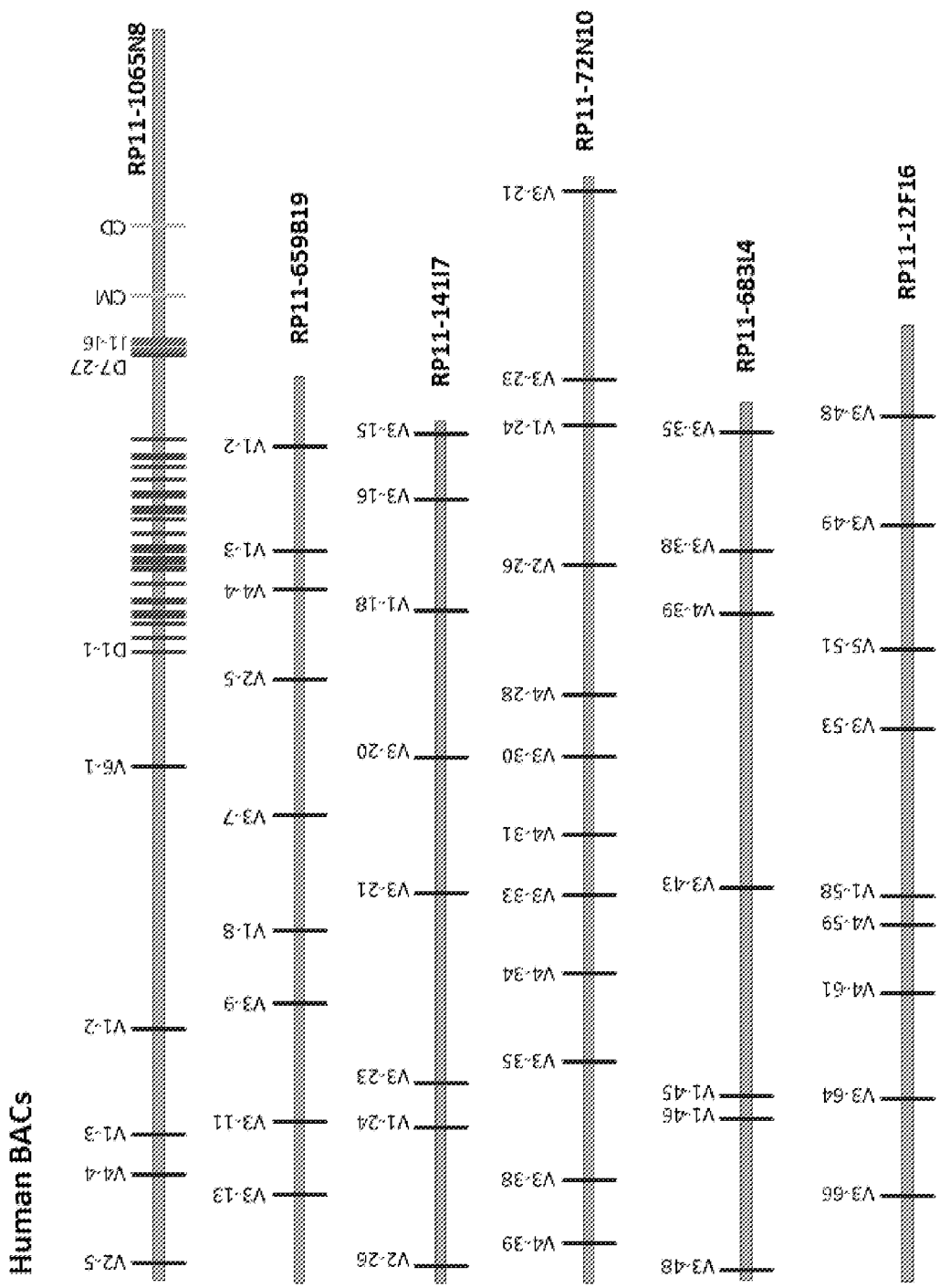

Matsuda et al., Annotated Figure 1 from The complete nucleotide sequence of the human immunoglobulin heavy chain variable region locus. J Exp Med. Dec. 7, 1998;188(11):Figure 1. 2 pages. Submitted in response to Opposition to EP3209698B1.

Matsuda et al., Figure VH61-VHs-11 showing the alignment of D6 V18 vector and genomic locus to scale from The complete nucleotide sequence of the human immunoglobulin heavy chain variable region locus. J Exp Med. Dec. 7, 1998;188(11):Figure Vh6-1-VHS-11. 1 page. Submitted in response to Opposition to EP3209698B1.

Osborn et al., High-affinity IgG antibodies develop naturally in Ig-knockout rats carrying germline human IgH/Igκ/Igλ loci bearing the rat CH region. J Immunol. Feb. 15, 2013;190(4):1481-90. doi: 10.4049/jimmunol.1203041. Epub Jan. 9, 2013. Erratum in: J Immunol. Jun. 15, 2013;190(12):6707.

Lu et al., Research Progress in the Theory and Technology of Transgenic Animals. Biotechnol. Bull. Dec. 31, 1997; 4: 19-26.

CN 201480082416.0, Mar. 4, 2020, English Translation of First Office Action.

\* cited by examiner

BAC cargo introduced by homologous recombination

- ⊢ YAC arm
- ▲ Floxed selectable marker
- ▬ sequence introduced on YAC
- ┈ sequence introduced on BAC b cont.

b.

a.

b c.

Post-selection ELISA

|   | 1 | 2 | 3 | 4 | 5 | 6 | 7 | 8 | 9 | 10 | 11 | 12 |
|---|---|---|---|---|---|---|---|---|---|---|---|---|
| A |   |   | 0.704 | 0.064 | 0.131 | 0.122 |   |   | 0.102 | 0.113 | 0.169 |   |
| B |   | 0.94 |   | 0.126 | 0.088 |   |   | 0.126 | 0.115 | 0.078 |   | 0.379 |
| C | 0.43 | 0.095 | 0.117 |   |   |   |   | 0.104 | 0.058 | 0.241 | 0.057 |
| D |   |   | 0.051 |   |   |   |   | 0.053 | 0.057 |   |   | 0.12 |
| E | 0.702 | 0.284 |   |   | 0.084 | 0.207 |   |   | 0.658 |   |   |   |
| F |   | 0.046 |   |   |   |   | 0.578 |   |   |   |   |   |
| G | 0.127 |   | 0.372 | 0.033 |   | 0.062 |   | 0.084 | 0.062 | 0.05 |   | 0.037 |
| H |   |   | 0.095 |   |   |   | 0.124 |   |   |   | 0.053 | 0.109 |

+ve (rows A–F)
-ve (rows G–H)

Pre-Selection Library

|   | 1 | 2 | 3 | 4 | 5 | 6 | 7 | 8 | 9 | 10 | 11 | 12 |
|---|---|---|---|---|---|---|---|---|---|---|---|---|
| A | 0.065 | 0.061 | 0.059 | 0.053 | 0.064 | 0.053 | 0.087 | 0.052 | 0.057 | 0.063 | 0.057 | 0.065 |
| B | 0.075 | 0.071 | 0.072 | 0.078 | 0.098 | 0.102 | 0.081 | 0.072 | 0.078 | 0.082 |  | 0.083 |
| C | 0.056 | 0.054 | 0.053 | 0.064 | 0.065 | 0.07 | 0.07 | 0.054 | 0.055 | 0.059 | 0.064 | 0.061 |
| D | 0.048 | 0.058 | 0.052 | 0.056 | 0.056 | 0.05 | 0.047 | 0.051 | 0.049 | 0.062 | 0.049 | 0.085 |
| E | 0.056 | 0.054 | 0.05 | 0.046 | 0.051 | 0.102 | 0.047 | 0.048 | 0.048 | 0.049 | 0.049 |  |
| F | 0.067 | 0.048 | 0.05 | 0.049 | 0.051 | 0.119 | 0.072 | 0.053 | 0.05 | 0.049 | 0.051 |  |
| G | 0.041 | 0.041 | 0.042 | 0.047 | 0.048 | 0.061 | 0.046 | 0.055 | 0.039 | 0.036 | 0.032 | 0.031 |
| H | 0.076 | 0.056 | 0.053 | 0.05 | 0.055 | 0.055 | 0.05 | 0.053 | 0.049 | 0.049 | 0.061 | 0.051 |

+ve (A–F), -ve (G–H)

After one round of Selection Library

|   | 1 | 2 | 3 | 4 | 5 | 6 | 7 | 8 | 9 | 10 | 11 | 12 |
|---|---|---|---|---|---|---|---|---|---|---|---|---|
| A | 0.349 | 0.136 | 0.133 |   | 0.185 | 0.225 | 0.169 | 0.312 | 0.169 | 0.175 | 0.158 | 0.296 |
| B |   | 0.261 |   | 0.238 | 0.338 | 0.188 | 0.239 |   | 0.53 | 0.09 | 0.357 |   |
| C | 0.208 | 0.248 | 0.066 | 0.173 | 0.086 | 0.208 | 0.324 | 0.075 | 0.166 | 0.244 | 0.053 | 0.12 |
| D | 0.115 |   | 0.226 | 0.219 | 0.07 | 0.272 | 0.361 | 0.334 | 0.084 | 0.328 | 0.153 |   |
| E |   |   | 0.111 | 0.504 | 0.119 | 0.28 | 0.067 | 0.221 | 0.153 | 0.436 | 0.056 |   |
| F | 0.122 |   |   | 0.085 | 0.377 | 0.351 |   | 0.136 | 0.129 | 0.056 |   |   |
| G | 0.337 | 0.173 |   | 0.146 |   |   | 0.075 | 0.244 | 0.052 | 0.066 | 0.193 | 0.04 |
| H |   | 0.174 | 0.146 |   | 0.088 | 0.183 | 0.191 | 0.182 | 0.101 | 0.122 |   | 0.153 |

+ve (A–F), -ve (G–H)

a.

c.

Figure 27 cont.

a.

b.

TRANSGENIC MICE

RELATED APPLICATION

This application is a national stage filing under 35 U.S.C. § 371 of International Application No. PCT/GB2014/053146, filed Oct. 22, 2014, the entire contents of which is incorporated by reference herein in its entirety.

FIELD OF THE INVENTION

The present invention relates to nucleic acid constructs for expression in mice. The invention also relates to the use of these constructs in producing heavy chain-only antibodies, for example produced in mice which are compromised in the expression of light chain (L-chain) and heavy chain (H-chain) loci. The invention also relates to the isolation and use of single $V_H$ domains derived from such heavy chain-only antibodies.

INTRODUCTION

Most natural antibodies or immunoglobulins (Ig's) typically comprise two heavy (H) chains and two light (L) chains. The H-chains are joined to each other by disulphide bonds located near a flexible hinge domain, and each H-chain has a L-chain disulphide bonded to its N-terminal region, to form an $H_2L_2$ heterotetramer. Each L-chain has a variable ($V_L$) and a constant ($C_L$) domain, while each H-chain comprises a variable domain ($V_H$), a first constant domain ($C_H1$), a hinge domain and two or three further constant domains ($C_H2$, $C_H3$ and optionally $C_H4$). In normal dimeric antibodies ($H_2L_2$) interaction of each $V_H$ and $V_L$ domain forms an antigen binding region (interaction between the $C_H1$ domain and the $C_L$ domain is also known to facilitate functional association between the heavy and light chains).

Several different classes of natural Ig are known. These classes (or isotypes) differ in the constant domains of their H-chains, which in turn affects the function of the Ig. In mammals, the five isotypes of Ig are IgA, IgD, IgE, IgG and IgM. IgA comprises $C_H$ domains encoded by $C_\alpha$ gene segments and plays a central role in mucosal immunity. Secretory IgA is dimeric, containing two $H_2L_2$ units joined by one J chain, and is generally abundant in secretions such as milk and colostrum. Serum IgA is present in humans as an $H_2L_2$ monomer. IgD comprises $C_H$ domains encoded by $C_\delta$ gene segments, is monomeric, and functions as an antigen receptor on B cells, the cells responsible for producing antibodies. IgE has $C_H$ domains encoded by $C_\epsilon$ gene segments, is also monomeric, and when bound to the high affinity Fcε receptors on mast cells can be cross-linked by allergen which triggers the release of cytokines and histamine (allergy response). IgG exists as four different subtypes in humans, all of which are monomeric and comprise $C_H$ domains encoded by $C_\gamma$ gene segments. The IgG isotype comprises the majority of a mature antibody-based (humoral) immune response. Finally, IgM has $C_H$ domains encoded by $C_\mu$ gene segments, and (similar to IgG, A and E) is expressed both on the surface of B cells and also in a secreted form. Secreted IgM is pentameric and plays a key role in eliminating pathogens as part of the early humoural response.

Normal Ig expression in B cells involves an ordered succession of gene rearrangements. Exons encoding the variable regions of H-chains are constructed in vivo by assembly of $V_H$, diversity (D) and joining ($J_H$) segments. Variable regions for L-chains are compiled in an equivalent process by assembly of $V_L$ and $J_L$ segments. The rearranged VDJ region is initially transcribed in association with the $C_\mu$ gene segments, leading to the synthesis of an IgM H-chain. Subsequently, in the periphery, switch recombination brings further downstream $C_H$ gene segments (δ, γ, α or ε) close to the VDJ exon resulting in Ig class switching. Maturation of B cells expressing H-chain Ig without L-chain is prevented by chaperone association of the H-chain in the endoplasmic reticulum. However, if $C_H1$ is missing from the H-chain, this control is removed and the H-chain can travel unhindered to the cell surface and be secreted. Indeed, we have previously shown that, quite unexpectedly $L^{-/-}$ ($\kappa^{-/-}\lambda^{-/-}$-deficient) mice produce diverse H chain—only antibodies in serum without any further genetic manipulation and they do so at a relatively low level as a result of spontaneous loss of the $C_H1$ exon from the H-chain transcripts.

In Tylopoda or camelids (dromedaries, camels and llamas), a major type of Ig, composed solely of paired heavy chains (heavy chain only antibodies, HCAb), is produced as part of the normal humoral immune response to antigen in addition to conventional $H_2L_2$ antibodies (Padlan, E. A. 1994, Mol. Immunol. 31:169-217). The developmental processes leading to HCAb expression in these animals are unknown, however, it is known that they use a specific class of $V_H$ ($V_{HH}$) and Cγ genes which result in a smaller than conventional heavy chain, lacking the $C_H1$ domain (removed by alternative splicing of the RNA transcript). Heavy chain antibodies are also present in some primitive fish; e.g. the new antigen receptor (NAR) in the nurse shark and the specialized heavy chain (COS5) in ratfish (Greenberg et al, 1996, Eur. J. Immunol. 26:1123-1129, Rast et al, 1998, Immunogenetics, 47:234-245). Again these heavy chain Igs lack the $C_H1$-type domain.

Conventional antibodies have long been considered a powerful tool based on their exquisite selectivity, specificity and potency for target antigens. Indeed, they are now well established as highly effective therapeutic agents with sales of $54bn in 2012 expected to continue to grow significantly in the coming years. However, there is increasing demand for exploiting the benefits of alternative formats and smaller fragments in order to derive the next generation of antibody-based therapeutic candidates.

$V_H$ or $V_{HH}$ fragments are the smallest portion of an immunoglobulin molecule that retain target specificity and potency and the most robust antibody fragments in terms of stability, solubility, ease of engineering and manufacture. This makes them highly attractive therapeutic agents with significant advantages in particular for the development of products for local and topical delivery, pure antagonists and bi- or multi-specifics. In particular, the potential for camelid $V_{HH}$ domains to be used as potential drug products has attracted a lot of attention. However, the fact that they do not have a human amino acid sequence is the one key feature which counts against camelid $V_{HH}$ domains being optimal drug candidates as they have potential to elicit an anti-drug antibody response when administered to humans (in particular where the disease indication requires chronic administration).

As a consequence there has been a great deal of interest in producing human $V_H$ (or $V_L$) domains as therapeutic candidates. It is well known that $V_H$ domains derived from conventional antibodies require a companion $V_L$ domain in the absence of which they are difficult to express, often insoluble and suffer loss of binding affinity and specificity to target antigen. As a consequence, isolated human $V_H$ (or $V_L$) domains derived from in vitro display libraries built using domains that have developed in the presence of a partner domain require significant engineering in order to enhance solubility and stability.

The present invention arises from the surprising finding (see examples below) that diverse HCAbs without $C_H1$ can be generated by expressing chimeric nucleic acid constructs which comprise at least 10 functional human and non-engineered V genes in their natural configuration in knock-out mice. The production of HCAbs in a mouse of the present invention which has a human or chimeric heavy chain locus integrated into its genome offers numerous advantages in the production of therapeutic agents. Such HCAbs antibodies comprise fully human $V_H$ domains, which have been matured in vivo in the absence of a partner $V_L$ domain. $V_H$ domains derived from such HCAbs are highly potent, soluble, stable and capable of being expressed at high level.

The prior art discloses the production of heavy chain-only antibodies in mice in which the immunoglobulin light chains have been functionally silenced and where H-chain transcripts naturally undergo spontaneous loss of the $C_H1$ exon (U.S. Ser. No. 12/455,913). The prior art also describes the production of HCAb using constructs comprising camelid $V_{HH}$ genes (see for example WO 2006/008548).

The present invention is aimed at providing improved constructs for the transformation of mice and the production of human $V_H$ domains.

SUMMARY OF THE INVENTION

In a first aspect, the invention relates to a vector comprising
a) at least 10 functional human heavy chain V genes wherein at least 10 functional human heavy chain V genes are in their natural configuration;
b) at least one human heavy chain D gene and at least one human heavy chain J gene;
c) a murine C region which lacks the $C_H1$ exon.

In one embodiment, the vector comprises a murine 3' enhancer region or gene. In one embodiment, said murine 3' enhancer region or gene is at least about 42 kb in size. In one embodiment, said murine 3' enhancer region comprises one or more enhancer element selected from enhancer elements hs3A, hs1.2, hs3B, hs4, hs5, hs6 and hs7. In one embodiment, said murine 3' enhancer region comprises enhancer elements hs3A, hs1.2, hs3B, hs4, hs5, hs6 and hs7.

The invention also relates to a murine host cell transformed with a vector of the invention. The invention further relates to a transgenic mouse comprising a vector or host cell according to the invention. Preferably, the mouse is a triple knockout mouse which does not produce any functional endogenous light or heavy chains.

In a further aspect, the invention relates to a heavy chain only antibody or $V_H$ domain produced in or obtainable from the transgenic mouse of the invention.

In yet a further aspect, the invention relates to a method for making a HCAb, fragment thereof or antibody derived therefrom comprising introducing and expressing a vector according to the invention in a mouse. For example, the fragment is a $V_H$ domain. In another aspect, the invention relates to a heavy chain only antibody comprising human $V_H$ regions and a murine constant region which lacks the $C_H1$ region. In another aspect, the invention relates to a $V_H$ domain obtained or obtainable by a method of the invention.

In another aspect, the invention relates to the use of a transgenic mouse of the invention in constructing a library, for example a naïve library.

In another aspect, the invention relates to a method for making a library, for example a naïve library, using a transgenic mouse of the invention.

In another aspect, the invention relates to a method for making a library comprising ex vivo immunisation of a transgenic mouse of the invention or ex vivo immunisation of tissue or cells of a transgenic mouse of the invention.

In a final aspect, the invention relates to a composition comprising a $V_H$ domain obtained or obtainable by a method of the invention. The composition comprises the $V_H$ domain alone or in combination with another $V_H$ domain, protein, or other molecule of therapeutic benefit.

FIGURES

The invention is further described in the following non-limiting figures.

Figure 2:
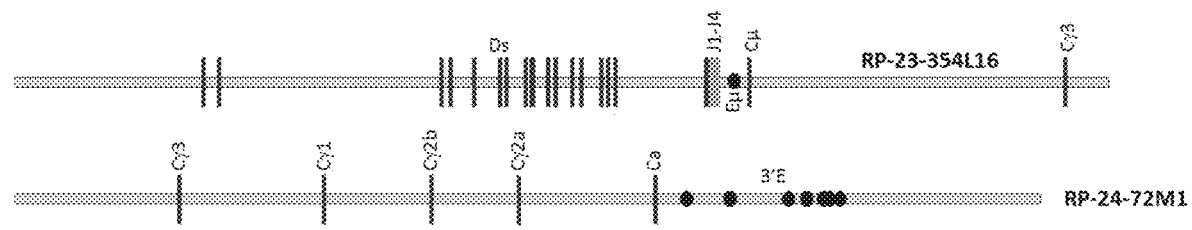
Figure 3:
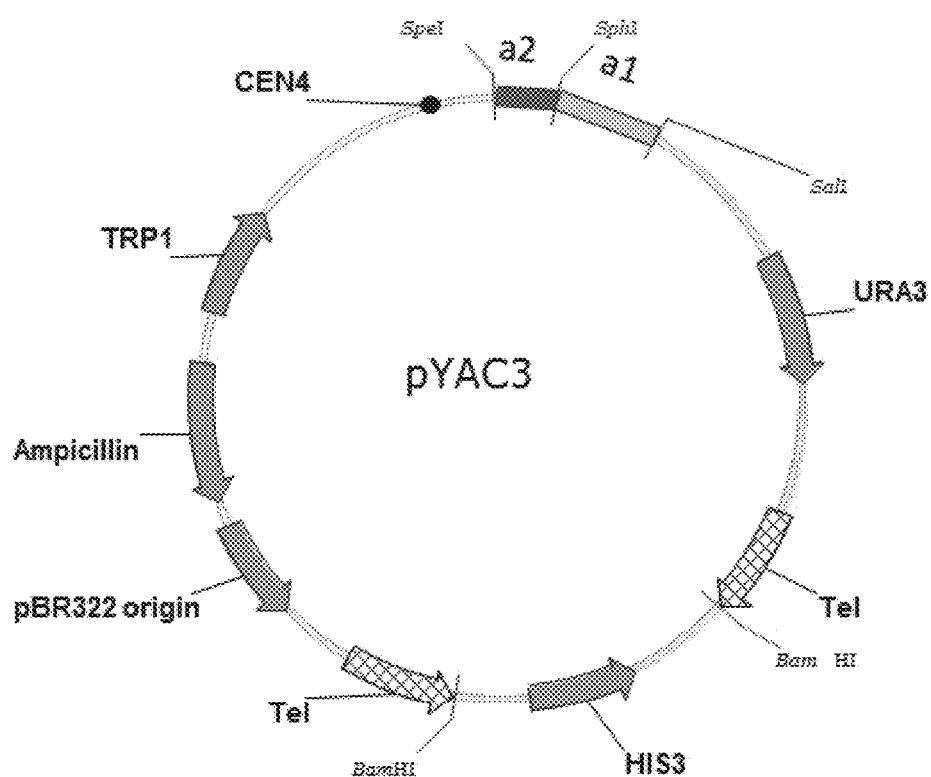
Figure 4:
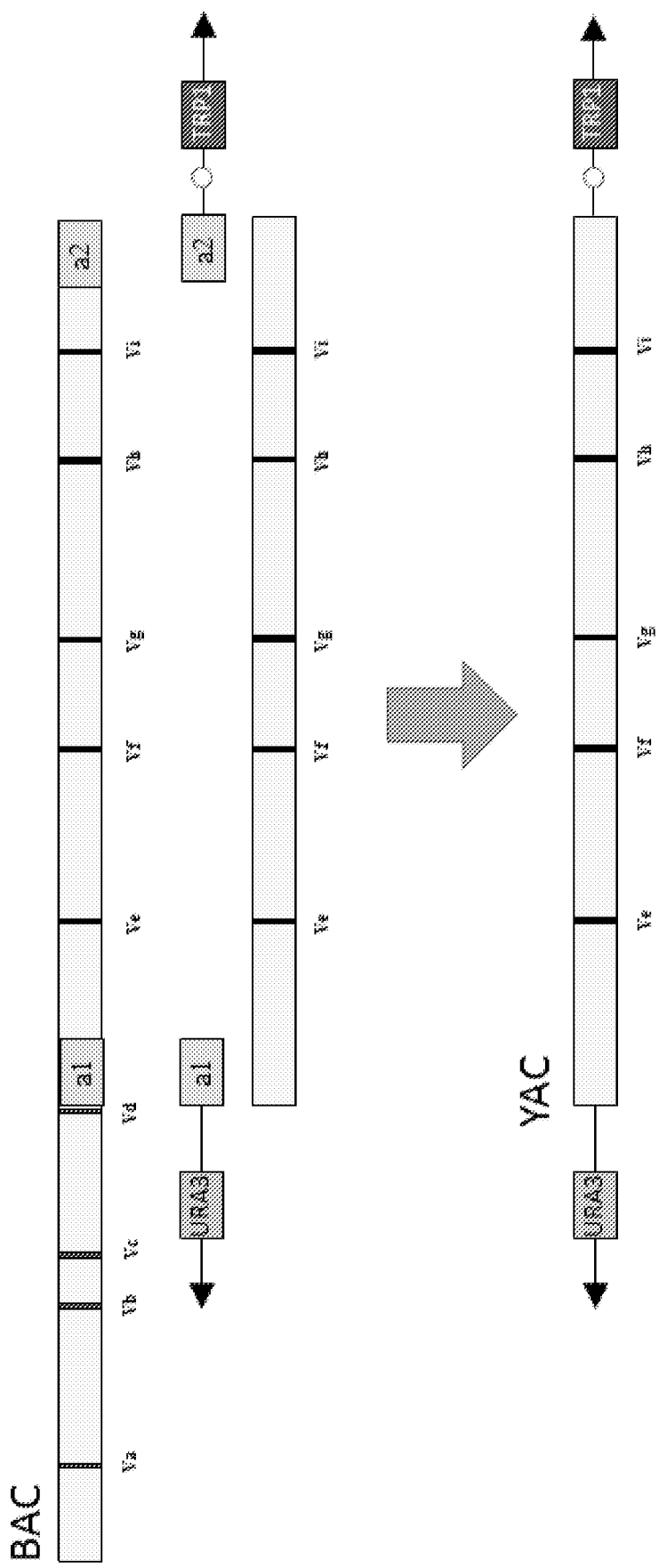
Figure 5:
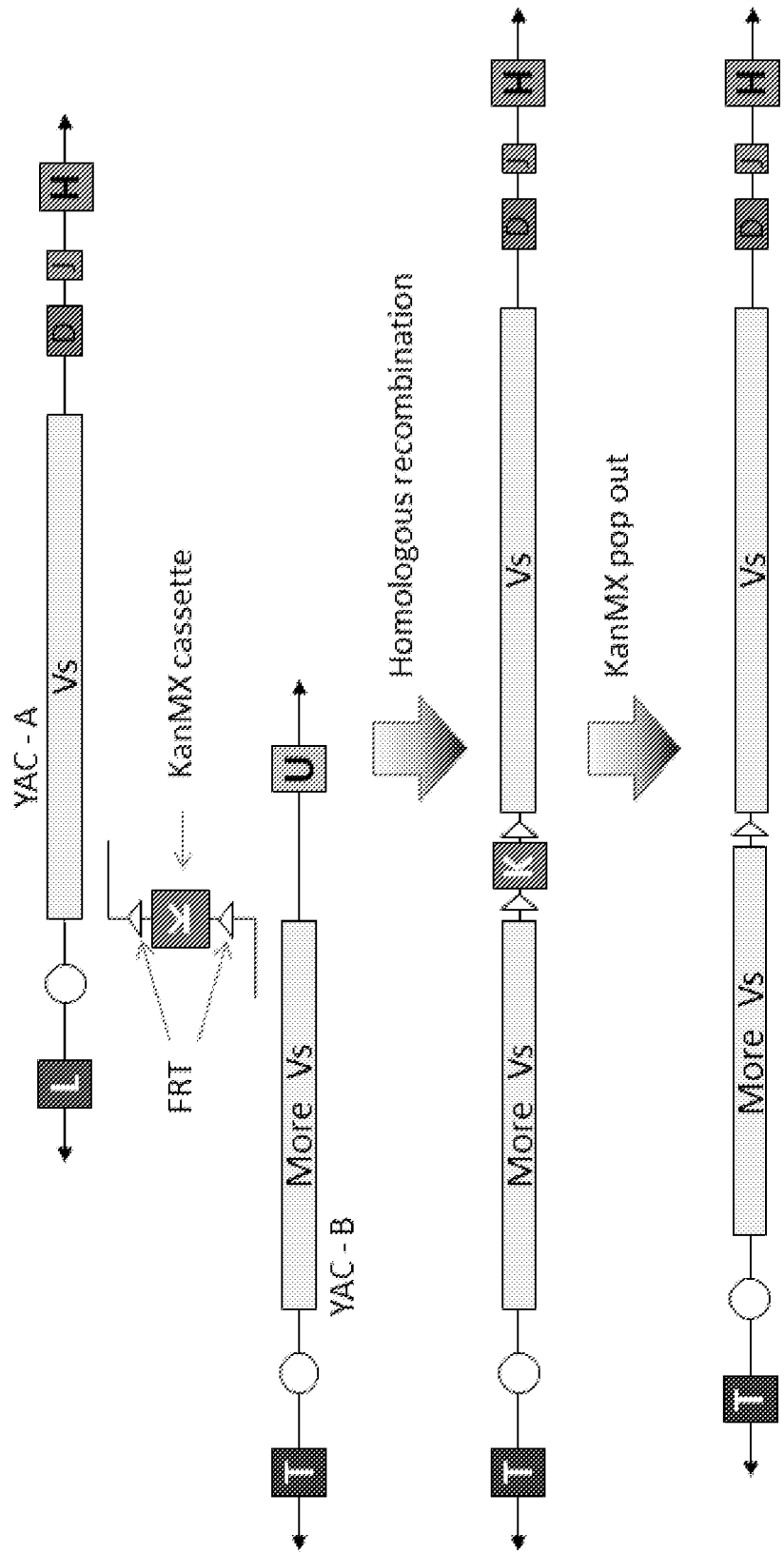
Figure 6:
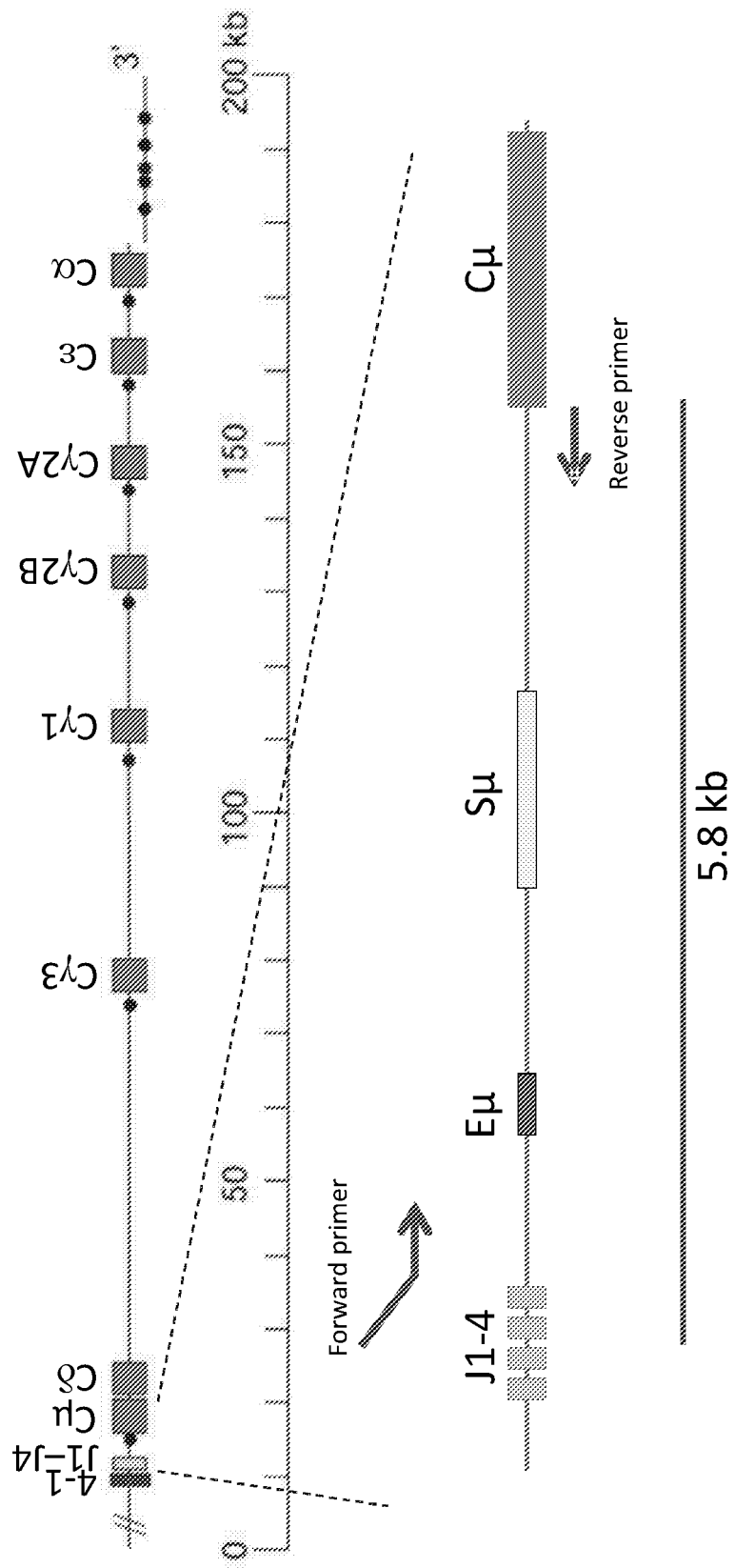
Figure 8:
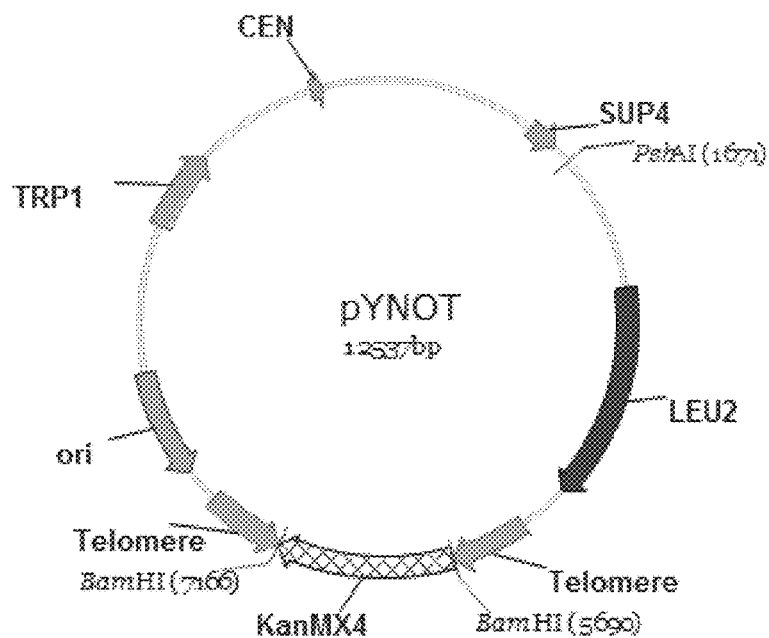
Figure 9:
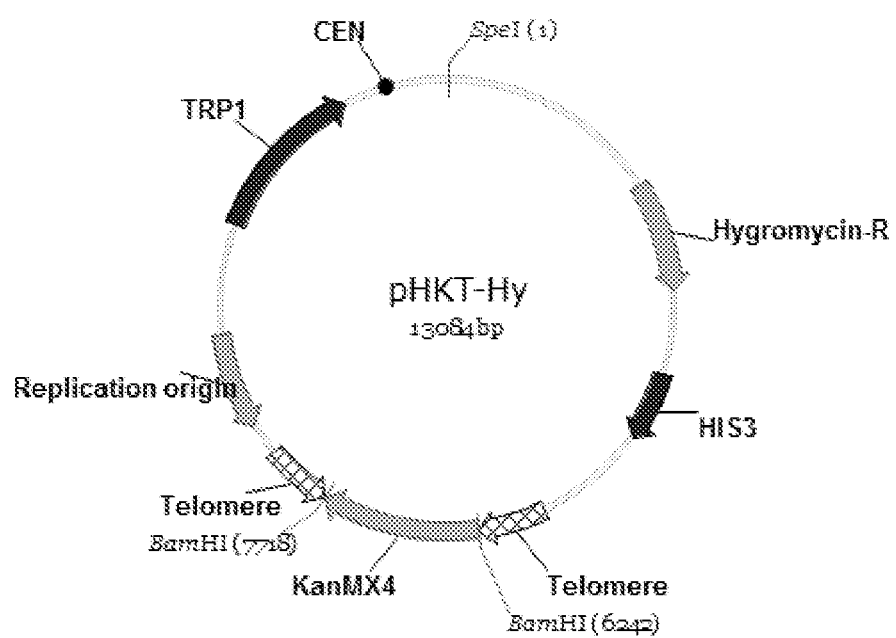
Figure 10:
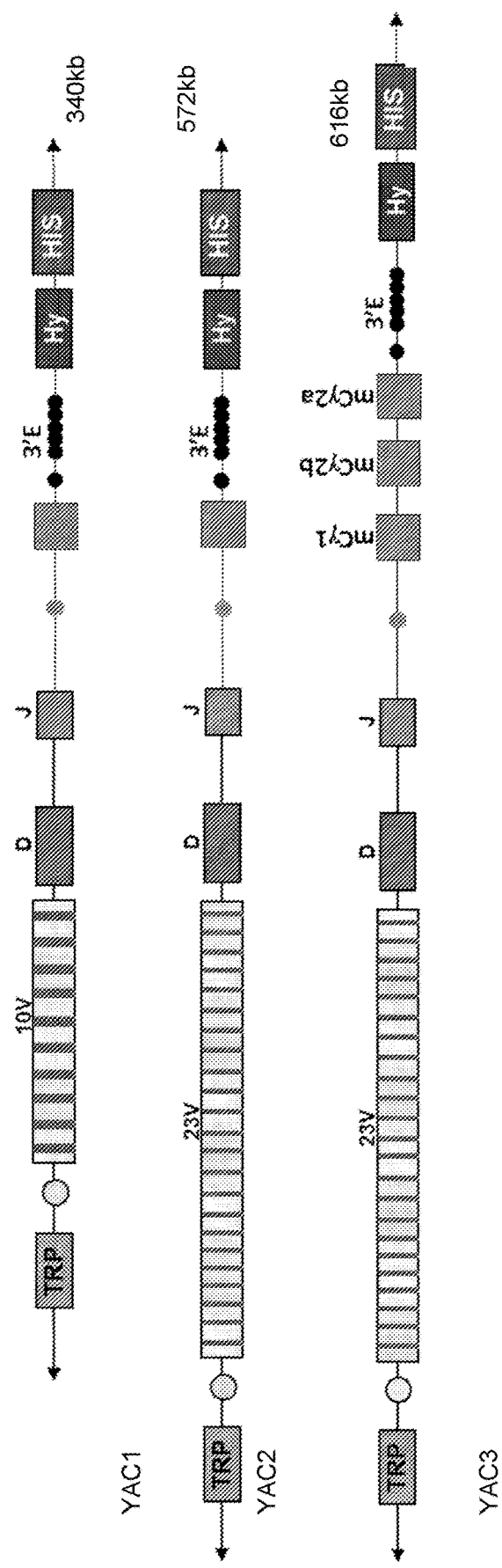
Figure 11:
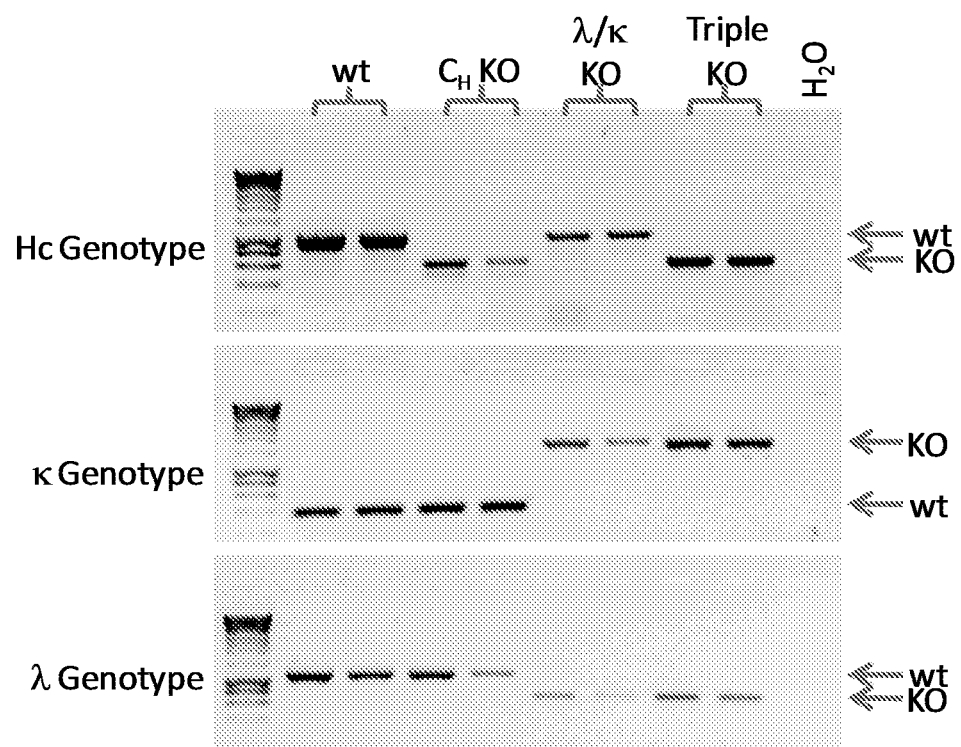
Figure 12:
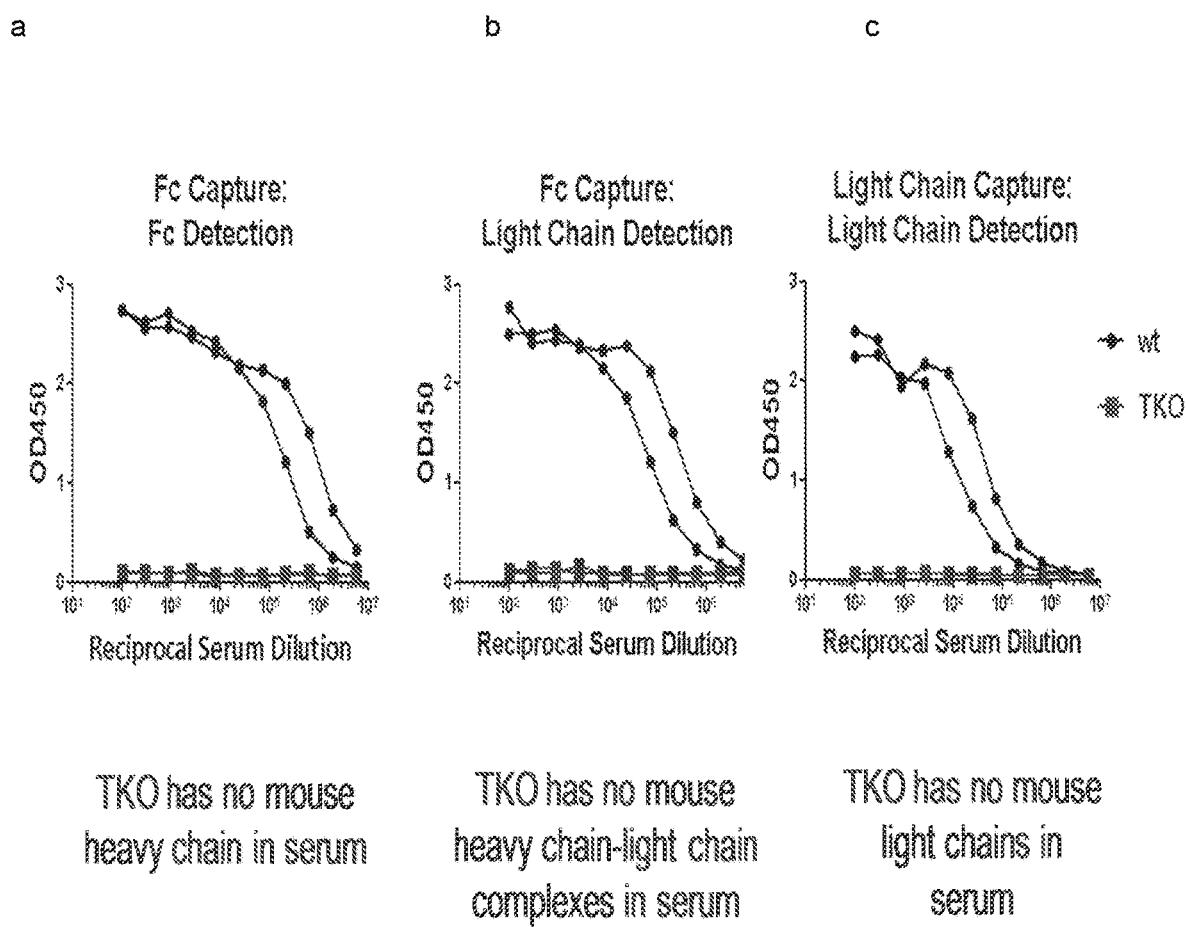
Figure 13:
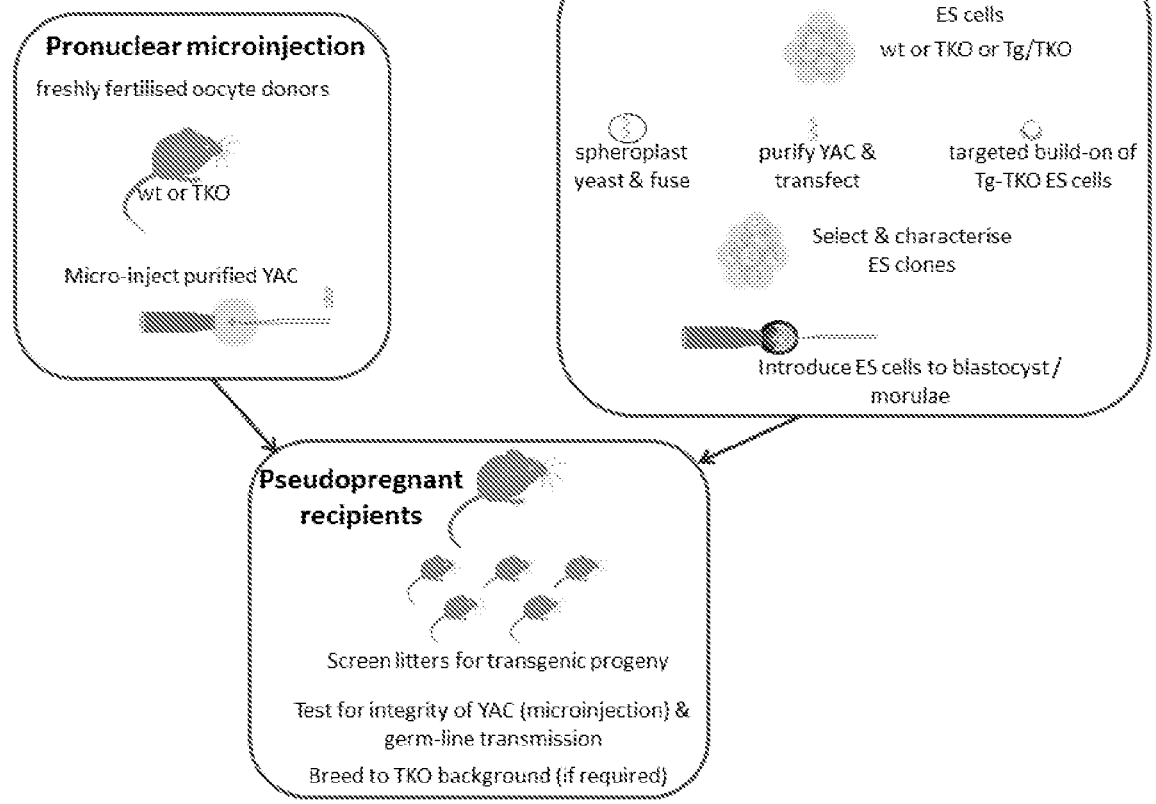
Figure 14:
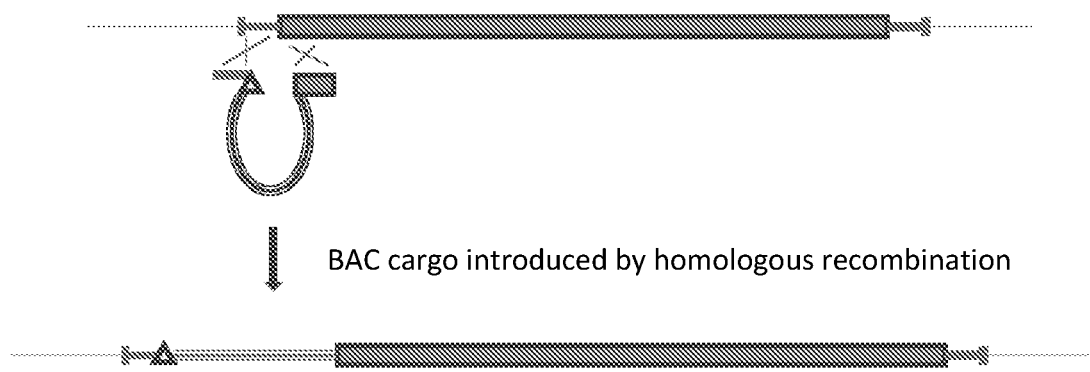
Figure 15:
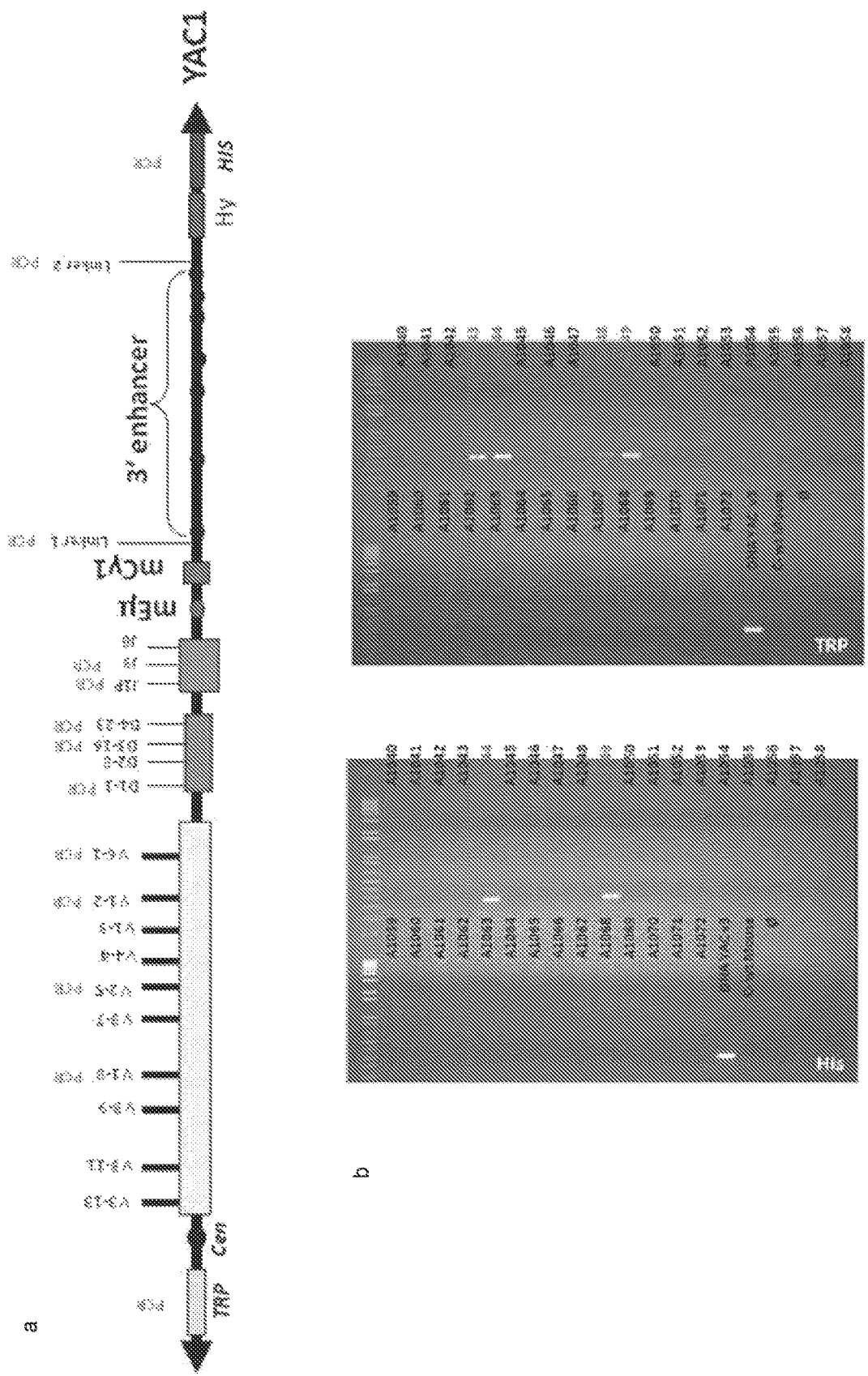
Figure 15:
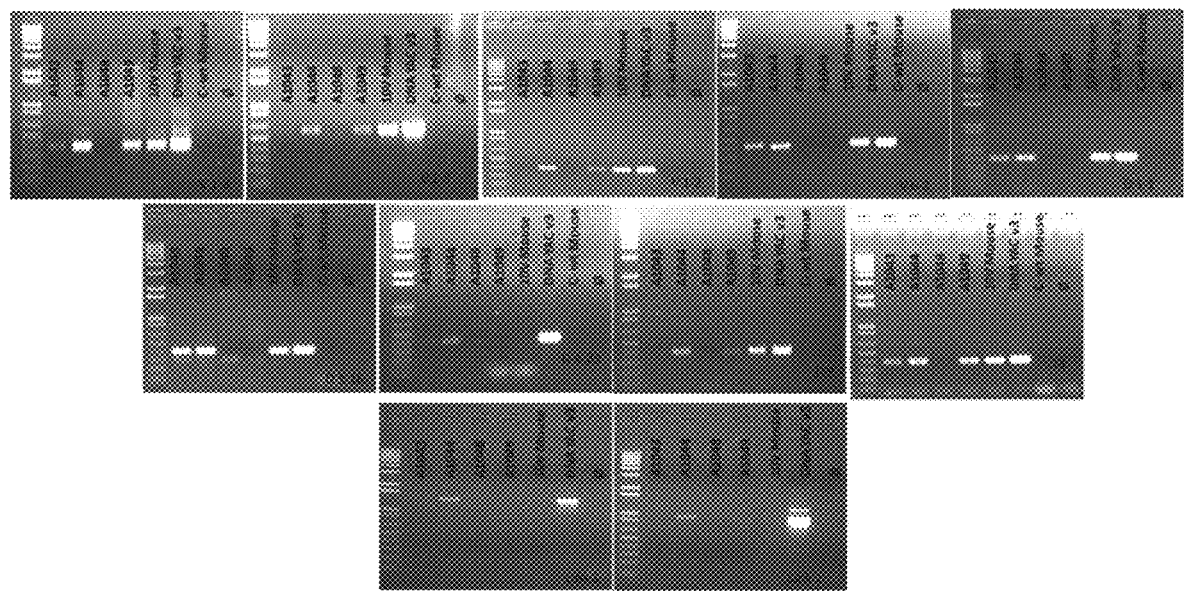
Figure 16:
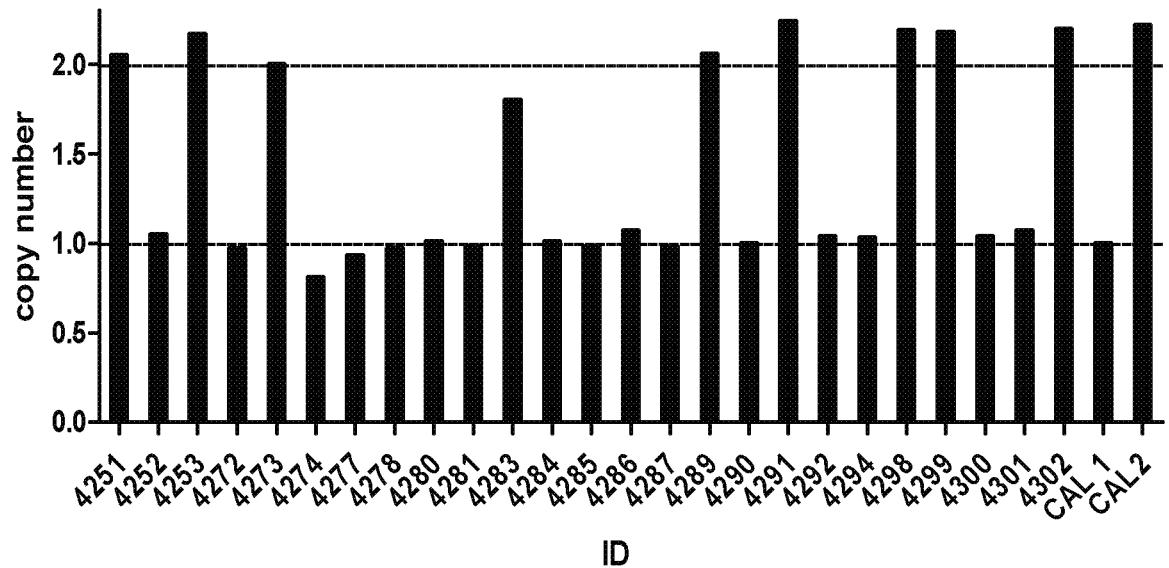
Figure 17:
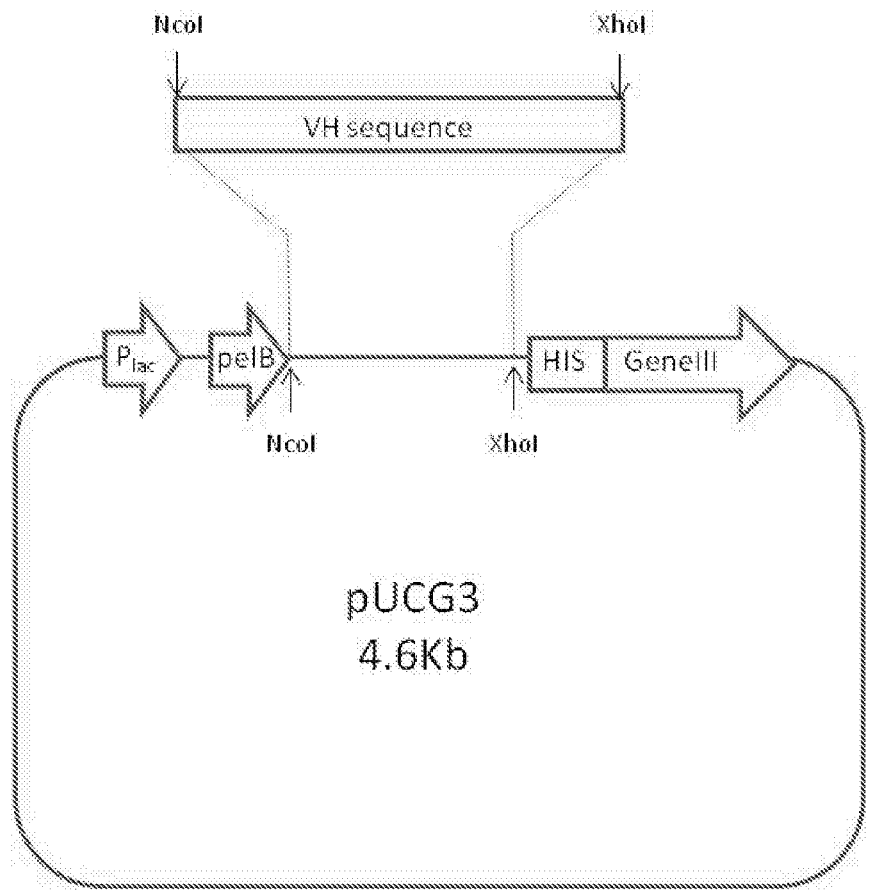
Figures 18, 19:
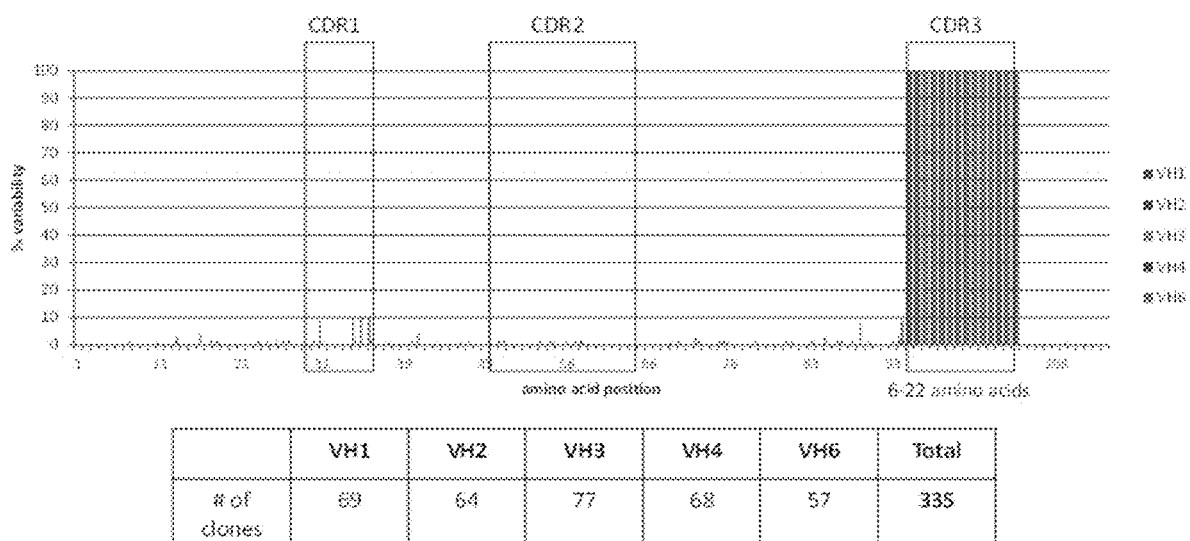
Figure 19:
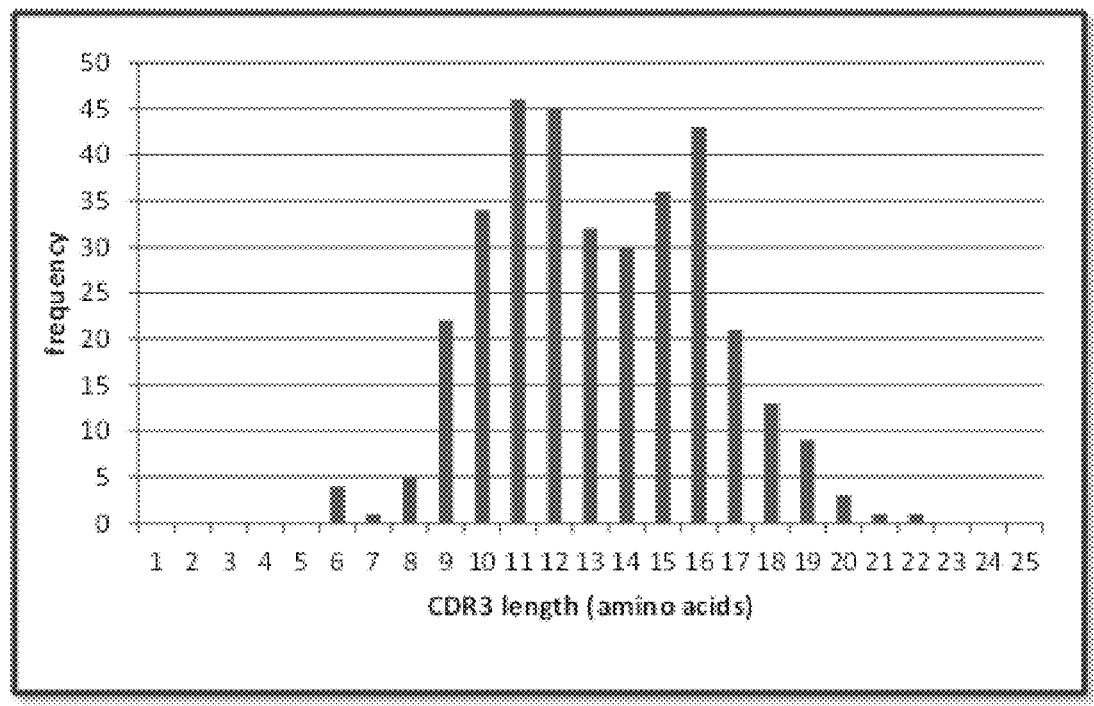

FIG. 1: Human BACs.
FIG. 2: Mouse BACs.
FIG. 3: pYAC3 with cloned a1 and a2.
FIG. 4: Conversion of BAC into YAC by TAR cloning.
FIG. 5: Joining the two YACs by BIT. L: LYS2; A: ADE2; T: TRP1; U: URA3; K: KANr.
FIG. 6: Amplification of the mouse Eμ-Sμ region.
FIG. 7: Amplification of the mouse Cγ1 fragment with deleted $C_H1$.
FIG. 8: pYNOT vector.
FIG. 9: Vector pHKT-Hy for generating Hy-HIS3-telomere YAC arm.
FIG. 10: Constructs of the invention.
YAC1: From left to right, telomere-yeast TRP1 marker gene-Centromere-10 human V genes-human D genes-human J genes-mouse μ enhancer and switch-mouse Cγ1 ($C_H1\Delta$) gene-mouse 3' enhancer-Hygromycin resistant gene-yeast marker gene HIS3-telomere.
YAC2: From left to right; telomere-yeast TRP1 marker gene-Centromere-23 human V genes-human D genes-human J genes-mouse μ enhancer and switch-mouse Cγ1 ($C_H1\Delta$) gene-mouse 3' enhancer-Hygromycin resistant gene-yeast marker gene HIS3-telomere.
YAC3: From left to right, telomere-yeast TRP1 marker gene-Centromere-23 human V genes-human D genes-human J genes-mouse μ enhancer and switch-mouse Cγ1 ($C_H1\Delta$) gene-mouse Cγ2b ($C_H1\Delta$) gene-mouse Cγ2a ($C_H1\Delta$) gene-mouse 3' enhancer-Hygromycin resistant gene-yeast marker gene HIS3-telomere.
FIG. 11: Genotyping PCR reactions using gDNA from mice with or without targeted endogenous immunoglobulin chain loci.
FIG. 12: ELISA of mouse immunoglobulin proteins in serum. The TKO mouse has no mouse heavy chain in the serum. The TKO mouse has no mouse heavy chain-light chain complexes in the serum. The TKO mouse has no mouse light chains in the serum.
FIG. 13: Schematic presentation of transgenesis procedures.
FIG. 14: Schematic of targeted build-on of YAC transgene within an ES clone.
FIG. 15: PCR screening of genomic DNA from pups born following pronuclear microinjection and testing of germline transmission from F0 to F1 generation. a) YAC1, b) gel electrophoresis, c) results.
FIG. 16: Copy number of inserted YAC transgene.
FIG. 17: Map of phagemid vector.
FIG. 18: Examples of transcripts generated from rearranged transgenic locus. The VH3 sequence is SEQ ID NO:

148; the P6C6 sequence is SEQ ID NO: 149; the P6C3 sequence is SEQ ID NO: 150; and the P6C11 sequence is SEQ ID NO: 151.

FIG. 19: a) and b) Diversity of cloned $V_H$ sequences. Sequence analysis of transcripts isolated from a single naïve transgenic YAC1 mouse. Total sequences analysed: 409. Number of different CDR3: 346. Mean CDR3 length: 13.24. All V genes are utilised.

Figure 20:
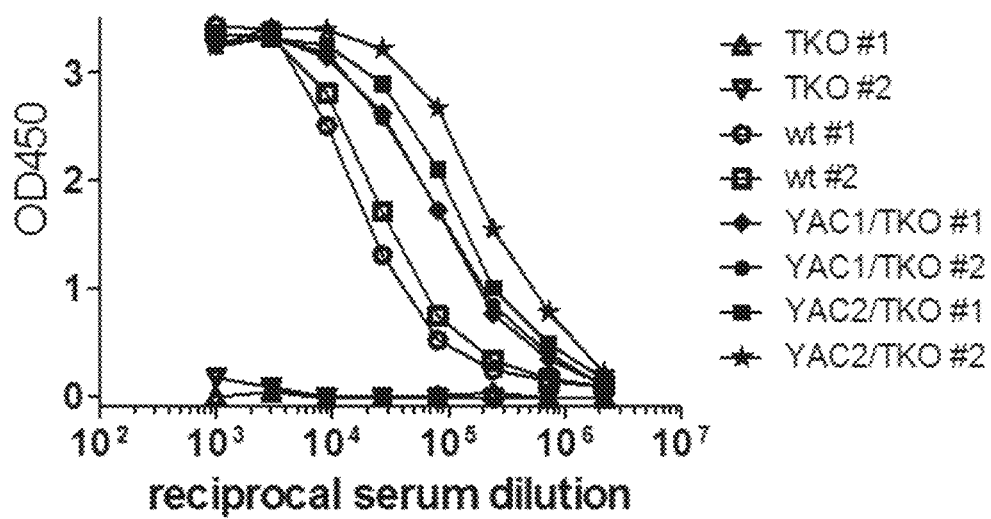

FIG. 20: ELISA detecting HCAb in serum.

Figure 21:
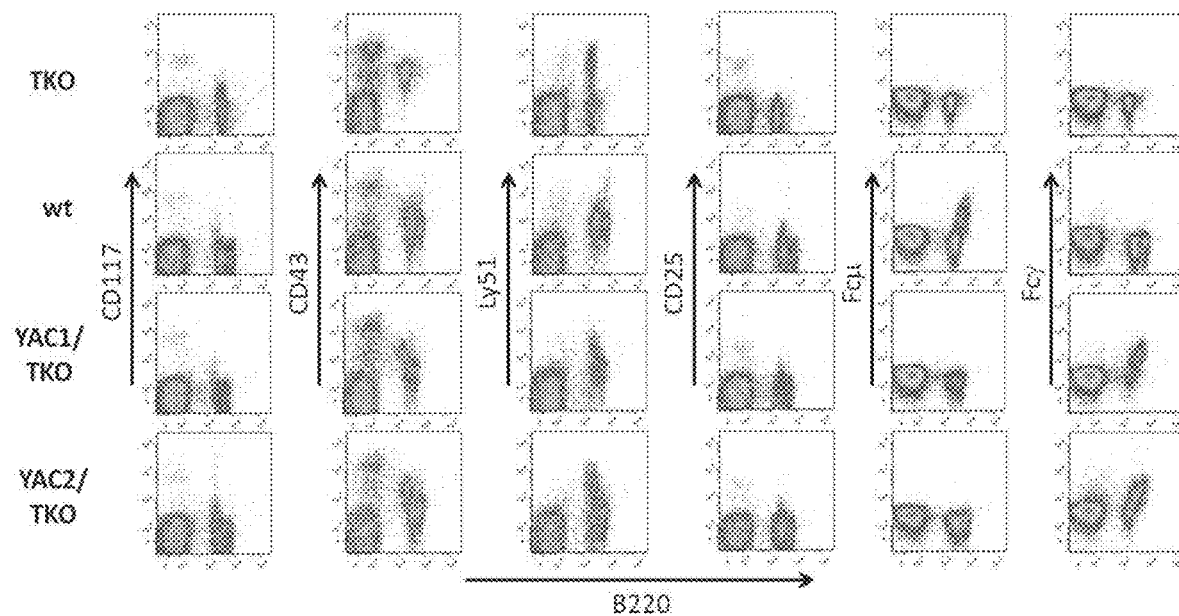

FIG. 21: Flow Cytometry using stained bone marrow cells.

Figure 22:
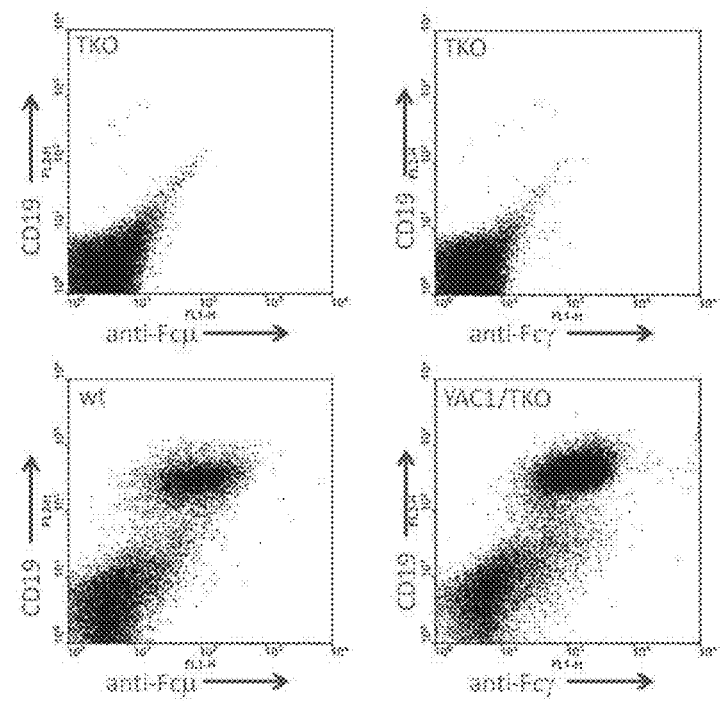
Figure 22:
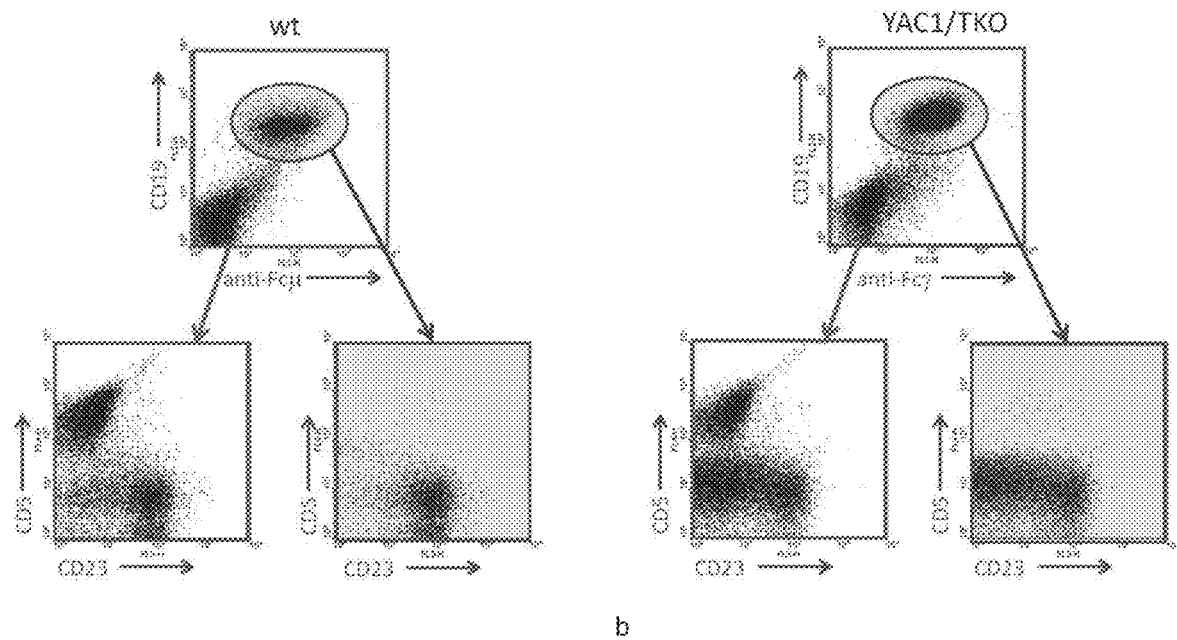
Figure 22:
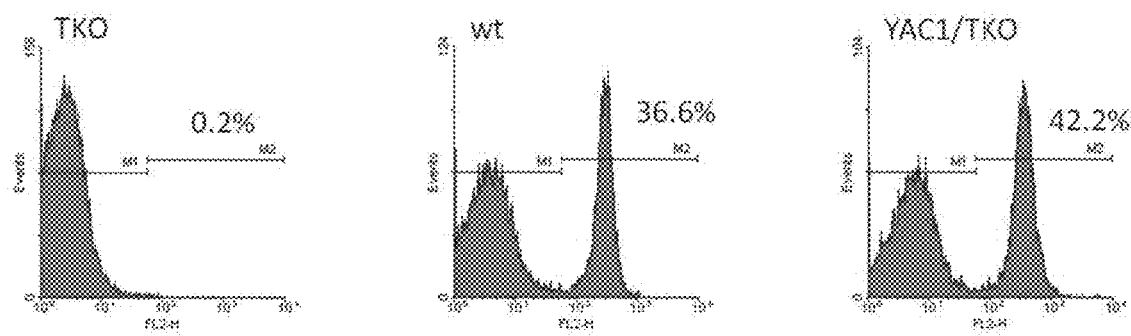

FIG. 22: a) to c) Flow cytometry showing staining of splenocytes.

Figure 23:
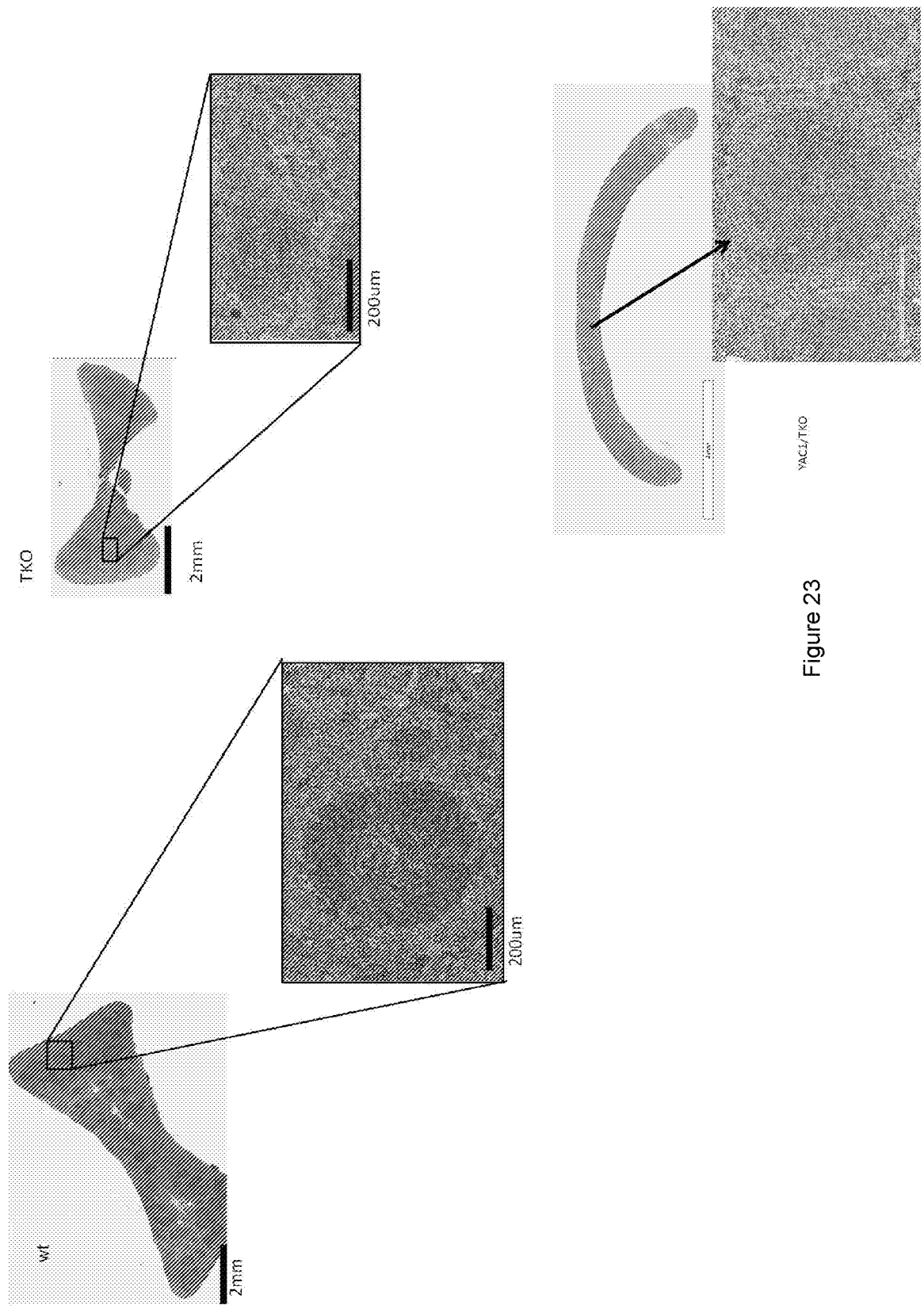

FIG. 23: Immunohistochemistry of spleen sections following staining with haematoxylin and eosin.

Figure 24:
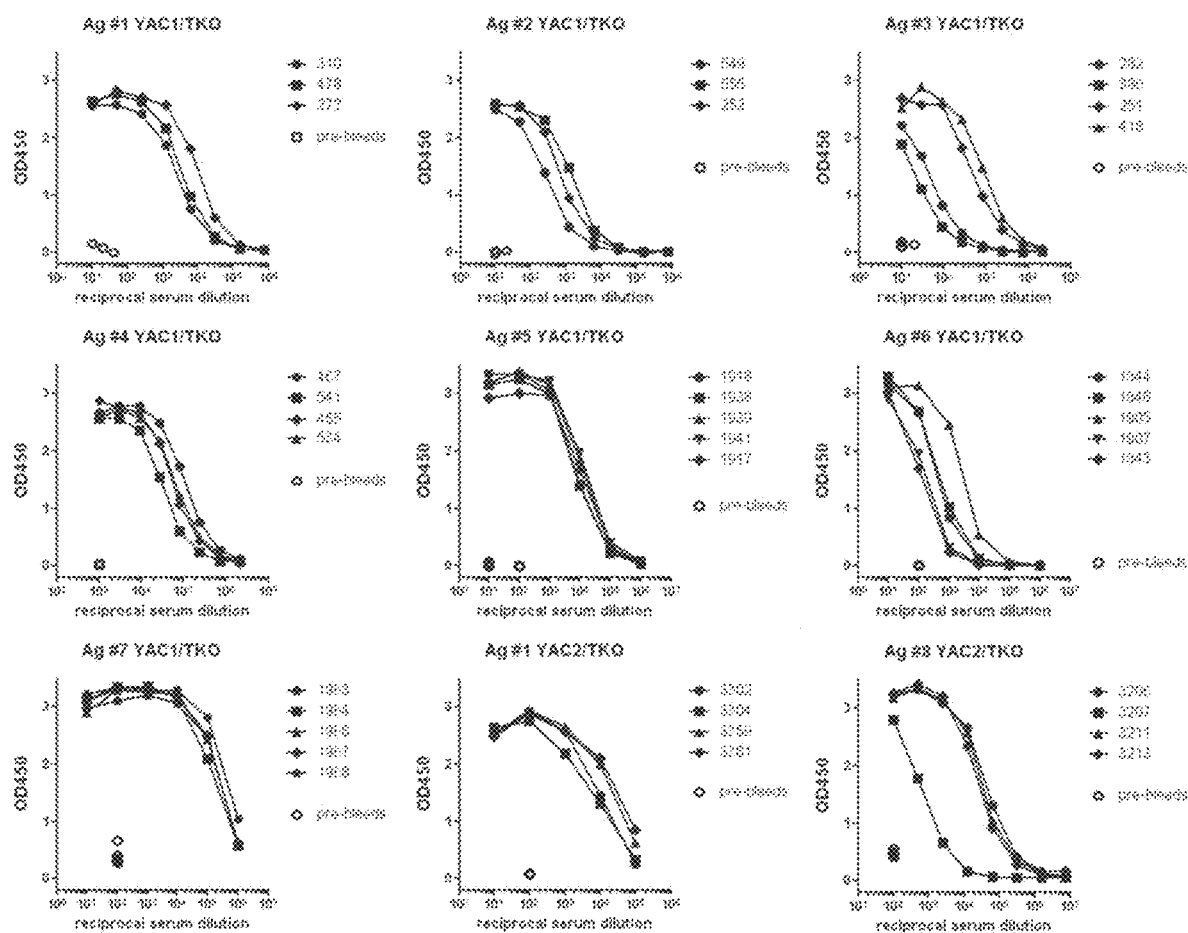

FIG. 24: ELISA detecting HCAb responses to immunisation. Serum from mice immunised with various antigens was collected before (pre-bleeds) immunisation and at the end of the experiment and tested in ELISA for binding to the target antigen.

Figure 25:
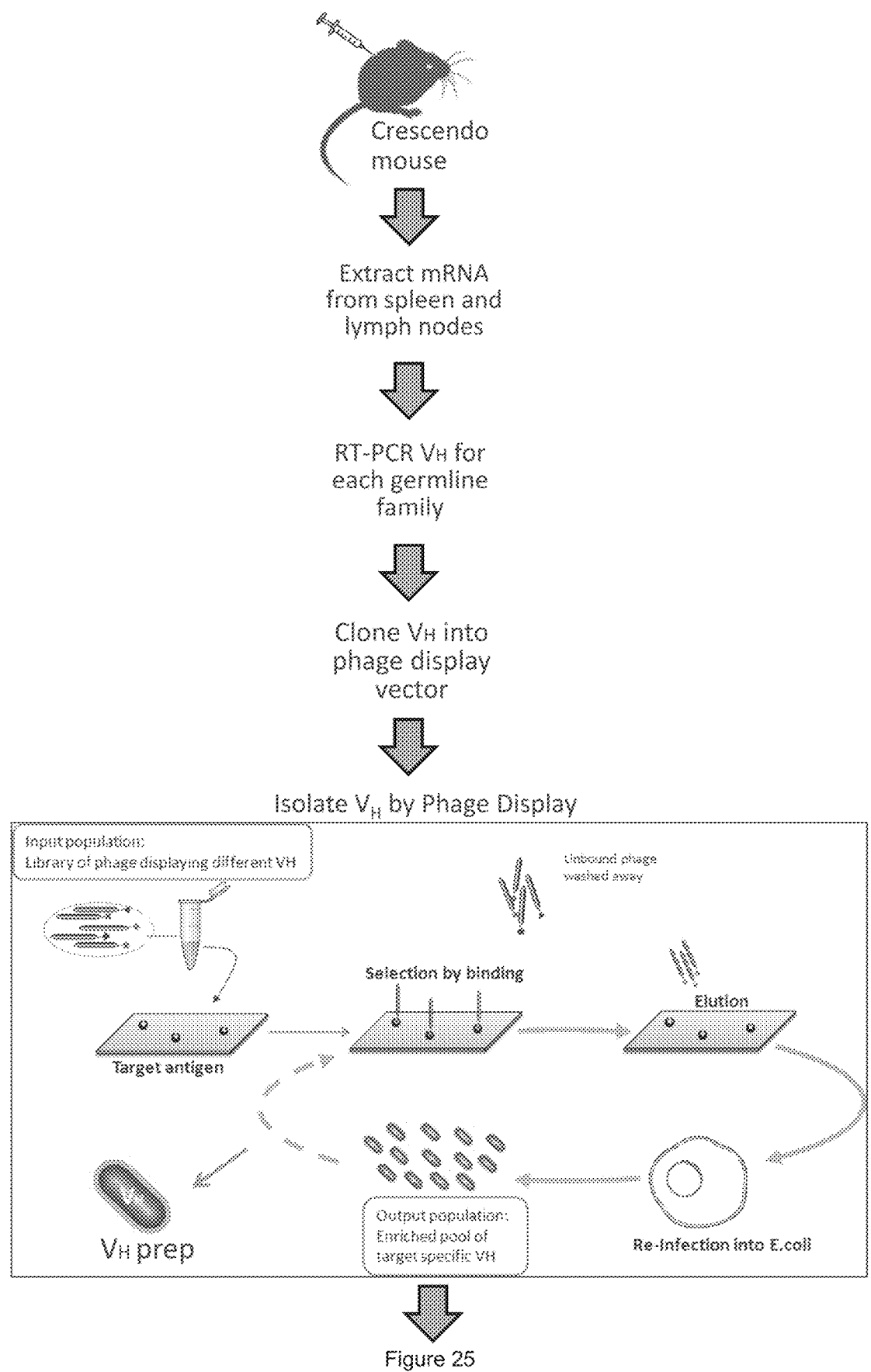

FIG. 25: Schematic of phage display selection process.

Figures 25, 26:

FIG. 26: ELISA of HIS-tagged crude $V_H$ preparations before and following phage selection of cloned $V_H$ from an immunised mouse.

Figure 27:
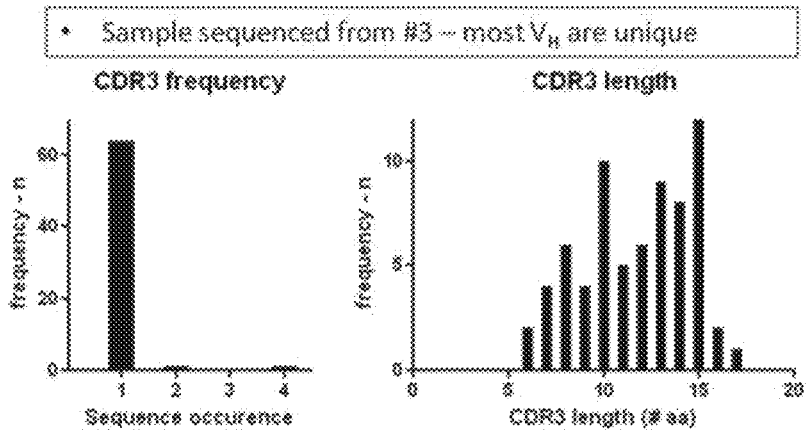
Figure 27:
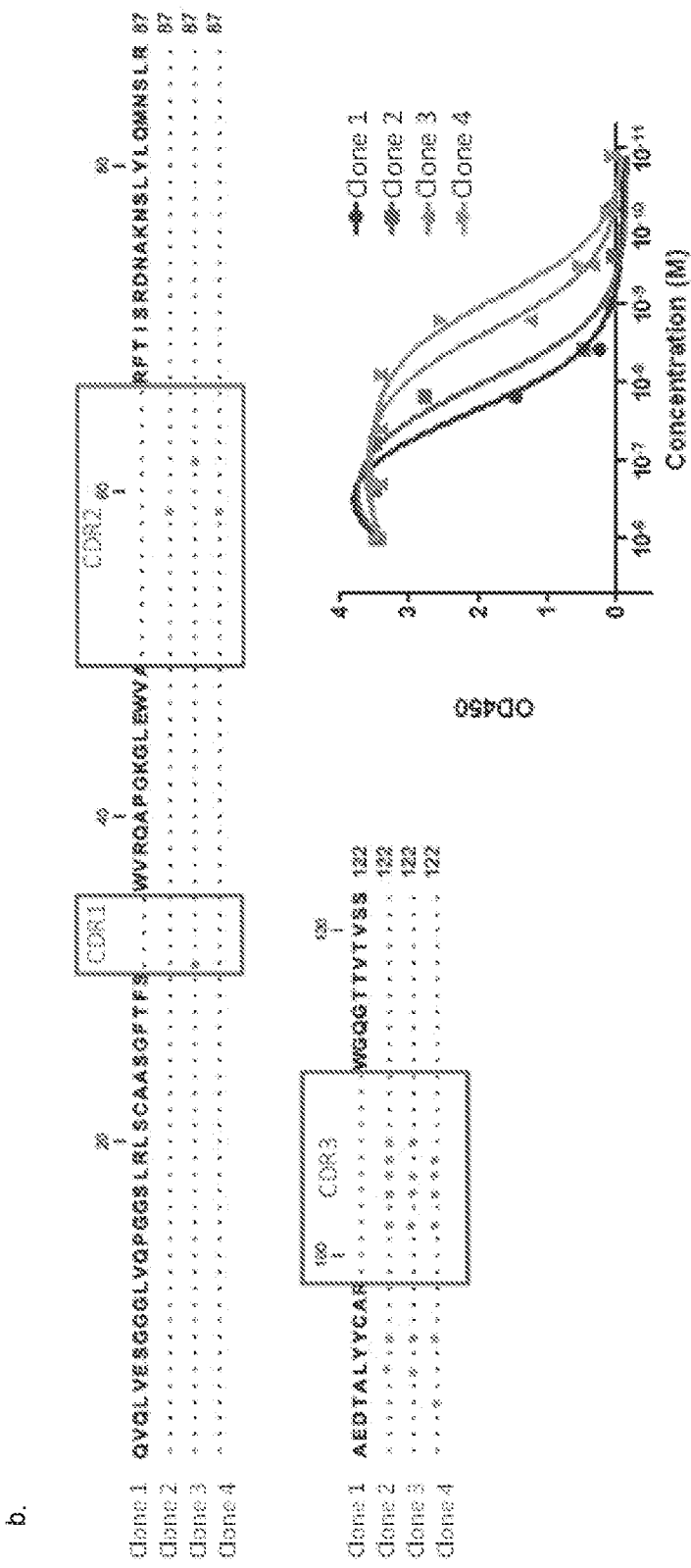

FIG. 27: Sequence of pre- and post-selection libraries from an immunised mouse a). Library sizes and sequence diversity prior to selection. Phage libraries were constructed from 4 immunised mice and, prior to undertaking selection on antigen a small number (n=69) of clones were sampled from one of the libraries and sequenced. The distribution of the CDR3 length amongst these clones and the frequency of occurrence of each CDR3 sequence are represented. Clone 1 with 4 framework regions (SEQ ID NOs: 143 (before CDR1), 144 (after CDR1), 145 (after CDR2), 146 (before CDR3), 147 (after CDR3) and CDRs) is shown in b) c). Examples of in vivo somatic hypermutation leading to higher affinity binding in ELISA are shown. Summary of antigen-binding $V_H$ families isolated using phage display from immunised mice.

Figure 28:
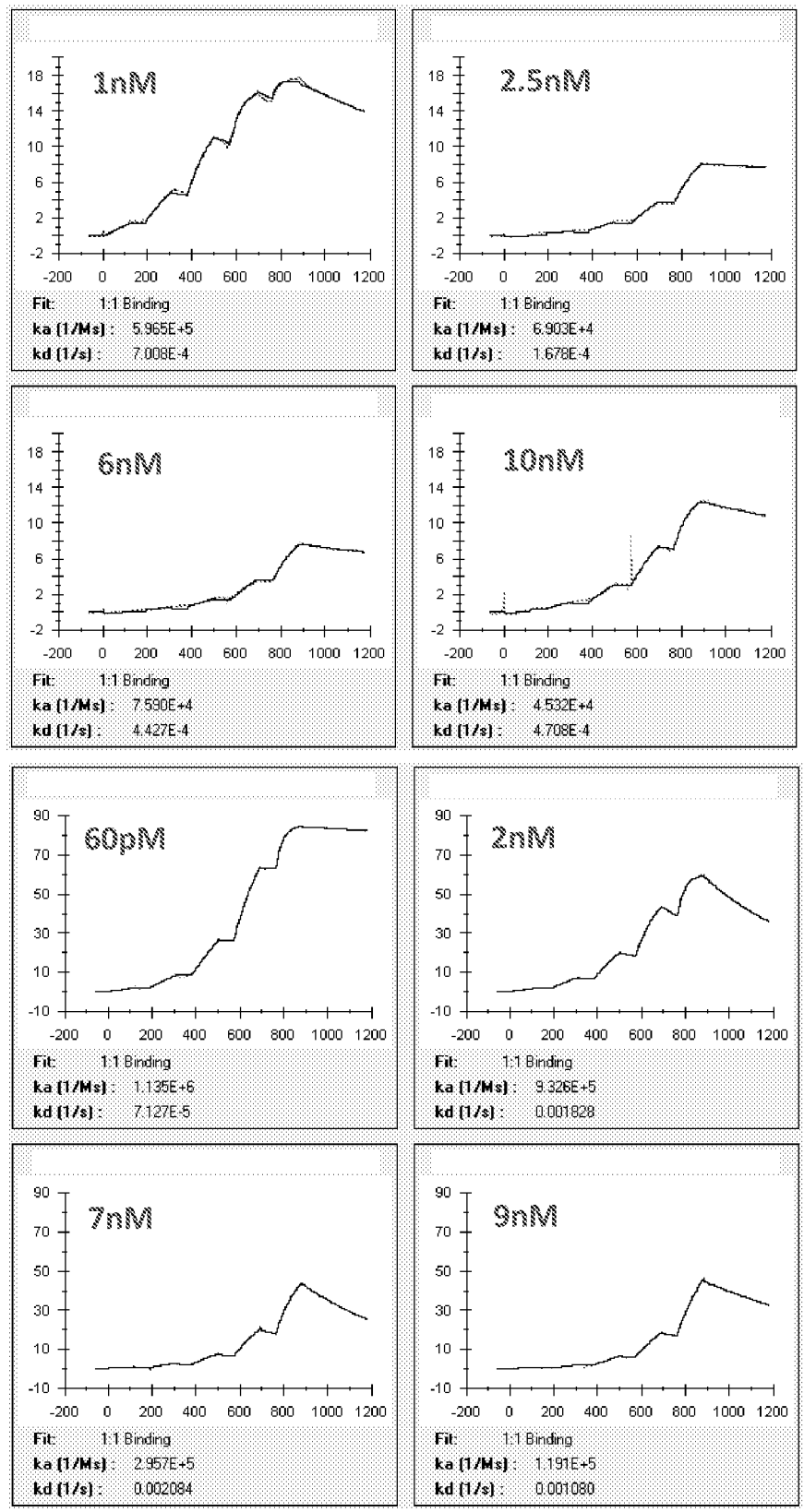

FIG. 28: BIAcore measurements of binding kinetics for selected $V_H$.

Figure 29:
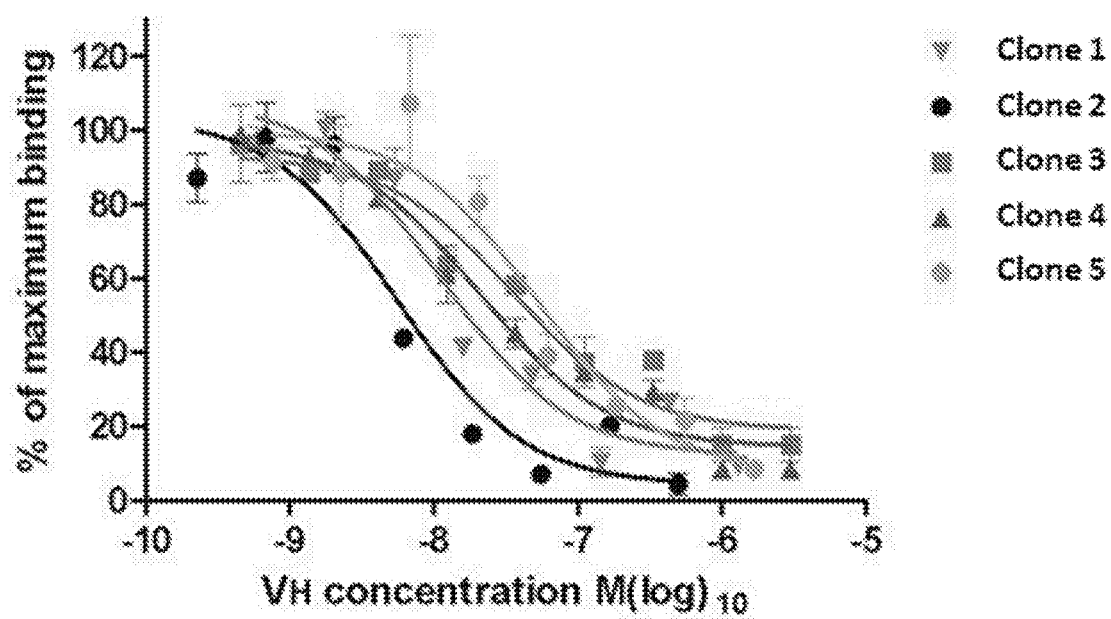

FIG. 29: $V_H$ mediated inhibition of ligand binding to receptor.

Figure 30:
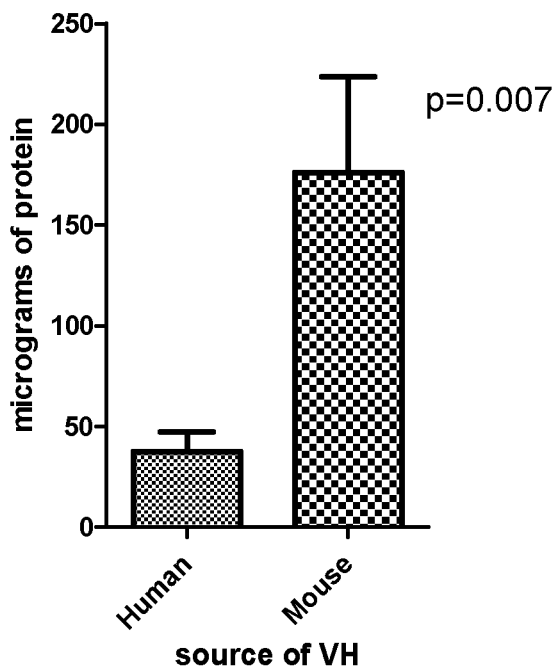
Figure 30:
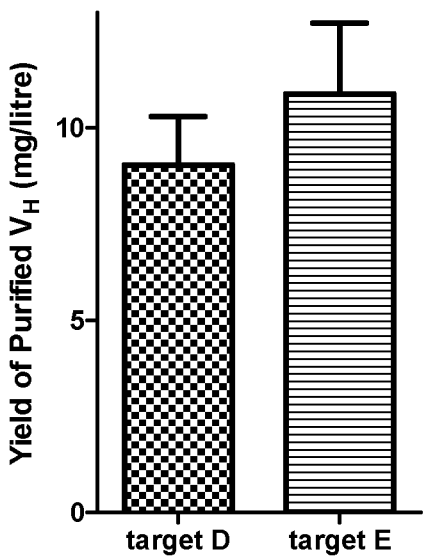

FIG. 30: a) and b) Yield of cloned $V_H$ from laboratory scale cultures.

Figure 31:
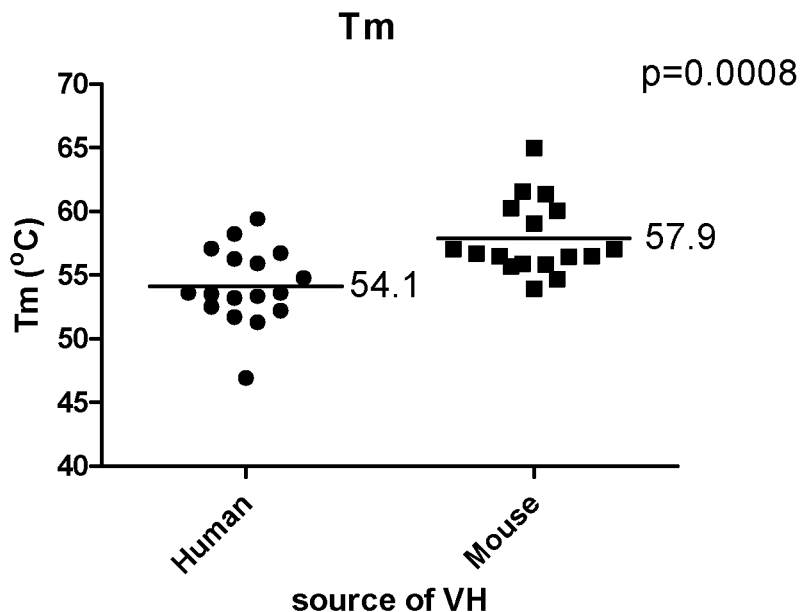

FIG. 31: Melting temperatures of purified recombinant $V_H$.

Figure 32:
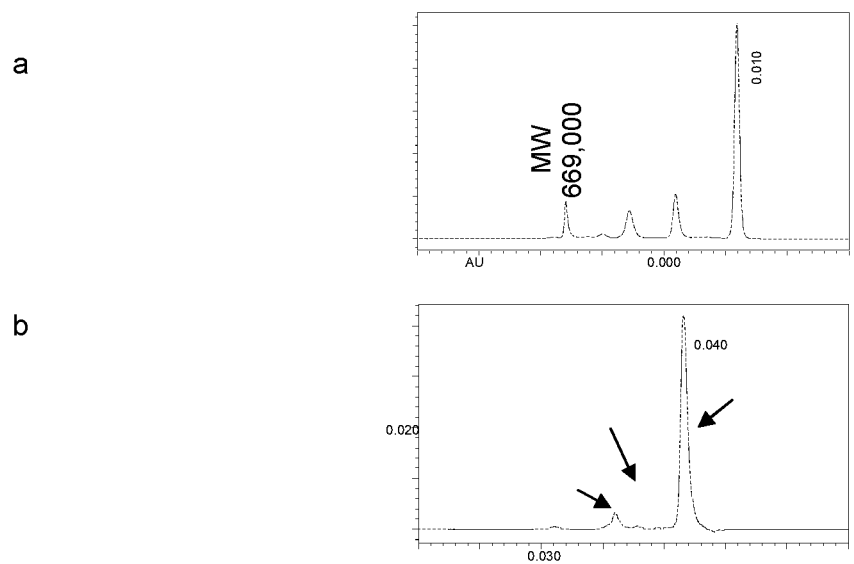
Figure 32:
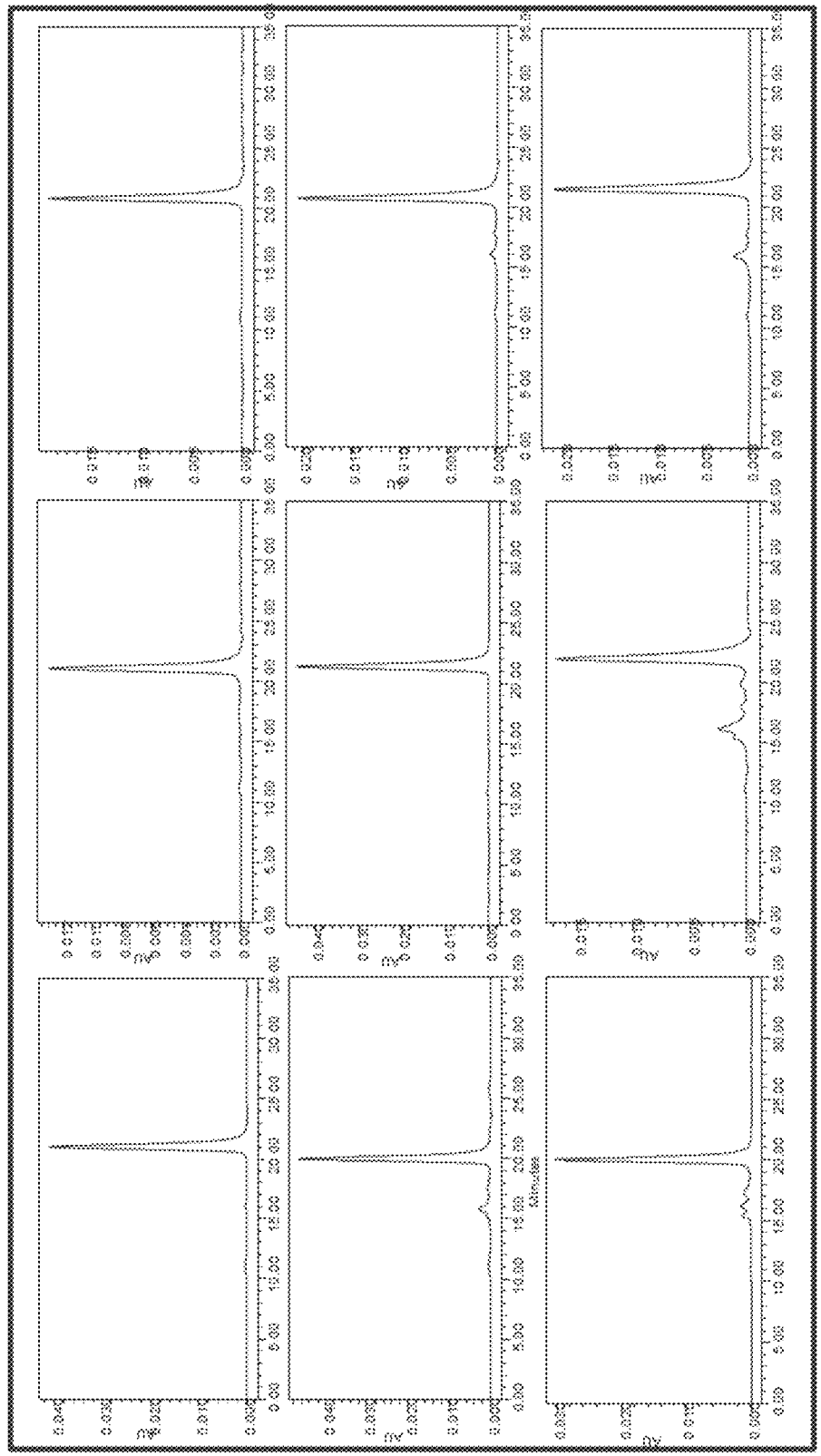

FIG. 32: HPLC analysis of purified $V_H$.

Figure 33:
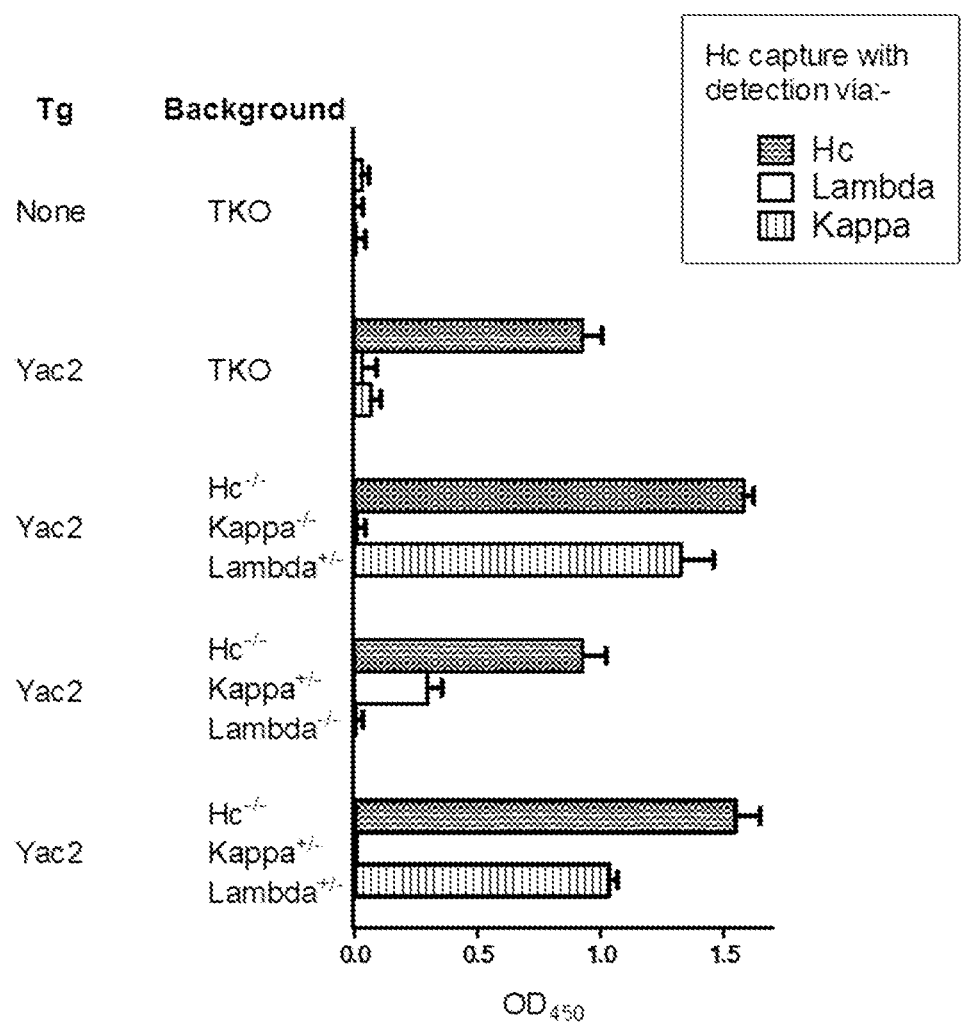

FIG. 33: ELISA demonstrating that transgenic mice carrying YAC2 on the Triple KO background produce HCAb free from endogenous light chain contamination. The presence of any endogenous light chain (HC −/−, Kappa −/−, Lambda +/− OR HC −/−, Kappa +/−, Lambda −/− OR HC −/−, Kappa +/−, Lambda +/−) results in HCAb pairing with light chain, FIG. 34: Kabat and Wu Variability Plot of 812 antigen-binding VH clones isolated from mice immunised with 3 different antigens. The % variability at each amino acid position is plotted. At each indicated amino acid position, there are 5 bars representing, in order, VH1 (16 clones), VH2 (14 clones), VH3 (514 clones), VH4 (163 clones) and VH6 (105 clones) family sequences. The sequences that form the CDR1, CDR2 and CDR3 loops are boxed.

Figure 35:
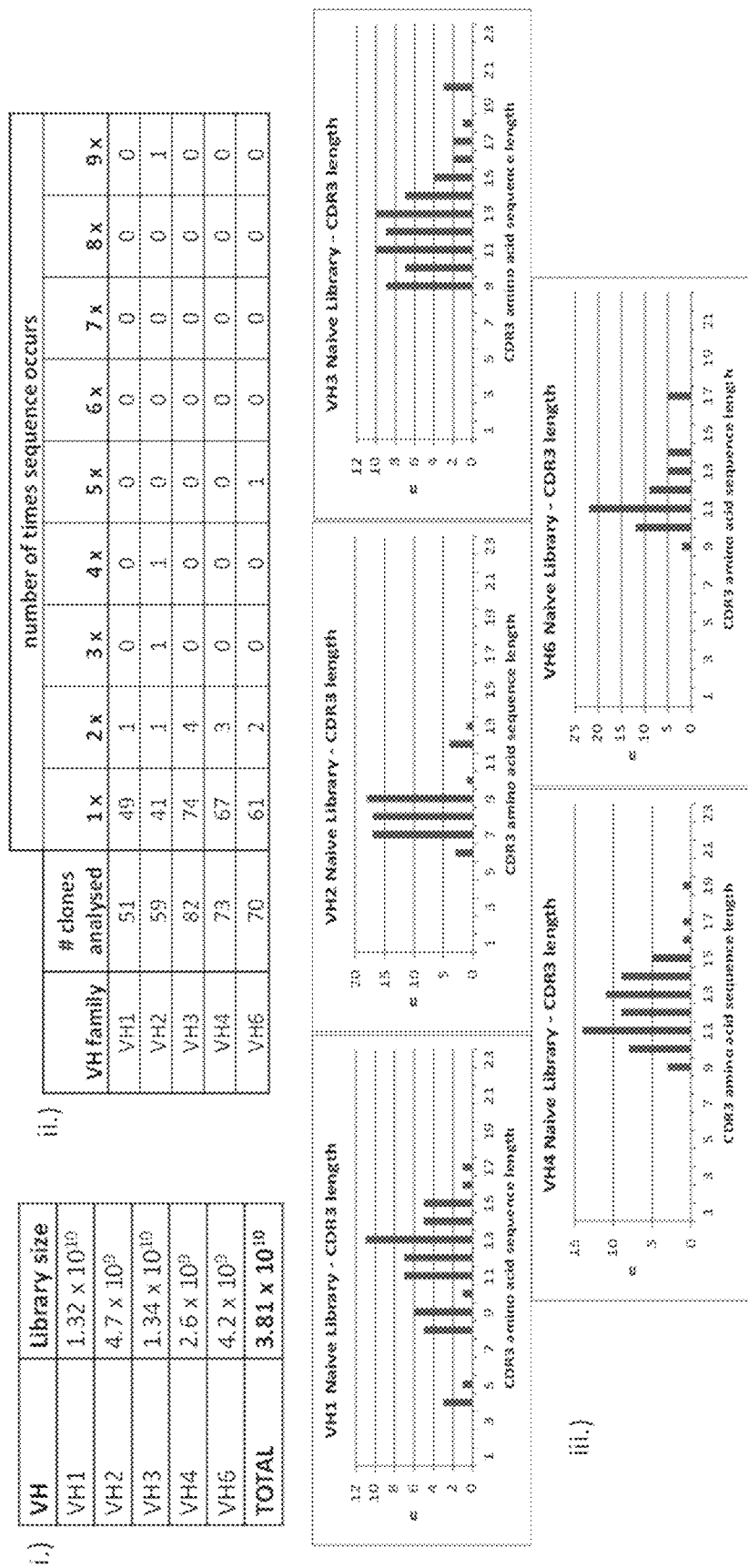

FIG. 35: Naive Libraries. VH1, 2, 3, 4 and 6 libraries were generated from the spleens of 113 naïve YAC1 mice.

i.) Number of clones in each library.
ii.) Sequence analyses of samples from each of the naïve libraries indicates good diversity.
iii.) Frequencies of CDR3 amino acid lengths in a sequence sample from each of the naïve libraries.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. The practice of the present invention will employ, unless otherwise indicated, conventional techniques of immunology, molecular biology, chemistry, biochemistry and recombinant DNA technology, which are within the skill of the art. Such techniques are explained fully in the literature.

Yeast artificial chromosomes (YACs) are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g. Bruschi, C. V. and Gjuracic, K. Yeast Artificial Chromosomes, ENCYCLOPEDIA OF LIFE SCIENCES 2002 Macmillan Publishers Ltd, Nature Publishing Group els.net).

The inventors have prepared a series of yeast artificial chromosomes (YACs) for expression in mice (FIG. 10). These YACs encode a human heavy chain locus capable of undergoing somatic recombination in transgenic mice to give rise to a B cell heavy-chain-only antibody repertoire. The series of YACs has increasing complexity with YAC1 having fewer $V_H$ gene segments than YAC2 or YAC3 and YAC3 having further immunoglobulin constant region genes available. As described herein, this series of YACs can form the basis for further YAC constructs with additional $V_H$ genes such that V(N) has at least 10 human $V_H$ in germline configuration in combination with a murine constant region.

It will be apparent to a skilled person that additional features, for example to assist with transfection of constructs to embryonic stem cells, selection and screening of ES clones or for promoting defined integration during transgenesis, can also be included in the YAC constructs of the invention. It will be apparent to a skilled person that vectors other than YACs can be used. As described herein, the vector, vector construct, construct or transgene of the invention can be employed in methods for the generation of fully functional, antigen-specific, high affinity HCAb or VH binding domains of a class of choice in transgenic mice in response to antigen challenge.

The expression vector of the invention has a chimeric heavy chain locus comprising sequences of human and murine origin. Thus, the vector comprises a heterologous heavy chain locus. The vector comprises a heavy chain constant region which does not encode a $C_H1$ domain. The vector can be used for the expression of a heterologous heavy chain locus in rodents. When expressed in rodents, for example mice, the locus is capable of forming a stable and soluble HCAb or $V_H$ domain.

In one embodiment of the various aspects of the invention described herein, said vector is a YAC. However, other vectors known to the skilled person, such as BACs, can also be used according to the invention.

In a first aspect, the invention relates to a vector comprising
a) at least 10 functional human heavy chain V genes wherein at least 10 functional human heavy chain V genes are in their natural configuration;
b) at least one human heavy chain D gene and at least one human heavy chain J gene;
c) a murine C gene which lacks the $C_H1$ exon.

In one embodiment, the construct comprises a murine 3' enhancer region or gene. In one embodiment, said murine 3' enhancer region or gene is at least about 42 kb in size. In one embodiment, said murine 3' enhancer region comprises one or more enhancer element selected from enhancer elements hs3A, hs1.2, hs3B, hs4, hs5, hs6 and hs7. In one embodiment, said murine 3' enhancer region comprises enhancer elements hs3A, hs1.2, hs3B, hs4, hs5, hs6 and hs7.

In one embodiment, the vector comprises more than one murine C gene. In one embodiment, said murine C gene is a murine Cγ1 gene.

In one embodiment, the vector comprises a murine μ enhancer and switch μ element or switch γ element. Thus, the switch μ element or switch γ element is located downstream of the murine μ enhancer and these elements are thus in their natural configuration.

Thus, in one embodiment, the invention relates to a vector comprising
a) at least 10 functional human heavy chain V genes wherein at least 10 functional human heavy chain V genes are substantially in their natural configuration;
b) at least one human heavy chain D gene and at least one human heavy chain J gene;
c) a murine μ enhancer and switch μ element or switch γ element;
d) a murine Cγ1 gene which lacks the $C_H1$ exon and
e) a murine 3' enhancer gene comprising enhancer elements hs3A, hs1.2, hs3B, hs4, hs5, hs6 and hs7.

The elements set out in a) to e) are in 5'→3' order. The vector of the invention is chimeric and comprises human and murine sequences. The human sequences are located at the 5' end of the vector and comprise heavy chain V, D and J genes. The 3' region of the vector located downstream of the human J gene comprises sequences of murine origin and does not comprise sequences of human origin.

As mentioned elsewhere, in one embodiment, the vector is a YAC.

In one embodiment, the vector comprises at least about 0.5 MB human sequence.

According to the invention, the vector comprises at least 10 functional human heavy chain V genes in substantially natural configuration. In one embodiment, the vector may comprise at least 10 to all functional human V genes. In one embodiment, the number of V genes is 10 to about 44. In one embodiment, the number of functional V genes is 10 to 20, 10 to 30 or 10 to 44. In one embodiment, the number of functional V genes is 10, 11, 12, 13, 14, 15, 16, 17, 18, 19, 20, 21, 22, 23, 24, 25 26, 27, 28, 29, 30, 31, 32, 33, 34, 35, 36, 37, 28, 29, 40, 41, 42, 43 or 44. In one embodiment, the number of functional V genes is 10 to 23.

In one embodiment, the vector may comprise tandem repeats of functional V genes. Each tandem repeat comprises at least 10 human heavy chain V genes that are substantially in their natural configuration. Accordingly, the vector may comprise at least 10 to hundreds of functional V genes, for example 10 to about 50, 10 to about 100, 10 to about 200 or more. In one embodiment, the vector may comprise more than 10 functional V genes. Within each tandem repeat, at least 10 functional V genes are substantially in their natural configuration.

For example, vectors according to the invention having 10 or 23 functional human heavy chain V genes respectively are shown as YAC 1, 2 and 3 in FIG. 10. However, a skilled person would appreciate that the invention is not limited to the YACs shown in FIG. 10 and additional functional V genes can be included, provided that the other design features of the vector according to the invention are not compromised.

The V genes are of human origin and functional. Accordingly, the V genes encode for a gene product and are not pseudogenes (although pseudogenes may be present within the construct, but are not counted in the determination of the number of functional V genes).

Moreover, according to the vector constructs of the invention, at least 10 of the functional V genes present in the vector are substantially in their natural configuration. In other words, the construct of the invention comprises at least 10 functional human V genes in substantially unrearranged natural configuration. In one embodiment, the construct of the invention comprises at least 10 functional human V genes in unrearranged natural configuration. In one embodiment, the term natural configuration refers to the gene order and/or DNA sequence. Thus, in one embodiment, at least 10 functional human V genes of the human V genes which are comprised in the vector of the invention are in the same sequential order in which they can be found in the human germline. In other words, the construct of the invention comprises at least 10 functional human V genes in unrearranged order. In one embodiment, the vector comprises 10 functional human V genes in unrearranged order. In one embodiment, the vector comprises more than 10 functional human V genes and 10 of these are in unrearranged order. In one embodiment, the vector comprises more than 10 functional human V genes wherein all are in unrearranged order. The invention thus excludes combining at least 10 different functional human V genes where V genes are selected and combined so that they are no longer in their natural order.

The at least 10 V genes in their natural order also comprise intervening sequences.

Furthermore, the sequences of at least 10 functional human V genes and their intervening regions are substantially as can be found in the human germline. For example, the sequence shows at least 90%, 91%, 92%, 93%, 94%, 95%, 96%, 97%, 98% or 99% sequence identity to the sequence as can be found in the human germline. The intervening regions are important as they influence access to V genes and determine how they are used to generate the antibody repertoire. As a skilled person would appreciate, small differences in the sequence may occur due to recombination events in yeast during the process for constructing vector constructs of the invention.

Preferably therefore, according to the invention, at least 10 functional human V genes used in the constructs of the invention are not modified by targeted manipulations to remove or alter one or more intervening sequences that are located between functional V genes. Such targeted manipulations exclude small differences in the sequence due to recombination events in yeast during the process for constructing vector constructs of the invention. Thus, the construct of the invention comprises at least 10 functional human V genes in substantially native sequence.

Furthermore, preferably, the V genes are not engineered to alter residues to increase solubility. In other words, the V genes are naturally occurring.

Specific combinations of functional human V genes used in a vector, for example a YAC, of the invention are shown in the examples. However, there is no requirement for any specific combinations of V genes and any functional human V gene may be used for productive expression of a HCAb provided that at least 10 functional human V genes comprised in the vector are in the same order in which they can be found in the human germline.

As described above, the vector includes human heavy chain D and J genes. Thus, at least one, preferably more, human heavy chain D gene and at least one, preferably more, human J gene is present in the constructs of the invention. In one embodiment, the construct includes 1-19, for example at least 5, at least 10, at least 15 or more human heavy chain D genes. In one embodiment, the construct includes at least 5, at least 10, at least 15 or more human heavy chain J genes. In one embodiment, the construct includes 1, 2, 3, 4, 5, 6, 7, 8, 9, 10, 11, 12, 13, 14, 15, 16, 17, 18 or 19 human heavy chain J and D genes. In one embodiment, the construct of the invention includes all human heavy chain D genes. In one embodiment, the construct of the invention includes all human heavy chain J genes. In another embodiment, the human heavy chain D and J genes are substantially in their natural configuration. In one embodiment, the human heavy chain D and J genes are in the same order in which they can be found in the human germline. Preferably therefore, according to the invention, the D and J genes used in the constructs of the invention are not modified by targeted manipulation to remove or alter one or more intervening sequences.

In one embodiment, the vector constructs of the invention also include a murine enhancer, a major regulator of IgH gene transcription and VDJ recombination, and a murine switch μ element. A switch element is essential for class switching.

In one embodiment, the vector further comprises at least one or more murine C region gene. In one embodiment, the C region gene is selected from Cγ1, Cγ2b and/or Cγ2a. In one embodiment, the vector comprises Cγ1, Cγ2b and Cγ2a.

The vector constructs of the invention thus includes a mouse Cγ1 gene which lacks the $C_H1$ exon. The vector constructs may however also comprise additional C genes or regions.

Furthermore, in one embodiment, the vector includes a murine 3' enhancer region. Preferably, this is a region which is about 42 kb in size. In one embodiment, this region comprises enhancer elements hs3A, hs1.2, hs3B, hs4 and a predicted insulator region containing elements hs5, hs6 and hs7 (Garrett et al., 2005; Chatterjee et al., 2011). As shown in the examples, this is a region which is about 42 kb in size containing multiple DNase I hypersensitive (hs) sites indicative of the existence of regulatory elements. A 3' enhancer was shown to be essential in the class switch recombination process during B cell development and in IgH expression (Lieberson et al, 1995; Vincent-Fabert et al., 2010). A 747 bp region in rat 3' enhancer was identified possessing enhancer activity through an in vitro assay by measuring the transcription of human δ-globin gene (Pettersson et al., 1990). Mice with targeted deletions of each of the individual enhancer elements hs3A, hs1.2, hs3B and hs4 were indistinguishable in class switch from wild type controls (Cogne et al., 1994; Manis et la., 1998; Zhang et al., 2007; Vincent-Fabert et al., 2009; Bebin et al, 2010). However, a combined deletion of all four hs elements eliminated class switch to all isotypes (Vincent-Fabert et al., 2010).

The insulator regions are predicted to isolate the IgH locus from non-IgH genes located downstream or elsewhere (Chatterjee et al., 2011). Hence, including a full size 3' enhancer in the YAC constructs of the invention provides a source of all the enhancer elements with redundant and synergic roles as well as the insulator for protecting the rest of the genomic locus.

The vector may further comprise marker genes, for example yeast marker genes TRP1, HIS3 and/or ADE2, and/or a Hygromycin resistant gene. Additional selection markers may be included.

Vector constructs according to the invention with 10 or more functional human V genes can be generated in vitro or in vivo as shown in the examples. For generation in vivo, for example YAC1 as shown in FIG. 10 is introduced in mouse ES cells and the number of V genes is extended by targeted gene knock-in in ES cells. Briefly, targeting vectors with the added V genes, together with a region of homology with the existing transgene are used to extend the transgene via a homologous recombination event.

ES cells containing a vector of the invention as a vector transgene can be obtained either by direct introduction of the vector DNA into ES cells by transfection, or by derivation of ES cells from a mouse carrying a transgene. Re-derived ES cells will carry the transgene in the same copy number and the same genomic location as the mouse, whereas transfected cells may have variant copy number and may integrate anywhere in the mouse genome, unless specifically targeted.

The YAC or other vector according to the invention can be introduced into a mouse cell or mouse for the production of HCAb or fragments thereof as a transgene. Thus, the invention also relates to the use of the vector as described herein in a method for the production of HCAb. As explained below, $V_H$ binding domains that are soluble, do not aggregate and are substantially monomeric can be produced in the mouse as detailed below. The invention also relates to the use of the vector as described herein in generating a mouse which produces HCAb and in generating VH domains from said mouse.

In another aspect, the invention provides a transgenic mouse, or transgenic murine host cell transformed with a vector of the invention and as described herein and thus expressing a heterologous heavy chain locus. Thus, in one aspect, the invention relates to a transgenic mouse transformed with a YAC or other vector comprising a) at least 10 functional human heavy chain V genes wherein at least 10 functional human heavy chain V genes are in their natural configuration;

b) at least one human heavy chain D gene and at least one human heavy chain J gene;

c) a murine μ enhancer and switch μ element or switch γ element;

d) a murine C gene which lacks the $C_H1$ exon and e) a murine 3' enhancer element.

The murine 3' enhancer element is as elsewhere described. Other features of the vector are also described elsewhere. In one embodiment, said vector is a YAC.

In one embodiment, said a murine C gene is a murine Cγ1 gene. In one embodiment, said murine 3' enhancer element comprises enhancer elements hs3A, hs1.2, hs3B, hs4, hs5, hs6 and hs7. Thus, in one embodiment, the invention relates to a transgenic mouse or murine host cell transformed with a YAC comprising a) at least 10 functional human heavy chain V genes wherein at least 10 functional human heavy chain V genes are substantially in their natural configuration;
b) at least one human heavy chain D gene and at least one human heavy chain J gene;
c) a murine μ enhancer and switch μ element or switch γ element;
d) a murine Cγ1 gene which lacks the $C_H1$ exon and
e) a murine 3' enhancer element comprising enhancer elements hs3A, hs1.2, hs3B, hs4, hs5, hs6 and hs7.

In one embodiment, the host cell is a murine host cell. In one embodiment, the transgenic mouse has a reduced capacity to express endogenous antibody genes. Thus, in one embodiment, the mouse has a reduced capacity to express endogenous light and/or heavy chain antibody genes. The mouse may therefore comprise additional modifications to disrupt expression of endogenous light and/or heavy chain antibody genes so that no functional light and/or heavy chains are produced.

In one embodiment, the mouse may comprise a non-functional lambda light chain locus. Thus, the mouse does not make a functional endogenous lambda light chain. In one embodiment, the lambda light chain locus is deleted in part or completely or rendered non-functional through insertion. For example, at least the constant region genes C1, C2 and C3 may be deleted or rendered non-functional through insertion. In one embodiment, the locus is functionally silenced so that mouse does not make a functional lambda light chain.

Furthermore, the mouse may comprise a non-functional kappa light chain locus. Thus, the mouse does not make a functional endogenous kappa light chain. In one embodiment, the kappa light chain locus is deleted in part or completely or rendered non-functional through insertion. In one embodiment, the locus is functionally silenced so that the mouse does not make a functional kappa light chain.

The mouse having functionally silenced endogenous lambda and kappa L-chain loci may, for example, be made as disclosed in WO2003/000737, which is hereby incorporated by reference in its entirety.

Furthermore, the mouse may comprise a non-functional heavy chain locus. Thus, the mouse does not make a functional endogenous heavy chain. In one embodiment, the heavy chain locus is deleted in part or completely or rendered non-functional through insertion. In one embodiment, the locus is functionally silenced so that the mouse does not make a functional heavy chain.

For example, as described in WO2004/076618, all 8 endogenous heavy chain constant region immunoglobulin genes (μ, δ, γ3, γ1, γ2a, γ2b, ε and α) are absent in the mouse, or partially absent to the extent that they are non-functional, or genes δ, γ3, γ1, γ2a, γ2b and ε are absent and the flanking genes μ and α are partially absent to the extent that they are rendered non-functional, or genes μ, δ, γ3, γ1, γ2a, γ2b and ε are absent and α is partially absent to the extent that it is rendered non-functional, or δ, γ3, γ1, γ2a, γ2b, ε and α are absent and μ is partially absent to the extent that it is rendered non-functional. WO2004/076618 is hereby incorporated by reference in its entirety.

By deletion in part is meant that the endogenous locus gene sequence has been deleted or disrupted, for example by an insertion, to the extent that no functional endogenous gene product is encoded by the locus, i.e. that no functional product is expressed from the locus. In another embodiment, the locus is functionally silenced.

In one embodiment, the mouse which expresses a vector of the invention comprises a non-functional heavy chain locus, a non-functional lambda light chain locus and a non-functional kappa light chain locus. The mouse therefore does not produce any functional endogenous light or heavy chains. Thus, the mouse is a triple knockout (TKO) mouse.

Transgenic mice can be created according to standard techniques as illustrated in the examples (see FIG. 13). The two most characterised routes for creating transgenic mice are via pronuclear microinjection of genetic material into freshly fertilised oocytes or via the introduction of stably transfected embryonic stem cells into morula or blastocyst stage embryos.

ES cell lines bearing the transgene are generated in vitro or derived from embryos of transgenic mice. New features may be introduced into the transgene by homologous recombination or by use of insertion vectors. Constructs are introduced to the ES cells using (for example) lipofection, electroporation or other methods known in the art. Clones bearing the selectable resistance marker are picked and screened for successful integration. Both the constructs and the ES cells may be modified with molecular features to assist with both the integration of desired constructs and the screening and selection of correctly targeted ES clones.

Transgene engineering may include one or more of the following features, all of which are known in the art:
  Selection markers: Bsd, Zeo, Puro, Hyg which may be used in any combination
  Negative selectable marker: thymidine kinase (TK). Negative selection may be used in combination with one or more selection markers
  Markers and/or vector sequence may be flanked with loxP, variant loxP, Frt or variant Frt sites. Pairs of sites may be identical or non-identical. More than two sites may be used.
  Use of recombinases (Cre, Flp) to delete, invert or replace sequences
  Generation of genomic double stranded break at defined sequences, for example via:
    Zinc fingers
    TALENs
    CRISPR
    Mega nucleases (homing endonucleases)

A targeted build-on may be achieved in one or multiple steps. Sequence may be inserted via homologous recombination and a selectable marker removed by subsequent recombinase-mediated deletion. Alternatively a first modification step might introduce features such as recombinase recognition sites and optionally a negative selectable marker, which could be used to introduce sequence via recombination mediated cassette exchange.

Strategies used for a targeted build-on may include replacement vectors, insertion vectors or recombination mediated cassette exchange (RMCE). DNA may be introduced and/or deleted at each step. Introduced DNA may be human, bacterial, yeast or viral in origin. DNA may be introduced at any location within the transgene. Transgene engineering may make use of surrounding genomic sequences.

The targeted build will result in a transgenic locus in which the V, D and J genes are in the same order and spacing as in the native human IgH locus, and in which the C regions are as in the native mouse locus. Polymorphisms, including minimal changes brought about by recombineering (such as scars or small deletions), may result.

Regardless of how the genetic material is introduced, the manipulated embryos are transferred to pseudo-pregnant female recipients where pregnancy continues and candidate transgenic pups are born.

The main differences between these broad methods are that ES clones can be screened extensively before their use to create a transgenic animal. In addition, the transgene can be integrated into ES cells at a defined location, or integrate at random. In contrast, pronuclear microinjection relies on the genetic material integrating to the host genome after its introduction and, generally speaking, the successful incorporation and function of the transgene cannot be confirmed until after pups are born.

There are many methods known in the art to both assist with and determine whether successful integration of transgenes occurs. Transgenic animals can be generated by multiple means including random integration of the construct into the genome, site-specific integration, or homologous recombination. There are various tools and techniques that can be used to both drive and select for transgene integration and subsequent modification including the use of drug resistance markers (positive selection), recombinases, recombination mediated cassette exchange, negative selection techniques, and nucleases to improve the efficiency of recombination. Most of these methods are commonly used in the modification of ES cells. However, some of the techniques may have utility for enhancing transgenesis mediated via pronuclear injection.

Further refinements can be used to give more efficient generation of the transgenic line within the desired background. As described above, in preferred embodiments, the endogenous mouse immunoglobulin expression is silenced to only allow expression of HCAb for drug discovery. Genetically-manipulated mice, for example TKO mice that are silenced for all endogenous immunoglobulin loci (mouse heavy chain, mouse kappa chain and mouse lambda chain) can be used as described above. The transfer of any introduced transgene to this TKO background can be achieved via breeding, (either conventional or with the inclusion of an IVF step to give efficient scaling of the process). However, it is also possible to include the TKO background during the transgenesis procedure. For example, for microinjection, the oocytes may be derived from TKO donors. Similarly, we have also derived ES cells from TKO embryos (see below) for use in transgenesis. Furthermore, as mentioned above, since the YAC1 is a common core structure present in alternative constructs (described in FIG. 10), ES cells derived from YAC1 transgenic mice may be used for targeted additions to give rise to a transgene with the same features as those in the YAC2, 3 or other YACS with a core YAC1 design. The various transgenesis options are summarised in FIG. 13.

A further aspect of the invention is the use of a mouse as described herein which expresses a vector of the invention in the production of an HCAb lacking a functional $C_H1$ domain. This is preferably a triple knockout mouse as described herein. In one embodiment, the HCAb may be a chimeric antibody, for example including sequences derived from a rodent and human. In another embodiment, the mouse of the invention is used in a method for producing soluble $V_H$ domains. Thus, soluble $V_H$ binding domains can be produced using the mouse of the invention.

The mouse of the invention can also be used in constructing libraries, such as in vitro display libraries. This is illustrated in the non-limiting examples. In one embodiment, the mouse of the invention is used to construct naïve libraries. Thus, the invention relates to the use of a mouse of the invention in constructing libraries. In one embodiment, the library is a naïve library. In one embodiment, immunisation is ex vivo.

Also provided is a method for generating a murine cell or mouse producing a HCAb comprising introducing a vector as described herein into a mouse. Preferably, said mouse comprises a non-functional heavy chain locus, a non-functional lambda light chain locus and a non-functional kappa light chain locus. In one embodiment, said method comprises generating a naïve library from said mouse. In another embodiment, said mouse is immunised, for example by ex vivo immunisation.

Also provided by the invention is a method for obtaining a HCAb or fragment thereof, for example a $V_H$ domain, from a mouse, comprising the steps of:

(i) introducing a vector of the invention, for example a YAC;

(ii) allowing formation in the mouse of a HCAb or antigen binding molecule lacking a functional $C_H1$ domain; and (iii) obtaining the HCAb or antigen binding molecule from mouse serum.

Preferably, said mouse comprises a non-functional heavy chain locus, a non-functional lambda light chain locus and a non-functional kappa light chain locus.

The V, D and J gene segments, when expressed in the mouse, are capable of recombining to form a VDJ coding sequence. Also, the heterologous locus, when expressed in the mouse, is capable of forming functional immunoglobulin molecules of any class whose constant gene is included in the vector introduced into a mouse. The class of antibody will be dictated by the C genes present in the construct. Thus, the antibody isotype is selected from IgG, IgA, IgD, IgE or IgM or mixtures thereof. Preferably, the isotype is IgG. IgG may be selected from any subclass. Thus, the invention provides a way of efficient engineering of class-specific HCAb and single domain antibodies, in particular soluble $V_H$ domains.

Also provided by the invention is an isolated HCAb-producing or $V_H$ domain-producing cell obtained or obtainable using the method of the invention. Selection and isolation of the cell may employ flow-cytometry or other cell isolation process, for example for the identification and isolation of $B220^{int/+}$, syndecan$^+$ spleen-derived plasma cells in which an antigen-specific HCAb lacking a functional $C_H1$ domain is produced. However, a skilled person would know that production is not limited to these types of B cells or methods.

The antibody-producing cell of this aspect of the invention may be isolated from a secondary lymphoid organ. For example, the secondary lymphoid organ may be a non-splenic organ, for example any of the group consisting of: lymph node, tonsil, and mucosa-associated lymphoid tissue (MALT), including gut-associated lymphoid tissue (GALT), bronchus-associated lymphoid tissue (BALT), nose-associated lymphoid tissue (NALT), larynx-associated lymphoid tissue (LALT), skin-associated lymphoid tissue (SALT), vascular-associated lymphoid tissue (VALT), and/or conjunctiva-associated lymphoid tissue (CALT). In one embodiment, the antibody-producing cell is a peritoneal cell. In one embodiment, the antibody-producing cell of this aspect of the invention may be isolated from bone marrow.

The mouse of the invention provides a HCAb lacking a functional $C_H1$ domain or a $V_H$ domain. The antibody of the invention may be in an isolated and purified form. The antibody may be isolated and/or characterised using methods well known in the art.

Once characterised, the HCAb or $V_H$ domain may be manufactured using recombinant or synthetic methods, also well known in the art. For applicable prior art methods, see references listed below.

The transgenic mouse according to the invention carries a repertoire of heavy chain B cells comprising HCAb that can be exploited to generate isolated human $V_H$ domains against therapeutic targets. Such $V_H$ domains may be isolated in a number of ways. For example, populations of lymphoid cells containing B cells can be extracted from various lymphoid sources from the transgenic mouse and may even be selected or stimulated in vitro prior to the identification of target-specific $V_H$. Libraries may be constructed from cloned ex-vivo transcripts and interrogated for antigen binding domains using various in vitro display platforms including, but not limited to, phage and ribosome display. Such libraries can be constructed from naive mice or from immunised animals containing an affinity-matured immune repertoire reactive to a particular target antigen.

Production of the HCAb according the methods of the invention may include expression from an antibody-producing cell, either by expression on the cell surface or by secretion (i.e. release of antibody from the cell).

The HCAb or $V_H$ domain may preferably be produced in a mouse at physiological levels. In one embodiment, the HCAb or $V_H$ domain may be produced at levels that are higher than in the wild type. As shown in FIG. 20, free HCAb can be produced in the serum of triple knockout mouse, when the transgene has been introduced.

Moreover, as shown in the examples, the HCAb or $V_H$ domain produced according to the methods of the invention is soluble and stable.

The HCAb or $V_H$ domain may be modified to increase solubility, for example by genetic engineering of one or more genes encoding the antibody.

Thus, the invention also relates to a method for producing soluble $V_H$ domains using the mouse of the invention. The $V_H$ domains are soluble, do not aggregate, have high thermostability and affinity. In one embodiment, the method for producing soluble $V_H$ domains comprises the following steps:
a) expressing a vector of the invention in a transgenic mouse,
b) isolating a cell or tissue expressing a HCAb,
c) cloning the sequence encoding the $V_H$ domain from mRNA derived from the isolated cell or tissue,
d) constructing a library from cloned transcripts and
e) isolating the $V_H$ domain.

As explained elsewhere, the mouse is preferably a triple knockout mouse that does not produce any functional endogenous light or heavy chains.

The libraries constructed can be used in display selection techniques for isolation of the $V_H$ domain. Display selection techniques include phage display, yeast or ribosome display.

In an additional step, the $V_H$ domain may be expressed in an expression system, for example a microbial or mammalian expression system.

In an additional step, $V_H$ domains can be assayed for affinity. This may be carried out by a number of techniques known in the art including but not limited to ELISA and BIAcore. In addition, binding to cell surface antigens can be measured by fluorescence activated cell sorting (FACS). The affinity of the isolated $V_H$ domain for target antigen is a crucial parameter in determining whether a candidate $V_H$ domain is likely to proceed further into development as a therapeutic candidate. Affinity is commonly measured by the dissociation constant $K_d$ ($K_d$=[antibody][antigen]/[antibody/antigen complex]) in molar (M) units. A high $K_d$ value represents an antibody which has a relatively low affinity for a target antigen. Conversely a low $K_d$, often in the sub-nanomolar (nM) range indicates a high affinity antibody.

In addition to strength of binding to target antigen, the ability of a $V_H$ to influence the function of a given target may also be assayed.

In one embodiment, the method also includes the step of immunising animals with a target antigen to elicit an immune response, the immune response comprising antigen-specific antibody production. However, libraries can also be constructed from naïve animals.

A variety of immunisation protocols may be used to drive HCAb responses within the transgenic animals. The most commonly used procedures rely on administering protein-based targets in conjunction with an adjuvant. The targets are often in purified form but crude antigen preparations may also be used. Cells can also be used as a source of antigen, where the desired target is expressed by the cell either naturally or as a result of genetic manipulations. DNA may also be used as a source of immunogen. In this case, an expression plasmid combined with molecular or cytokine adjuvant is often used with in-vivo transfection giving rise to the protein immunogen. During and following immunisation, HCAb responses can be monitored by applying (for example) a serum-ELISA or ELISpot technique.

In addition to library-based discovery methods, hybridoma technology may be used where ex-vivo B cells (within a lymphoid population or pre-selected) are fused with a partner myeloma cell to create monoclonal hybridomas producing HCAb that can be screened for the desired binding properties. $V_H$ sequences can then be cloned from the hybridomas and converted into the desired final format.

Thus, in another aspect, the invention also relates to a method for producing soluble $V_H$ domains comprising the following steps:
a) expressing a vector of the invention in a transgenic mouse,
b) isolating a cell or tissue expressing a HCAb,
c) producing a hybridoma from said cell,
d) isolating the $V_H$ domain.

Further provided according to the invention is a hybridoma obtainable by fusion of a HCAb-producing cell or $V_H$ domain producing cell as defined herein with a B-cell tumour line cell. In certain embodiments of the invention the antibody-producing cell used to form the hybridoma is a non-splenic secondary lymphoid organ cell (see above). Well known methods of generating and selecting single clone hybridomas for the production of monoclonal antibodies may be adapted for use in the present invention.

Also provided according to the invention are HCAb, antibodies derived therefore or fragments thereof obtained or obtainable by the methods described herein.

Accordingly, the invention provides a HCAb made in a mouse, or a fragment thereof obtained or derived from a mouse which expresses a vector of the invention. In one embodiment, the fragment derived from the mouse of the invention, preferably a transgenic TKO mouse, is a $V_H$ domain.

The HCAb or $V_H$ domain may be specific to an antigen. The HCAb or $V_H$ domain may be engineered to be a bi- or multi-valent antibody with one or more specificities.

The HCAb may be a monoclonal antibody, an IgG-like antibody or an IgM-like antibody. The HCAb or $V_H$ domain produced by the methods and mouse of the invention may be used as a diagnostic, prognostic or therapeutic imaging agent. The HCAb or $V_H$ domain may additionally or alternatively be used as an intracellular binding agent, or an abzyme.

Also provided is a medicament, pharmaceutical formulation or composition comprising a HCAb or $V_H$ domain as described herein and optionally a pharmaceutically acceptable carrier. The medicament will typically be formulated using well-known methods prior to administration into a patient. Thus, the invention relates to a composition comprising a $V_H$ domain obtained or obtainable by the method of the invention. The composition comprises the $V_H$ domain alone or in combination with another $V_H$ domain, protein, or other molecule of therapeutic benefit. Non-limiting examples are listed below.

In one embodiment, conjugation may be to a toxic moiety (payload) to form an antibody drug conjugate (ADC) or to a radionuclide to form a radioimmunoconjugate with the aim of utilising the binding of the human $V_H$ domain, to its target antigen in vivo to deliver the toxic moiety to an extracellular or intracellular location. The $V_H$ domain therefore guides the toxic payload to the target cell (which may be a cancer cell) where the payload can unfold its cytotoxic activity and kill the cell. The toxic moiety may be fused directly to the $V_H$ domain. In another example, the toxic moiety may be coupled chemically to the $V_H$ domain either directly or via a linker. The linker may comprise a peptide, an oligopeptide, or polypeptide, any of which may comprise natural or unnatural amino acids. In another example, the linker may comprise a synthetic linker. The linker may be cleavable or not cleavable. Typically, linkers are attached to the antigen binding molecule via the amino groups of lysine residues, or by the thiol groups on cysteine residues. A number of linkers are known to the skilled person, these are, for example, described in Ducry et al, Bioconjugate Chem. 2010, 21, 5-13 and WO 2004/01095. Both references are incorporated herein by reference. In another embodiment, the $V_H$ domain is fused with an Fc region or part thereof.

In one embodiment of the composition, at least two $V_H$ domains are fused together in line or coupled or conjugated by methods known in the art. The $V_H$ domains may bind to the same target antigen or different antigens.

The $V_H$ domain may thus be for use as a medicament in the treatment of a disease. Thus, the invention relates to methods of treating a medical condition comprising administering a $V_H$ domain of the invention to a patient in need thereof.

Diseases which are susceptible to treatment using an antibody according to the invention include but are not limited to: wound healing, cell proliferative disorders, including neoplasm, melanoma, lung, colorectal, osteosarcoma, rectal, ovarian, sarcoma, cervical, oesophageal, breast, pancreas, bladder, head and neck and other solid tumors; myeloproliferative disorders, such as leukemia, non-Hodgkin lymphoma, leukopenia, thrombocytopenia, angiogenesis disorder, Kaposi' sarcoma; autoimmune/inflammatory disorders, including allergy, inflammatory bowel disease, arthritis, psoriasis and respiratory tract inflammation, asthma, immunodisorders and organ transplant rejection; cardiovascular and vascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection, pathological conditions associated with the placenta and other pathological conditions. Suitable administration routes are known to the skilled person.

Furthermore, the invention relates to a HCAb lacking a functional $C_H1$ domain comprising human $V_H$ and mouse constant regions.

The invention includes vector constructs as herein before described with reference to one or more of the drawings. In one aspect, the invention relates to a vector as shown in FIG. 10.

No doubt many other effective alternatives will occur to the skilled person. It will be understood that the invention is not limited to the described embodiments and encompasses modifications apparent to those skilled in the art and lying within the spirit and scope of the claims appended hereto.

All documents and publications mentioned herein are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The invention is further described in the following non-limiting examples.

EXAMPLES

Example 1: Construction of YACs 1.1 Materials
Vectors:
pYAC3 (from Bruschi, ICGEB, Yeast Molecular Genetics Group, Trieste, ITALY)
pYNOT (derived from pYAC3 by replacing the URA3 with LEU2 marker. From Bruschi, ICGEB, Yeast Molecular Genetics Group, Trieste, ITALY)
pHTK (derived from pYNOT by replacing the LEU2 with HIS3 marker)
pHKT-Hy (a hygromycin (Hy) resistant gene inserted into pHKT)
pYES1L (Invitrogen)
Yeast Strains:
YLBW1 (Hamer et al., 1995), AB1380 (Markie, 2006).
1.2 Convert BACs to YACs
BACs (bacterial artificial chromosomes in a circular format) are tools well known in the art that facilitate the manipulation (e.g. sequencing and cloning) of segments of DNA from ~150 kbp-350 kbp in size (*Methods in Molecular Biology*, Volume 54 and 349).

BACs containing DNA derived from the heavy chain immunoglobulin locus of humans or mice are numerous and well known in the art. Examples of such BACs (also listed in FIGS. 1 and 2) include but are not limited to:
Human:
RP11-1065N8
RP11-659B19
RP11-14117
RP11-72N10
RP11-683L4
RP11-12F16
Murine:
RP23-354L16
RP24-72M1
It is also well known in the art that BACs can be used to facilitate the sequential molecular joining of multiple DNA segments comprising overlapping (complementary)

sequence to create much larger DNA molecules. One such method for achieving this, BIT (bridge induced translocation), required that BACs must first be converted into a non-overlapping linear format in yeast as yeast artificial chromosomes (YACs).

BAC Conversion by Transformation-Associated Recombination (TAR) Cloning

BAC conversion and YAC manipulations are well established techniques described in the art for example in YAC Protocols (*Methods in Molecular Biology*, Volume 54 and 349), in which the recipes and methods for auxotrophic markers, yeast selection, media, yeast transformation, YAC screening, YAC transferring, YAC modification and amplification are described in detail.

Briefly, two anchor sequences anchor 1 (a1) and anchor 2 (a2) flanking the non-overlapping sequence to be retained from the BAC for subsequent joining were amplified by PCR with engineered restriction sites (SalI and SphI) at the end of the PCR primers for cloning into pYAC3 (edu/vectordb/vector_descrip/COMPLETE/PYAC3.SEQ.html) vector (FIG. 3). The design requirements for such anchor sequences are well known in the art (e.g. Alasdair MacKenzie, 2006, YAC protocols, $2^{nd}$ Edition). Restriction enzyme digested a1 and a2 were sequentially cloned into pYAC3 (FIG. 3). The pYAC3-a1-a2 vector was subsequently digested with SphI and BamHI generating two YAC arms, a1-URA3-telomere and a2-centromere-TRP1-telomere. Yeast carrying the original BAC was transformed with these two YAC arms, plated on yeast medium with tryptophan and uracil drop out and incubated at 30° C. for three days. Homologous recombination between the YAC arms and the BAC at the position of the anchors produced the converted YAC (FIG. 4). Transformants were screened for the right converted product by PCR of the joints and by pulse field gel electrophoresis (PFGE) for the size. Non-overlapping YACs comprising adjacent DNA sequence to be joined were subsequently assembled by BIT.

Joining Two Non-Overlapping YACs by BIT

A kanamycin resistance gene $KAN^R$ cassette was built by adding to each end an FRT site and a 65 bp fragment of YAC homologous sequence specific to the two YAC ends for joining (FIG. 5). This cassette was transformed into yeast containing the two YACs to be joined. Kanamycin resistant clones were further characterized by PCR and Southern blot to confirm the successful joining. The $KAN^R$ gene was then popped out using FLP recombinase. The DNA at the joint region was sequenced and confirmed the existence of a DNA 'scar' containing the FRT sequence at the joining site. At each step of the YAC manipulation, PFGE was applied to confirm YAC size. Sequential joining of YACs comprising adjacent sequence from the original human immunoglobulin heavy chain locus was used to generate a number of YAC constructs each with human C-, D- and J-genes and increasing numbers of V-genes.

1.3 C Region Construction with Mouse Elements

In order to enhance the efficiency of the immune response driven from the YAC constructs, they were each subsequently modified to replace the human C-region genes with elements of the murine heavy chain constant region.

Utilising the ability of yeast to take up and efficiently recombine overlapping DNA fragments (Gibson et al, 2008), multiple overlapping fragments were used to add the murine µ enhancer, murine µ switch and the murine constant γ1 gene (the latter with the CH1 domain deleted) to the 3' end of the last human J gene, in order to create YAC constructs with a single constant gene. Subsequently, a similar approach was adopted to create a YAC construct comprising multiple murine constant genes Cγ1, Cγ2b and Cγ2a all with deleted $C_H1$ domains.

1.3.1 YAC with a Single Murine C-Gene

Preparing DNA Fragments for Yeast Transformation

The Mouse µ Enhancer and Switch µ Element

Forward Primer:

GACATTCTGCCATTGTGATTACTACTACTACTACGGTATGGACGTCTGGGGGCAA GGGACCACGGTCACCGTCTCCTCAGGTAAGAAT (SEQ ID NO. 1). The first 69 bp of this primer is from the human J6 (ID: J00256, imgt.org/IMGTIect/?query=201+J00256).

The last 24 bp of this primer is complementary to the mouse sequence 3' to the J4. Reverse primer: TTGAGGACCAGAGAGGGATAAAAGAGAAATG (SEQ ID NO. 2), this primer is reverse complementary to the region 5' to the mouse IGHµ $C_H1$ (FIG. 6). PCR with these two primers using BAC RP23-354L16 as template generated a 5.8 kb fragment covering the mouse µ enhancer and µ switch region with one end homologous to human J6 region.

The Mouse Cγ1 Gene with Deleted $C_H1$

Forward primer: AGAGGACGTATAGGGAGGAGGGGTTC (SEQ ID NO. 3); Reverse primer: AACACCTTCAGCGATGCAGAC (SEQ ID NO. 4). The 7.8 kb PCR product with these two primers using BAC RP23-354L16 as template covers the whole mouse Cγ1 transcribed region except for the $C_H1$ exon (FIG. 7).

The Linkers Bridging the Non-Overlapping Eµ, Cγ1 and YAC Arm Fragments

Linker 1 for Eµ and Cγ1 fragments: TCATGCCCCTAGAGTTGGCTGAAGGGCCAGATCCACCTACTCTAGAGGCATCTCT CCCTGTCTGTGAAGGCTTCCAAAGTCACGTTCCTGTGGCTAGAAGGCAGCTCCAT AGCCCTGCTGCAGTTTCGTCCTGTATACCAGGTTCACCTACTACCATATCTAGCCC TGCCTGCCTTAAGAGTAGCAACAAGGAAATAGCAGGGTGTAGAGGGATCTCCTGT CTGACAGGAGGCAAGAAGACAGATTCTTACCCCTCCATTTCTCTTTTATCCCTCTC TGGTCCTCAGAAGAGGACGTATAGGGAGGAGGGGTTCACTAGAGGTGAGGCTCA AGCCATTAGCCTGCCTAAACCAACCAGGCTGGACAGCCATCACCAGGAAATGGAT CTCAGCCCAGAAGATCGAAAGTTGTTCTTCTCCCTTCTGGAGATTTCTATGTCCTT TACACTCATTGGTTAATATCCTGGGTTGGATTCCCACACATCTTGACAAACAGAGA CAATTGAGTATCACCAGCCAAAAGTCATACCCAAAAACAGCCTGGCAT (SEQ ID NO. 5). To make linker 1, PCR1 (313 bp, primer1 F: TCATGCCCCTAGAGTTGGCTG; primer1 R: GAACCCCTCCTCCCTATACGTCCTCTTTGAGGACCAGAGAGGGATAAAAGAGAAA TG (SEQ ID NO. 6)) and PCR2 (258 bp, primer2 F: AGAGGACGTATAGGGAGGAGGGGTTC (SEQ ID NO. 7); primer2 R:ATGCCAGGCTGTTTTTGGGTA (SEQ ID NO. 8)) were synthesized using BAC RP23-354L16 as template. PCR1 and PCR2 with overlapping sequences were assembled to Linker 1 by fusion PCR using primer1 F and primer2 R.

Linker 2 for Cγ1 and YAC arm fragments:

(SEQ ID NO. 9)
TACATCTTTTTTCCTCTCTGTCTGCATCGCTGAAGGTGTTTCGTCGCCGC ACTTATGACT GTCTTCTTTA TCATGCAACT

YAC Arm

A 5.7 kb YAC arm with LEU2 gene marker was generated by digestion of pYNOT vector (FIG. 8, derived from pYAC3 by replacing the URA3 with LEU2 marker) with PshAI and BamHI restriction enzymes.

Replacement of human C-region with mouse C-region by yeast homologous recombination Using yeast spheroplast transformation (Sanchez and Lanzer, 2006) 5 fragments (murine Eμ, murine Cγ1, YAC arm, linker 1 and linker 2) were introduced into yeast YLBW1 strain carrying the YAC comprising a human C-region. Transformants were selected on tryptophan and leucine drop out medium. Homologous recombination between the overlapping sequence at human J6 resulted in the replacement of the human genes with mouse Eμ and Cγ1. The new YAC was characterized by PCR and sequencing of the joining sites.

Add 3' Enhancer

Cloning 42 kb 3' Enhancer Fragment into BAC-YAC Vector

Mouse 3' enhancer contains elements hs3A, hs1.2, hs3B, hs4, hs5, hs6 and hs7 scattered in a 42 kb region 3' to the last constant gene Cα. To add the whole enhancer to a site 3' of the Cγ1 gene, a 42 kb MfeI fragment covering all of the enhancer elements was subcloned into a BAC-YAC vector pYES1L (Invitrogen) following the instructions provided by invitrogen. The construct was fully characterized by PCR, PFGE and sequencing. MfeI digestion released the 42 kb fragment from the vector for subsequent yeast transformation.

Preparing the Hygromycin-HIS3 YAC Arm

A YAC vector (pHKT-Hy, FIG. 9) was constructed by insertion of a hygromycin (Hy) resistant gene into pHKT (derived from pYNOT by replacing the LEU2 with HIS3 marker). Double digestion of this vector with SpeI and BamHI generated a 6.2 kb YAC arm fragment containing Hy-HIS3-telomere.

The Linkers Bridging the 3' Enhancer Fragment to the Mouse Cγ1 Gene and the Hy-HIS3 YAC Arm Linker 1 (626 bp) for mouse Cγ1 and 42 kb 3' enhancer ACGGCTCAGGAGGAAAAGGCACTCTGTGTG-GAGCTCTTCAGTGGGTATGAAATG GTGATG-GAGAAGCCCAGGTGCACTGAAAATCCAGGAGCT-GAATTTGATCACCAGG
ACGCATATGGTAGAGAGGAAAATGAATTGATTCC-CAAATGTTCTCCTCTATGTGTG CACCGTGG-CATGTGCATGCACACAATTACACATAAACACATT-CAACATAAATACAA
CACACATATACACGCTGCACACACATA-CACACACAGAACACACACCACACACACA CAC-CACACACAATCACACACATATTCCACACAGTACAC-CACAAACATCTATACACA
CCACACACACACAGACACACACACACACATT-CATACACAGCACAACACAAACAT CTATA-CACAACACACACACAATACACATAGTCACACGCAT-ATTCACTCACACACAT
ATTCACCCACACACAATCATACATAGACACATT-CAACATAAACACAACACCACACA
CACACACACTTGCACACACAAATGTAATGAT-TTTTTTAAGGACTACATCTTTTTTCC TCTCTGTCTG-CATCGCTGAAGGTGTTCAATTGCCAAAAT-CACAGGTGAGCCCAGA TGCATACCCGGGAC (SEQ ID NO. 10). To make linker 1, PCR1 (604 bp, primer1 F:ACGGCTCAGGAGGAAAAGGCAC (SEQ ID NO. 11); primer1 R: TCACCTGTGATTTTGGCAATT-GAACACCTTCAGCGATGCAGAC (SEQ ID NO. 12)) was synthesized using BAC RP23-354L16 as templates. Then PCR1 was extended to 626 bp by primer1 F and primer R: GTCCCGGGTATGCATCTGGGCTCACCTGTGAT-TTTGGCAATTG (SEQ ID NO. 13).

Linker 2 (766 bp) for 42 kb 3' enhancer and Hy-HIS3 YAC arm GAGGTACAGGGGGCTCATGGGTT-TATAAGTTCAGGTTTATACCAAGGTTTCGGGG GGTAGCCTGAGGCT-CATGTACCTTCTTGTGGTAGCCCCCAGGTTCTGTG-CATGGT ACTGCTCAGTTACTGGCATGGCTTCTGG-GAAGGCTGGGCTCCCACGTCCCCTGT GGACACATGGTTACGCCAAGAACAGAACTA-CAAAGTTAGGAGTTACCATTCCCAC CTGCACCTGTATCTCCAGTACCTGGGTTTCTAA-GACGTAGTGAGTCCTCTTGCCAA CCAGGGTCTGC-CACAATGGTCAGGCACAGCTGTGGGCCGGTCAGC-CCCATCAGG TCACACCAGCAGGTCCCAG-GAGCACAGAGCT-TAAATGCCCCCTAGTGTCCCTAGT
GAGGCTCCGGTGCCCGTCAGTGGGCAGAGCGCA-CATCGCCCACAGTCCCCGAG AAGTTGGGGG-GAGGGGTCGGCAATT-GAACCGGTGCCTAGAGAAGGTGGCGCGG GGTAAACTGGGAAAGT-GATGTCGTGTACTGGCTCCGCCTTTTTCCCGAGGG-TGGG
GGAGAACCGTATATAAGTGCAGTAGTCGCCGT-GAACGTTCTTTTTCGCAACGGGT
TTGCCGCCAGAACACAGGTAAGTGCCGTGTGTGGT-TCCCGCGGGCCTGGCCTCT TTACGGGT-TATGGCCCTTGCGTGCCTTGAATTACTTC-CACCTGGCTGCAGTACGT GATTCTT-GATCCCGAGCTTCGGGTTGGAAGTGGGTGGGAGA-GTTCGAGGCCTTG CGC (SEQ ID NO. 14). To make linker 2, PCR1 (379 bp, primer1 F:GAGGTA-CAGGGGGCTCATGGGT (SEQ ID NO. 15); primer1 R:AGCCTCACTAG GGACACTAGGGGGCATTTAAGC (SEQ ID NO. 16)) and PCR2 (387 bp, primer2 F:CCCTAGTGTCCCTAGTGAGGCTCCGGTGCCCGT (SEQ ID NO. 17); primer2 R:GCGCAAGGCCTCGAACTCTC (SEQ ID NO. 18)) were synthesized using BAC RP23-354L16 and BAC RP24-72M1as templates, respectively. PCR1 and PCR2 with overlapping sequences were assembled generating Linker 2 by fusion PCR using primer1 F and primer2 R.

Yeast Transformation 4 fragments (3' enhancer, Hy-HIS3-telomere YAC arm, linker 1 and linker 2) were introduced into yeast YLBW1 strain containing YAC for the addition of 3' enhancer by yeast spheroplast transformation. Transformants were selected on tryptophan and histidine drop out medium. Homologous recombination between the overlapping fragments resulted in the addition of the 3' enhancer and Hy-HIS3-telomere arm to the YAC of choice, generating Crescendo YAC1 or YAC2 (FIG. 10). The new YAC was characterized by PCR and sequencing of the joining sites. The size of the new YAC was confirmed by PFGE and southern blotting.

1.3.2 YAC with Multiple Constant Genes

In addition to the YACs containing a mouse Cγ1 gene, other YACs were designed to include multiple constant genes—the mouse constant genes Cγ1, Cγ2b and Cγ2a all with deleted $C_H1$ domain (FIG. 10).

Generating 45 kb Fragment Containing $C_H1$ Deleted Cγ2b and Cγ2a.

Using primers listed below, 7 overlapping PCR fragments were amplified using RP24-72M1 as a template. Fragment 3 was synthesized by fusion PCR with Cγ2b ($C_H1$ deleted); and fragment 6 was synthesized by fusion PCR with Cγ2a ($C_H1$ deleted).

Primers Used for the 7 PCRs:

```
Fragment 1: 45k-1 8057bp
Forward:
                                      (SEQ ID NO. 19)
GGTTGGATTCTATCTTCGCATGG Reverse:
                                      (SEQ ID NO. 20)
TGGGTCCTGTCTTTCTACCTTTG Fragment 2: 45k-2 8304bp
Forward:
                                      (SEQ ID NO. 21)
GCTCCTTGCTGGGTCTTAATGTT Reverse:
                                      (SEQ ID NO. 22)
TTAGAACCGTGTCTTCTACAATTGA Fragment 3: 45k-3 1.3kb C_H1Δ
45k-3-left
Forward:
                                      (SEQ ID NO. 23)
GGGTAGGAGGTTGTTGGTTA Reverse:
                                      (SEQ ID NO. 24)
CCCGCTGGGCTCTGCAAGAGAGGAGAATGTGTGA 45K-3-right
Forward:
                                      (SEQ ID NO. 25)
CTCTCTTGCAGAGCCCAGCGGGCCCATTTCA Reverse:
                                      (SEQ ID NO. 26)
GCTTGTTTTTATATCGAGCTTGC Fragment 4: 45k-4 8412bp
Forward:
                                      (SEQ ID NO. 27)
TCAGTCTCACTTGCCTGGTCGT Reverse:
                                      (SEQ ID NO. 28)
CTTTGTAGCACATGCGTCATCC Fragment 5: 45k-5 9012bp
Forward:
                                      (SEQ ID NO. 29)
TGAAGGCATGAAGGAGTTGAGC Reverse:
                                      (SEQ ID NO. 30)
ACAACCCCTATCCTACACATT Fragment 6: 45k-6 2274b C_H1Δ
45k-6-left
Forward:
                                      (SEQ ID NO. 31)
GGGTCCTGGCAACATTAGCG Reverse:
                                      (SEQ ID NO. 32)
CACTCTGGGCTCTGCAAGAAAGGAGGATGTGTGA 45k-6-right
Forward:
                                      (SEQ ID NO. 33)
CTTTCTTGCAGAGCCCAGAGTGCCCATAACAC Reverse:
                                      (SEQ ID NO. 34)
TGGTGTTCAGCAGGCTAATTTG Fragment 7: 45k-7 9968bp
Forward:
                                      (SEQ ID NO. 35)
CAGGCCCCACTTCTTTACCTAA Reverse:
                                      (SEQ ID NO. 36)
TTGTTAGTTCATCACAGGGCAATTC
```

The 7 PCR products and the linearized BAC-YAC vector with overlapping sequences to fragment 1 and 7 at the ends were transformed into yeast for homologous recombination. The 45 kb-YAC was confirmed by PCR of the joins, PFGE and sequencing. PmeI restriction enzyme releases the 45 kb fragment from the circular YAC.

Generating 58 kb Fragment Containing $C_H1$ Deleted Cγ1, Cγ2b and Cγ2a.

The mouse μ enhancer and switch μ fragment, Cγ1 fragment with deleted CH1 and linker 1 (1.3.1), the 45 kb PmeI restriction fragment containing Cγ2b and Cγ2a and the linearized BAC-YAC vector with overlapping sequences to 5' of the μ enhancer fragment and 3' of the 45 kb fragment at the ends were transformed into yeast for homologous recombination. The 58 kb-YAC was confirmed by PCR of the joins, PFGE and sequencing. PmeI restriction enzyme releases the 58 kb fragment from the circular YAC.

Yeast Transformation for YACs with Multiple Constant Genes

Two fragments, one of 58 kb comprising Cγ1-Cγ2b-Cγ2a and the other a YAC arm with overlapping sequence to the 3' end of the 58 kb fragment were introduced into yeast containing YAC destined for addition of the Cγ1-Cγ2b-Cγ2a genes by spheroplast transformation. Transformants were selected on amino acid drop out medium depend on the auxotrophic markers carried on the YAC arm. Homologous recombination between the overlapping fragments resulted in the addition of the Cγ1-Cγ2b-Cγ2a fragment and new YAC arm to the YAC of choice, The new YAC was characterized by PCR and sequencing of the joining sites. The size of the new YAC was confirmed by PFGE and southern blotting. Subsequently, the 42 kb mouse 3' enhancer was added (as described above) generating Crescendo YAC3 (FIG. 10).

Example 2: Generation of Knockout Mice

The methods used to silence the mouse heavy chain locus (WO2004/076618+Ren, L., et al., Genomics 84 (2004), 686-695), the mouse lambda locus (Zou, X., et al., EJI, 1995, 25, 2154-2162 and WO2003/000737) and the kappa locus (Zou, X., et al., JI 2003 170, 1354-1361 and WO2003/000737) have been described previously. Briefly, large scale deletions of the mouse heavy chain constant region and the mouse lambda chain locus resulted in silencing of these two immunoglobulin chains. The kappa light chain was silenced via a targeted insertion of a neomycin resistant cassette.

a) Cross-Breeding of Heavy and Light Chain KO Mice

Mice with dual silencing of the endogenous light chains (kappa and lambda) were created by conventional breeding (Zou, X., et al., JI 2003 170, 1354-1361). These light chain-KO mice were further bred with heavy chain KO mice to give triple heterozygous animals for breeding to derive a triple knockout (TKO) line. This line proved to be fertile and is maintained as a true-breeding line.

b) Genotyping of Progeny from Cross-Breeding

Primers were designed to allow discrimination between wild-type and silenced loci for each of the endogenous heavy chain, kappa and lambda light chain regions. Genomic DNA was extracted from tail or ear biopsies taken from pups and was used for template DNA within the PCR reactions. The gDNA was extracted using well described methods (eg using Viagen Direct PCR lysis reagent (tail) cat no 102-T, according to the manufacturer's instructions). The following primers (purchased from Sigma) were used in the PCR reactions.

Heavy Chain Primers

```
Igh-Cdel-F
                                        (SEQ ID NO. 37)
AGAGCCCCTGTCTGATAAGAATCTGG Igh-Cdel-R
                                        (SEQ ID NO. 38)
GAGTCCCCATCCCCAAGGCTGG Igh-WT1027-long
                                        (SEQ ID NO. 39)
GATGGTGAAGGTTAGGATGTCTGTGGAGGGAC
```

PCR Product Sizes:

WT: 1027 bp

KO: 613 bp

HET: 1027 and 613 bp

Kappa Primers

```
TPMoKfor
                                        (SEQ ID NO. 40)
CCATCTTCCCACCATCCAGTGAGC TPMoKrev
                                        (SEQ ID NO. 41)
GCAACAGTGGTAGGTCGCTTGTGG
```

Kappa PCR Product Sizes:

WT: 400 bp

KO: 1700 bp

HET: 400 bp and 1700 bp

Lambda Primers

```
LJ2B FW
                                        (SEQ ID NO. 42)
GGAGATCAGGAATGAGGGACAAAC

LC1 RV
                                        (SEQ ID NO. 43)
GCCTTTCCCATGCTCTTGCTG

Lamgen WT rev2
                                        (SEQ ID NO. 44)
GGCAGGAAAGAAGGGTTAAGAT
```

Lambda PCR PRODUCT SIZES:

WT: 1127 bp

KO: 686 bp

HET: 1127 bp and 686 bp

These primers can be used with various DNA polymerase enzymes and buffers and cycling conditions can be adapted to suit the particular enzyme. As an example, Fermentas DreamTaq-Ready Mix (#K1081) can be used as follows;

|  | ul/reaction |
|---|---|
| 2 x Dream Taq | 10 |
| Primers (10 uM) | 0.2 of each (x5) |
| H₂O to 19 ul | 8 |

1 ul of template is used for the reactions. A positive control and a water control were always included within the samples to be genotyped.

The following cycling conditions were used for this particular enzyme;

94° C. 2′
94° C. 30″
60° C. 30″ ×30
72° C. 1′
72° C. 5′

Following PCR reactions, the products were visualised using a DNA stain following electrophoresis on a 1% agarose gel. FIG. 11 shows the results of a representative genotyping experiment with genomic DNA extracted from 2 animals with wt, heavy chain KO, light chain KO or TKO genotypes.

c) Lack of Endogenous Immunoglobulin Expression in TKO Mice

The null phenotype of the TKO mouse was confirmed using enzyme linked immunosorbant assays (ELISA) specific for mouse heavy chains, heavy chain/light chain complexes and light chains. Briefly, immunosorbant plates (e.g. Nunc Maxisorb 96F well plates Cat. No. 443404) were coated with a 5 ug/ml solution of capture antibodies, diluted in phosphate buffered saline (PBS). Following washing with PBS/0.05% Tween, PBS and blocking with a 3% solution of milk powder, dilutions of serum (in 3% milk powder/PBS) were applied to the plates. After washing away unbound protein, bound proteins were detected using an appropriate biotinylated-detection antibody solution, used at a pre-determined optimal dilution, followed by neutravidin-HRP visualisation. Various commercially available antibodies can be used for these ELISA. Table 1 gives examples of such antibodies.

TABLE 1

Antibodies used in ELISA

| ELISA | Capture Antibody | Detection Antibody |
|---|---|---|
| Mouse Heavy Chain | Jackson 115-005-164, AffiniPure Goat Anti-Mouse IgG (subclasses 1 + 2a + 2b + 3), Fcγ Frag Spec. | Amersham RPN1001V, anti-mouse Ig biotin |
| Heavy Chain/ Light Chain complexes | Jackson 115-005-164, AffiniPure Goat Anti-Mouse IgG (subclasses 1 + 2a + 2b + 3), Fcγ Frag Spec. | Jackson 115-065-174, Biotin-SP-conjugated AffiniPure F(ab')2 fragment Goat anti-mouse IgG, Light chain specific |
| Light chains | BD 559748 & BD 553432, Rat anti-mouse Ig kappa, clone 187.1 and Rat anti-mouse Ig lambda 1, 2, 3. | Jackson 115-065-174, Biotin-SP-conjugated AffiniPure F(ab')2 fragment Goat anti-mouse IgG, Light chain specific |

As evidenced in FIG. 12, the TKO mice were shown to be devoid of detectable endogenous immunoglobulin chains. Serum samples from each of 2 wild-type and 2 TKO mice were assayed.

d) Isolation and Culture of ES Cells

The isolation of embryonic stem cells has been described (Ying, Q. L. et al., Nature, 453, 519-523, 2008, Nichols, J. Et al., Development, 1136, 3215-3222, 2009, Nagy, K. & Nichols, J., "Derivation of Murine ES Cell Lines", p 431-455 in "Advanced Protocols for Animal Transgenesis. An ISTT Manual. Ed. Shirley Pease & Thomas L. Saunders). The 2i method takes advantage of small molecule inhibitors that block the FGF/Erk signalling pathway, maintaining the ES cells in an undifferentiated state. Moreover, incubating early-stage embryos in medium containing these inhibitors diverts the intracellular mass of the embryo into the epiblast lineage, impeding the development of the differentiation-inducing hypoblast. This provides an enriched epiblast compartment from which ES cell lines can be more readily derived.

ES cell lines have been derived from TKO embryos. Early stage TKO embryos were thawed from cryopreservation and cultured, as defined in the referenced methods, until they reached the blastocyst stage. They were then cultured for a further 2 days before liberation of the epiblast which was accomplished by removal of the trophectoderm using anti-mouse serum and complement. The epiblast was then expanded before dis-aggregation in trypsin solution and expansion of the resulting ES cell lines. Culture media for the propagation of ES cell lines and clones are well described. In the present case, ES lines were maintained in either 2i medium or were weaned onto media supplemented with LIF and serum.

Example 3: Transgenesis a) Pronuclear Microinjection

The technique of pronuclear microinjection of DNA to create transgenic animals is well described (eg see K. Becker & B. Jerchow "Generation of Transgenic Mice by Pronuclear Microinjection" pp 99-115 in "Advanced Protocols for Animal Transgenesis. An ISTT Manual. Ed. Shirley Pease & Thomas L. Saunders. Springer Protocols 2011). Briefly, fertilised oocytes are isolated from superovulated female mice that have been mated with a stud male. To give superovulation, females are injected intraperitoneally at day −2 with 100 ul of PBS containing 5 I.U. of pregnant mare's serum gonagotropin (PMSG). After 46-48 hours, 5 I.U. of human chorion gonadotropin (hCG) in 100 ul of PBS is administered (i.p.) and the females are mated with the stud males. The following morning, cumulus complexes are harvested from collected oviducts and oocytes released by digestion with hyaluronidase solution. Various strains of mice can be successfully employed for producing the fertilised oocytes for microinjection.

Using C57BI6×CBA F2 wildtype (wt) mice, the above procedure was adopted to introduce purified YAC DNA. As indicated in the transgenesis overview (FIG. 13), a similar procedure is adopted when using TKO mice. In order to facilitate their purification for microinjection, YACs were transformed into so called 'window' strain yeast (Hamer et al., PNAS, 1995, 92(25), 11706-10). 'Window' strain yeast are a series of host yeast created with strategic splits of endogenous chromosomes such that, when subjected to gel electrophoresis, the passenger YAC migrates at a size devoid of yeast endogenous chromosomes. Alternatively, an appropriate "window" was created de novo using appropriate primers and PCR strategy to split a yeast chromosome. Thus, the YAC for microinjection was purified using pulsed-field gel electrophoresis (PFGE), followed by a second gel electrophoresis elution process. This procedure is described by A. Fernandez, D. Munoz & L. Montoliu in "Generation of Transgenic Animals by Use of YACs" pp 137-158 in "Advanced Protocols for Animal Transgenesis. An ISTT Manual. Ed. Shirley Pease & Thomas L. Saunders. Springer Protocols 2011. Following collection of the fertilised oocytes, the purified YAC DNA solution was injected into the pronucleus using pulled glass microinjection needles. All work was undertaken using micromanipulators under a microscope bearing a heated stage and mounted on a vibration isolation table. After microinjection, the oocytes were allowed to recover for up to 24 hours and then transferred to the oviducts of pseudopregnant surrogate mothers. Pseudopregnant females were produced by mating females with vasectomised stud males 24 hours prior to the transfer date. Pups were usually delivered 19-21 days later. Due to their size, the microinjection of YACs is a demanding process and the efficiency of insertion is lower than that seen with smaller BACs or plasmids. Table 2 summarises statistics derived from microinjection projects that were performed with 2 related YAC constructs.

TABLE 2

Transgenesis via Pronuclear Microinjection of purified YAC

| YAC | # Expts | # oocytes injected | # oocytes transferred | # pups delivered | # pups analysed | # transgenic mice | % transgenic mice |
|---|---|---|---|---|---|---|---|
| YAC 1 | 10 | 834 | 562 | 69 | 59 | 5 | 8.5% |
|  |  |  |  |  |  | 4           1 | 1.7% |
|  |  |  |  |  |  | partial  intact |  |
| YAC 2 | 7 | 674 | 474 | 123 | 122 | 13 | 10.7% |
|  |  |  |  |  |  | 12          1 | 0.8% |
|  |  |  |  |  |  | partial  intact |  | b. ES Cells

There are various routes to introduce the YAC constructs into ES cells (described below). Regardless of which route is chosen, the aim is to obtain ES clones which have successfully integrated the transgene. The advantage of ES-mediated transgenesis over pronuclear microinjection technique is that ES clones can be fully characterised prior to their use for the creation of a transgenic line. The characterisations that are performed on the ES clones are essentially the same as those that have been employed for screening F0 and F1 animals derived from pronuclear injection (see below). In situ hybridisation may also be applied to determine the chromosome of integration. This may be particularly desirable if the ES cells are wt rather than TKO; only ES clones that have the YAC integrated on a chromosome lacking an endogenous mouse immunoglobulin locus would be selected for the creation of a transgenic line. This pre-selection would ensure no linked loci were present that might impede efficient backcrossing to the TKO background.

In future, the development of processes that support the in vitro differentiation of ES cells to the B cell lineage may enable functional testing of the introduced transgenic locus prior to transgenesis. However, currently this is not technically feasible.

i) Transfection of Purified YAC

YACs can be purified essentially as described previously (see above, "preparation of YAC for microinjection"). The purified YAC is introduced to ES cells using, for example, lipofection (e.g. with Invitrogen Lipofectamine reagents), after which the ES cells are subjected to selection using Hygromycin (alternative selective reagents may be used, as dictated by the YAC design). Clones are picked and screened and appropriate clones are used to create transgenic lines. Various features may be introduced into the constructs and/or the targeted ES cells to facilitate the derivation of transfected ES clones (see below).

ii) Spheroplast Fusion Method

An alternative method for introducing YACs to ES cells is by spheroplast fusion. This method provides the advantage that manipulations of the large constructs are minimised thereby limiting the potential for damage to occur to the construct by shearing. The spheroplast fusion technique has been described (Davies, N., et al., "Human antibody repertoires in transgenic mice: manipulation and transfer of YACs" p 59-76 in "Antibody Engineering. A Practical Approach" Ed. McCafferty et al., IRL Press at Oxford University Press, 1996). Briefly, yeast spheroplasts are generated by zymolyase digestion of the yeast cell wall. Disaggregated ES cells are mixed with the spheroplasts and fusion is accomplished via the addition of polyethyleneglycol solution. Following resuspension in medium, the ES cells are washed and subjected to selective culture, cloning and screening as described below.

iii) Targeted Build-on of Tg/TKO ES Cells

An alternative strategy to add additional features to the YAC1 transgene (which contains a core structure common to all subsequent YAC constructs) is to perform targeted extensions of a YAC1 transgene located within an ES cell line (FIG. 14). ES cell lines bearing the YAC1 transgene are generated in vitro or derived from embryos of YAC1 transgenic mice. New features may be introduced into the transgene by homologous recombination or by use of insertion vectors as described elsewhere herein.

Example 4: Characterisation and Screening of Founders a) Presence of Transgene and Germline Transmission All pups born following transfer of microinjected oocytes were checked for the presence of the YAC within their genomic DNA. For ES cell-derived transgenic pups, coat colour genetics can also be exploited in combination with the selection of suitable blastocysts donor animals to allow chimeric pups to be readily identified from their fur colour. The following examples of screening use litters derived from pronuclear microinjection transgenesis. However, ES clones can be subjected to similar analyses prior to transgenesis, with resultant litters being screened for confirmatory results.

Testing for the YAC transgene involves purifying gDNA from tail or ear biopsies and testing for regions of the YAC using PCR reactions. The isolation of gDNA and PCR methods have been described previously (see above). PCR reactions targeting areas at each end of the YAC were performed and any samples with positive integrants for both regions were then screened with further primers designed to amplify various internal regions of the YAC transgene. PCR primers used for these screens are listed in table 3. Any founder mouse (F0) giving PCR positive results was then mated to check for germline transmission of the transgene(s) and also to confirm that the PCR screening results were due to the presence of an intact YAC rather than fragments; in the case of the latter, the most likely scenario was that the fragments were located on different chromosomes and as such were identified by their independent segregation amongst the F1 progeny. An example of the screening of a founder and its germline transmission is shown in FIG. 15.

TABLE 3

PCR Primers used for Screening for Presence of Transgene and Germline Transmission

| YAC region | Primers | Product Size (bp) |
|---|---|---|
| $V_H$ 2-5 | Left GAGGGAGCACCAATGAGAAG (SEQ ID NO. 45)<br>Right CAGATGAGGGGAATGCAAAT (SEQ ID NO. 46) | 625 |
| $V_H$ 4-4 | Left CCCAAGCTTGGTGCCTCTGATCCCAGGGCT (SEQ ID NO. 47)<br>Right GCTCTAGATCTGGGCTCACACTCACCT (SEQ ID NO. 48) | 380 |
| $V_H$ 1-3 | Left CCCAAGCTTGAAGCCAGTCAAGGGGCTTC (SEQ ID NO. 49)<br>Right GCTCTAGAGGGGTTTTCACACTGTGTC (SEQ ID NO. 50) | 400 |
| $V_H$ 1-2 | Left CCCAAGCTTGAGTCCAGTCCAGGGAGATCT (SEQ ID NO. 51)<br>Right GCTCTAGAGGGGTTTTCACACTGTGTC (SEQ ID NO. 52) | 615 |

TABLE 3-continued

PCR Primers used for Screening for Presence of Transgene and Germline Transmission

| YAC region | Primers | Product Size (bp) |
|---|---|---|
| $V_H$ 6-1 | Left CCCAAGCTTTCACAGCAGCATTCACAGA (SEQ ID NO. 53) Right GGAATTCCTGACTTCCCCTCACTGTG (SEQ ID NO. 54) | 336 |
| 3-63 (DP-81) | Left GGGGCTGGAGGGAGTAATAG (SEQ ID NO. 55) Right ACTTAGCTCGGACCACAGGA (SEQ ID NO. 56) | 603 |
| 3-64 (YAC6) | Left ATGATGGAGTTTGGGCTGAG (SEQ ID NO. 57) Right GGAAATCAGCCTTCATCTGC (SEQ ID NO. 58) | 597 |
| 3-65 (YAC4) | Left GGGTACTGCCTTCTCGTCAG (SEQ ID NO. 59) Right ATTTGCAGATAGGCGATGCT (SEQ ID NO. 60) | 600 |
| 1-67 (YAC8) | Left CCACGCTGGTCAGTTTTGTA (SEQ ID NO. 61) Right GCTGGGAATAGGGGACTCTC (SEQ ID NO. 62) | 403 |
| 1-69 (YAC7) | Left GGGGTGAGACACCTGAAGAA (SEQ ID NO. 63) Right GAGTGCAGGAAAATCATCCA (SEQ ID NO. 64) | 406 |
| 2-70 (YAC3) | Left GCACAGGTTTGTGGCATTTA (SEQ ID NO. 65) Right TGCAGCGGTAGGTTTTCTTT (SEQ ID NO. 66) | 298 |
| V3-7 | Left GCCCTTCACAGAGTCCACAT (SEQ ID NO. 67) Right ACTCCAAGGCCTTTCCACTT (SEQ ID NO. 68) | 409 |
| 3-72 (DP-29) | Left ATCTCTTCCCCTGCACTTCC (SEQ ID NO. 69) Right CTACCAAACGACCCAGCAAT (SEQ ID NO. 70) | 395 |
| 3-73 (YAC9) | Left CCATCCTCAGCAACATCTGA (SEQ ID NO. 71) Right GCATGAAAGGTCCTGCTACC (SEQ ID NO. 72) | 405 |
| 3-76 (DP-41) | Left GGGTGGAGAGACCAGTGTGT (SEQ ID NO. 73) Right TTAGGTGCTGGGAGCTCATT (SEQ ID NO. 74) | 386 |
| 5-78 (DP-80 | Left AGGACCATGGACAAGAGTGC (SEQ ID NO. 75) Right TTGGAAGGATGGGCTGTATC (SEQ ID NO. 76) | 608 |
| 7-81 (YAC10) | Left GGGAGAATCCCCTAGAGCAC (SEQ ID NO. 77) Right GTGGATGTCGATGCAAAATG (SEQ ID NO. 78) | 596 |
| V1-8 | Left AGCTCCATGTAGGCTGTGCT (SEQ ID NO. 79) Right ATGGACTGGACCTGGAGGAT (SEQ ID NO. 80) | 391 |

TABLE 3-continued

PCR Primers used for Screening for Presence of Transgene and Germline Transmission

| YAC region | Primers | Product Size (bp) |
| --- | --- | --- |
| V3-9 | Left GGAGTTCTTGGCGTTGTCTC (SEQ ID NO. 81)<br>Right AGGACTCACCATGGAGTTGG (SEQ ID NO. 82) | 392 |
| V3-11 | Left CTCAGGCTGTTCATTTGCAG (SEQ ID NO. 83)<br>Right GAGCTGGGTTTTCCTTGTTG (SEQ ID NO. 84) | 400 |
| V3-13 | Left GGCATTTTCTCTGGAGATGG (SEQ ID NO. 85)<br>Right AGGACTCACCATGGAGTTGG (SEQ ID NO. 86) | 392 |
| D 1-1 | Left GAGTCATCAGGGTCGGTGTC (SEQ ID NO. 87)<br>Right ACGACCACCGTGAGAAAAAC (SEQ ID NO. 88) | 403 |
| D 2-8 | Left GCTGGTGGGTGTGATGTATG (SEQ ID NO. 89)<br>Right CTTCCCTTGACCGAAGACAG (SEQ ID NO. 90) | 406 |
| D 3-16 | Left CTGTGGTAGCCACCATACCC (SEQ ID NO. 91)<br>Right TGGGTAGGGACATAGGGACA (SEQ ID NO. 92) | 388 |
| D4-23 | Left GCTCTTGTGCTCCTGGAGAG (SEQ ID NO. 93)<br>Right AAAAGGTATCCCCACCTTGC (SEQ ID NO. 94) | 401 |
| J1P | Left GGGGAGCATGGTTTTTGTA (SEQ ID NO. 95)<br>Right CTGCTGCTGGGAAAACAAGT (SEQ ID NO. 96) | 400 |
| J3 | Left GCAGGAGAGAGGTTGTGAGG (SEQ ID NO. 97)<br>Right GCTTTCCTTCTGCCTCCTTT (SEQ ID NO. 98) | 390 |
| J6 | Left CCTGGTTTGTTCAGGCATCT (SEQ ID NO. 99)<br>Right CGGAGACAGAAGGTCTCTGG (SEQ ID NO. 100) | 398 |
| Emu | Left AGCCTTTTCAGTTTCGGTCA (SEQ ID NO. 101)<br>Right CTGGTTTCCAAGAGAAAAGGA (SEQ ID NO. 102) | 581 |
| Linker 1-3'enh | Left CAAGTGTACAGTCCCCGAAGCAAG (SEQ ID NO. 103)<br>Right TGATACACGCAACACGCTTGTC (SEQ ID NO. 104) | 1357 |
| Linker 2-3'enh | Left GAGGTACAGGGGGCTCATGGGT (SEQ ID NO. 105)<br>Right CTTGGCCCGCATTTACAAGACTATC (SEQ ID NO. 106) | 954 |
| His 3 | Left CGTGCGTGGAGTAAAAAGGT (SEQ ID NO. 107)<br>Right TGAACGCACTCTCACTACGG (SEQ ID NO. 108) | 592 |

TABLE 3-continued

PCR Primers used for Screening for Presence of Transgene and
Germline Transmission

| YAC region | Primers | Product Size (bp) |
|---|---|---|
| Trp | Left GCCCAATAGAAAGAGAACAATTGACC (SEQ ID NO. 109)<br>Right ACACCTCCGCTTACATCAACACC (SEQ ID NO. 110) | 488 | b) Fingerprint Analysis of the YAC Transgene

In all cases, the transgenic locus carried human genomic DNA sequence. It is therefore possible to screen for the presence of the human DNA Alu element G15N2 (Genbank X55929.1) which is a repeated motif present in human sequences. A given region of human gDNA digested with restriction enzymes yields a characteristic band pattern upon Southern Blot analysis using an Alu probe. Thus, the Alu fingerprint of the YAC is compared with that obtained from gDNA extracted from transgenic animals to give an indication of the structural integrity of the transgene. Intact YAC transgene is expected to give a similar fingerprint to the YAC present within the yeast.

The Alu probe is prepared from cloned sequence (Genbank X55929.1) or gDNA using the following primers:

| Region | Primers | Product Size (bp) |
|---|---|---|
| Alu | Left GGATCACGAGGTCAGGAGAT (SEG ID NO. 111)<br>Right ACGGAGTCTCGCTCTGTCG (SEQ ID NO. 112) | 221 |

The following cycling conditions are;

$$\left.\begin{array}{l} 94°\text{ C. } 5' \\ 94°\text{ C. } 30'' \\ 63°\text{ C. } 30'' \\ 72°\text{ C. } 1' \\ 72°\text{ C. } 10' \end{array}\right\} \times 35$$

The probe is labelled using either radioactive or non-radioactive methods (e.g. a DIG probe synthesis kit (Roche cat #11636090910) is used during the PCR step to add DIG-dUTP residues). Chemiluminescent detection of the probed-Southern blot is then mediated via the addition of alkaline phophatase-labelled anti-Digoxigenin antibody followed by an appropriate substrate (eg CDP-Star luminescent substrate, Sigma C0712).

c) Copy Number of the Transgene

It is possible that more than one copy of the YAC may be present within the genome of a transgenic mouse (or a selected ES clone). This can occur either at different integration sites or in a repetitive fashion at a single chromosomal location. The number of independently segregating integration sites can be inferred from studies of the genetic inheritance pattern and an application of Mendelian genetics. For example, a single integration site would results in a 50% inheritance pattern amongst progeny, whilst 2 integration sites would give a 3:1 transgenic: non-transgenic inheritance.

A Q-PCR-based approach was used to compare relative quantities of amplicons from a region of the YAC with a PCR reaction of a housekeeper gene. Copy number evaluation was undertaken using multi-plexed reactions where the reference amplicon and transgene amplicon were reported using independent dyes. For example, TaqMan probe technology (or a suitable alternative) using assays specific for a housekeeper diploid gene (eg mouse transferrin receptor; Invitrogen cat no 4458366) and a region of the YAC (eg the human J region of the transgene; Taqman copy number assay id Hs03892805_cn or the Hygormycin selection gene; assay id Mr00661678) were used. For these reactions, Q-PCR were set up using commercially-available reagents (eg Taqman Genotyping Master Mix 400rxns, cat no 4371355) using conditions, based upon those recommended by the manufacturer and CT values for each of the amplicons are measured within the same PCR reaction. An example of a copy number analysis is shown in FIG. 16. In this example, Q-PCR analyses of DNA from mice that are heterozygous for YAC2 (single copy integrant) or homozygous for the YAC2 transgene (2 copies) are shown.

Example 5: Breeding to TKO a) Conventional Breeding

Transgenic mice created on a wild-type background were back-crossed with the TKO line to transfer the transgene onto this desired background. This was achieved by conventional breeding, using sequential breeding steps with carefully genotyped progeny being selected for each breeding schedule.

b) Back-Crossing Incorporating IVF

Taking a transgenic line to the TKO background is a lengthy procedure with each breeding round taking 9-12 weeks to complete. However, an IVF strategy was used to expand the breeding to such a scale that, with careful scheduling, it was possible to complete the backcross to give a sizable cohort of Tg/TKO pups in ~15 weeks from the initial mating of the Tg/wt with the TKO line. Table 5 contains data from such an IVF-enhanced breed programme. A similar IVF step may be used to rapidly expand transgenic lines that are produced already on a TKO background (e.g. from TKO/ES cells or from pronuclear microinjection to TKO oocytes).

Conditions were determined that allowed the TKO mice to be used for provision of large quantities of oocytes for fertilisation with sperm derived from transgenic donor male mice. Briefly, female mice of 8-12 weeks of age were treated with hormones to induce superovulation (see Example 3). The oocytes were fertilised with sperm from the stud trangenic males and fertilised oocytes were transferred to pseudopregnant females, either within 4-24 hours or cryopreserved for later transfer.

TABLE 5

| | Data from IVF breed of YAC1 line | | | |
|---|---|---|---|---|
| # transferred | Fresh or post cryo | # recipients | # pups | % |
| 690 | fresh | 35 | 222 | 32.2% |
| 300 | cryo | 15 | 150 | 50.0% |
| 300 | cryo | 15 | 32 | 10.5% |
| 1290 | | 65 | 404 | 31.3% |

Example 6: Evaluation of Transgene Usage

During B cell development, somatic recombination of the immunoglobulin loci takes place giving rise to the antibody repertoire (eg, for review see Kuby Immunology, sixth Edition; T. J. Kindt, R. A. Goldsby, B. A. Osborne, J Kuby. Published by W.H. Freeman and Company, New York, 2007.). For the heavy chain, this process involves V-D-J region recombination. Imprecise joining of these gene segments adds to the potential available diversity of the naive repertoire. The spliced VDJ gene fragments give rise to the $V_H$ domain and this is linked to other domains encoded by the constant region genes. The rearranged gDNA gives rise to RNA transcripts within the B cells and these are translated to give both membrane-expressed and secreted HcAb molecules. Thus, when looking for functional activity of the YAC transgene transcripts, both B cells and serum proteins were assayed.

The following sections describe some of the various molecular, protein and cellular assays that may be used to determine if an introduced transgene is functional.

a) Molecular Analysis; Transcripts — RT-PCR, Cloning and Sequencing

Lymphoid samples were obtained from the transgenic animals (eg blood sample, spleen). RNA was isolated from the lymphoid samples using commercially available reagents (e.g. RNeasy Qiagen kit cat no. 74106) and reverse transcribed using appropriate primers (details below) or oligodT primer (Gibco) with Supercript III enzyme (Gibco). All associated buffers and conditions were as recommended by the manufacturer. The cDNA thus obtained was used in PCR reactions to amplify $V_H$ regions, either using primers specific for the $V_H$ domains (some with adaptions for onward library generation — see below) or with primers for the $V_H$ leaders and constant regions (Table 6).

TABLE 6

| Primers employed for analysis of transgenic mice | |
|---|---|
| Mouse $C_H2$ rev | GACCTCGGGATCATCCTTGC (SEQ ID NO. 113) |
| $V_H$leader1_17mer | ATGGACTGGACCTGGAG (SEQ ID NO. 114) |
| $V_H2$ leader.2 | ATGGACACACTTTGCTCCACGC (SEQ ID NO. 115) |
| $V_H4$ leader | ATGAAACACCTGTGGTTCTTC (SEQ ID NO. 116) |
| $V_H6$ leader | ATGTCTGTCTCCTTCCTCATC (SEQ ID NO. 117) |
| $V_H3$-leader | ATGGARTTKGGRCTGAGCTG (SEQ ID NO. 118) |
| $V_H1.2.3$_genomic_rev | GTCAGGATGTGGGTTTTC (SEQ ID NO. 119) |
| $V_H2.5$_genomic_rev | GGAGGTGCCCTGGGCTGTGTC (SEQ ID NO. 120) |
| $V_H4.4$_genomic_rev | GTGTCTGGGCACACACTC (SEQ ID NO. 121) |
| $V_H6.1$_genomic_rev | CTCACACTGACTTCCCCTC (SEQ ID NO. 122) |
| V1/a | GGAACAGACCACCATGGCCCAGGTBCAGCTGGTGCAGTCTG GGGCTGAGG (SEQ ID NO. 123) |
| V1/B | GGAACAGACCACCATGGCCCAGGTBCAGCTGGTGCAGTCTG G (SEQ ID NO. 124) |
| VH1-2+ | GCCGCTGGATTGTTATTACTCGCGGCCCAGCCGGCCATGGCCCAGGTGCAGCTGGTG CAGTCTGGGGCTGAGG (SEQ ID NO. 125) |
| VH1-3 | GCCGCTGGATTGTTATTACTCGCGGCCCAGCCGGCCATGGCCCAGGTCCAGCTCGTGC AGTCTGGGGCTGAGG (SEQ ID NO. 126) |
| VH1-18 | GCCGCTGGATTGTTATTACTCGCGGCCCAGCCGGCCATGGCCCAGGTTCAGCTGGTG CAGTCTGGAGCTGAGG (SEQ ID NO. 127) |
| VH1-24 | GCCGCTGGATTGTTATTACTCGCGGCCCAGCCGGCCATGGCCCATCCAGCTGGTA CAGTCTGGGGCTGAGG (SEQ ID NO. 128) |
| VH2+ | GCCGCTGGATTGTTATTACTCGCGGCCCAGCCGGCCATGGCCCAGRTCACCTTGA AGGAGTCTGG (SEQ ID NO. 129) |
| V2/B | GGAACAGACCACCATGGCCCAGATCACCTTGAAGGAGTCTG G (SEQ ID NO. 130) |
| V3/B | GGAACAGACCACCATGGCCSAGGTGCAGCTGGTGGAGTCTG GGGGAGG (SEQ ID NO. 131) |

TABLE 6-continued

Primers employed for analysis of transgenic mice

| | |
|---|---|
| VH3-7+ | GCCGCTGGATTGTTATTACTCGCGGCCCAGCCGGCCATGGCCGAGGTGCAGCTGGTG GAGTCTGGGGGAGG (SEQ ID NO. 132) |
| VH3-9 | GCCGCTGGATTGTTATTACTCGCGGCCCAGCCGGCCATGGCCGAAGTGCAGCTGGTG GAGTCTGGGGGAGG (SEQ ID NO. 133) |
| VH3-11+ | GCCGCTGGATTGTTATTACTCGCGGCCCAGCCGGCCATGGCCCAGGTGCAGCTGGTG GAGTCTGGGGGAGG (SEQ ID NO. 134) |
| VH3-23 | GCCGCTGGATTGTTATTACTCGCGGCCCAGCCGGCCATGGCCGAGGTGCAGCTGTTG GAGTCTGGGGGAGG (SEQ ID NO. 135) |
| VH4-4+ | GCCGCTGGATTGTTATTACTCGCGGCCCAGCCGGCCATGGCCCAGGTGCAGCTGCAG GAGTCGGG (SEQ ID NO. 136) |
| V4-4/B | GGAACAGACCACCATGGCCCAGGTGCAGCTGCAGGAGTCGG G (SEQ ID NO. 137) |
| VH4-34 | GCCGCTGGATTGTTATTACTCGCGGCCCAGCCGGCCATGGCCCAGGTGCAGCTACAG CAGTGGGGC (SEQ ID NO. 138) |
| V6/B | GGAACAGACCACCATGGCCCAGGTACAGCTGCAGCAGTCAG G (SEQ ID NO. 139) |
| VH6-1 | GCCGCTGGATTGTTATTACTCGCGGCCCAGCCGGCCATGGCCCAGGTACAGCTG CAGCAGTCAGG (SEQ ID NO. 140) |
| VH_J/F | GCTACCGCCACCCTCGAGTGARGAGACRGTGACC (SEQ ID NO. 141) |
| JH | CCGTGGTGATGGTGGTGATGGCTACCGCCACCCTCGAGTGARGAGACRGTGACC (SEQ ID NO. 142) |

In the examples that follow, PCR reactions used proof-reader enzymes (eg Phusion high fidelity DNA polymerase, cat no F530S) and "touch-down" PCR cycling conditions.
Example Touchdown Programme;

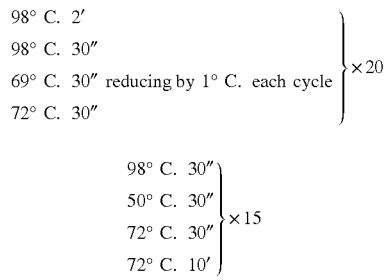

PCR products were purified and cloned into a commercially available cloning vector (eg pJET1.2, Fermentas K1231) or digested with NcoI and XhoI prior to cloning into a phagemid vector or incorporated into the phagemid vector using a PCR-based cloning strategy (see FIG. 17 and later for details of the phagemid vector).

Clones were sequenced and analysed to determine if transcripts derived from the transgene were present. Examples of transcripts cloned from transgenic animals are shown in FIG. 18. The available diversity of the $V_H$ repertoire within a transgenic animal may also be estimated from such sequence analysis (although bias can result from, for example, sampling processes or the inclusion of a particular PCR amplification step). In the examples shown in FIG. 19, $V_H$ were cloned from an individual naïve transgenic mouse. It is clear that the transgenic animals harbour diverse B cell repertoires, with few duplicate sequences being found, despite the use of polymerase chain amplification in the cloning steps. A wide range of CDR3 lengths was apparent from this single mouse analysis. The sequences were compared with germline $V_H$ sequences and a variabillity plot was constructed. $V_H$ derived from the naive mouse were largely germline, with little variation outside of the CDR3 region. In addition to the conventional cloning and sequencing outlined above, the $V_H$ repertoire may be analysed using, for example, next generation sequencing to interrogate the transcriptome of a transgenic animal.

b) Protein Analysis—Serum ELISA

The sandwich ELISA technique has been described previously (see characterisation of the TKO mouse). Using appropriate antibody pairs for capture and detection, protein encoded by the transgene was detected in the serum of transgenic mice. Reagents used for Sandwich ELISA are commercially available. Analysis of transgenic mice is shown in FIG. 20, where ELISA was used to detect HcAb within the serum.

We also examined the importance of the triple knock-out background for the performance of the transgenic platform for the production of HCAbs that utilise the human $V_H$ genes. To do this we used ELISA to look for the presence of the HCAb and heavy-chain/light chain complexes in the serum of mice knocked out for endogenous heavy chain genes but with various endogenous immunoglobulin light chain gene knock-out backgrounds (see FIG. 33). For the capture antibody, a polyclonal Goat anti-mouse IgG (H+L) with minimal cross-reactivity for Human, Bovine, Horse, Rabbit, and Rat Serum proteins (Jackson, cat #415-005-166) was used. This antibody was selected as it failed to bind directly the detection antibodies used in the assay (Biotin-Rat anti-Mouse Ig, Kappa light chain, clone 87.1, BD Pharmingen cat #559750, Biotin-Rat anti-mouse Ig, lambda1, lambda2 and lambda 3 light chains, clone R26-46, BD Pharmingen cat #553433, and Biotin-SP-conjugated *affini*-Pure Goat anti-mouse IgG, Fc-gamma Fragment specific, Jackson cat #115-065-008). Thus, any signal measured could be attributed to the binding of the detection antibody to captured heavy chain proteins and not to the capture antibody in the sandwich ELISA. Briefly, for the ELISA, antibodies in the serum of the mice were captured via the coated anti-mouse IgG antibody. Following washing, captured heavy chain proteins or complexed light chains were detected using either a biotinylated-anti-mouse IgG heavy chain-specific antibody or a biotinylated-anti-mouse Kappa light chain Ab or a biotinylated-anti-mouse lambda chain Ab. The detection antibodies were visualised using TMB substrate where the colourimetric reaction was triggered by Neutravidin-HRP complexes binding to the biotin tags of the detection antibodies. As shown previously (see FIG. 12), a TKO mouse lacking a transgene did not have antibodies in its serum. However, when a YAC2 transgene was present, HcAb could be found in all cases, regardless of the endogenous immunoglobulin light chain gene background. If a functioning endogenous kappa gene locus was present, kappa light chains could be detected on the captured heavy chains, indicating the presence of transgenic HcAb, complexed with endogenous kappa light chains. Similarly, if a functioning lambda locus was present, lambda light chains could be detected associated with the captured heavy chains, indicating the presence of transgenic HcAb, complexed with endogenous lambda light chain proteins. When both endogenous kappa and endogenous lambda light chain loci were present, kappa chains were preferentially used, as is normal in the mouse where lambda rearrangements are prevented by the successful production of a kappa light chain protein. Thus, in this case, lambda light chains were harder to detect in association with the transgenic chimearic HCAb. The results of these ELISA, demonstrate the necessity of having a triple knock-out background, incapable of producing any endogenous immunoglobulin proteins, for the provision of a transgenic mouse capable of producing solely Hc-only antibodies.

Example 7: Cellular Analysis—Flow Cytometry

The B cell development pathway can be monitored using flow cytometry employing various well-characterised reagents and markers associated with particular developmental steps. For example, early pre-B cells express c-Kit and IL7R, with other markers such as CD43, CD19, B220 being acquired (e.g. CD19, B220) or acquired and down-regulated (eg. CD43) as the cell progresses to a mature surface Ig-positive B cell (see FIG. 21). Moreover, within the B cell repertoire, markers may be employed to distinguish B-2 B cells (CD23+, CD5−) from other B cell subsets, the former being capable of participating in the acquired humoral immune response (see FIG. 22).

For flow cytometry analysis, single cell suspensions were prepared from lymphoid tissues (eg bone marrow, spleen) and, following blocking (e.g. with Fc fragments (Rockland)) stained in FACS buffer (PBS/1% BSA/0.01% $NaN_2$) with antibodies to surface marker or isotype controls. Biotin-conjugated antibodies were detected using a suitable streptavidin conjugate (e.g. PE-Cγ7 streptavidin). Following staining, cells were fixed with 3.7% formaldehyde solution and analysed with a flow cytometer (e.g. a FACSCalibur or LSRII machine) using appropriate voltages and compensation settings. The data was analysed using a variety of software packages, including FlowJo & WinMDI, a freeware programme (see FIGS. 21 & 22). Reagents for staining prior to flow cytometry analysis are well known in the art (e.g. see bd.com/uk/products/main.asp)

Example 8: Immunohistochemistry of Spleens

Spleens have an organised architecture with red and white pulp areas, the latter containing B cell and T cell rich zones. Haematoxylin and eosin staining of tissue sections taken from formaldehyde-fixed paraffin-embedded tissues was used to reveal this architecture and comparative images are shown for wild type, triple KO, and Tg/TKO mice (FIG. 23). From these, it is apparent that the architecture is compromised in the TKO mice with the follicles having fewer cells and an absence of marginal zones around the follicles. These features are consistent with the absence of B cells in the TKO mice. As the images show for Tg mice, the architecture is restored and follicles are more densely populated and surrounded by an obvious marginal zone.

Example 9: Generation of $V_H$ Domains

Target-specific $V_H$ domains were isolated using display libraries created using RNA derived either from immunised or from naïve transgenic mice.
a) Immunisation
A selection of different target antigens were administered to transgenic mice using one of a number of immunisation protocols that are well known in the art. Examples of serum ELISA are shown in FIG. 24. The sandwich ELISA is similar to those outlined above. Briefly, absorbant plates were coated with antigen, and following washing and blocking, dilutions of sera from the animals was added. Any HCAb binding to the antigen coated plates was detected following incubation with biotinlyated anti-Fc Ab followed by neutravidin-HRP and addition of substrate.
b) Naïve Libraries
Large libraries for each VH family were constructed using 113 spleens from YAC1 transgenic mice. Each spleen was individually processed and aliquots of individual RNA was used for the different VH family library constructions, as outlined above. A summary of the properties of this library is shown in FIG. 35 Naïve Libraries. The library consists of approximately $3.81 \times 10^{10}$ clones and a sample of sequencing from each family indicates high clonal diversity, with most clones only being isolated a single time within the sample
Construction and Use of cDNA Libraries
Display libraries were constructed from both naive and immunised transgenic animals. Briefly, lymphoid tissues were collected into RNA later and then subject to mechanical homogenisation and lysis. Alternatively, fresh lymphoid tissues, blood or another source of B cells, including hybridomas, may be used as the source of RNA. Following extraction of RNA, (either total or messenger RNA) cDNA was made. PCR was then used to amplify the $V_H$ sequences, adding appropriate adapters to permit cloning into a phagemid vector. Many strategies may be used to clone the $V_H$. In the present case, degenerate primers for the leader sequences present within the transgene were used in conjunction with a degenerate primer for the J/H junction. An alternative method relies on using terminal deoxytransferase to add a repetitive deoxynucleotide basetail or anchor for use in place of the leader sequences. Following amplification, the $V_H$ products were either digested with NcoI and XhoI and ligated into the vector or used as primers and incorporated into the phagemid vector using a PCR-based strategy.

The phagemid vector was constructed in-house (see FIG. 17). Primers with added adaption sequences are described in a previous section (see Molecular analysis; Transcripts—RT-PCR, cloning and sequencing).

The libraries thus constructed were then used in phage display selections (see process schematic in FIG. 25). Variations of this technique, including but not limited to soluble selections, off- or on-rate biased selections, and competition selections can be employed.

Figure 34:
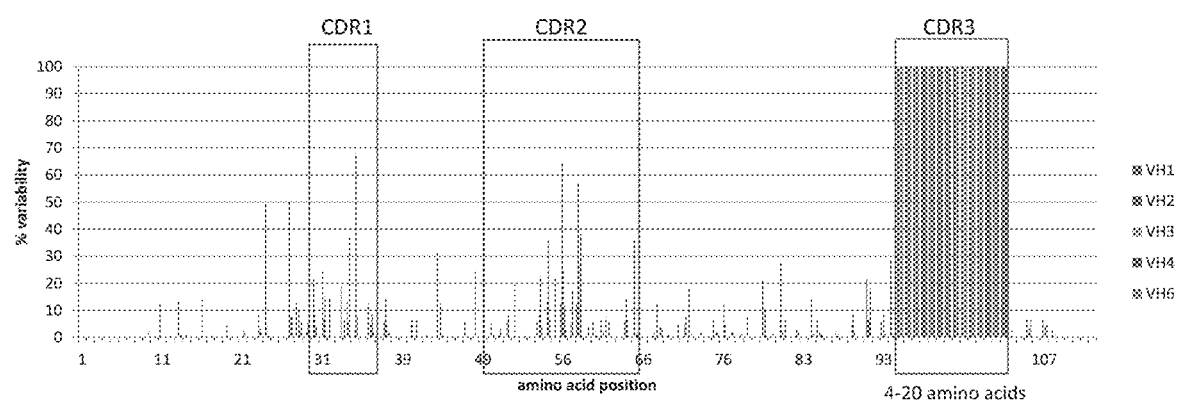

The output from each selection process was screened by ELISA and examples of some library screens before and after phage selection are shown in FIG. 26. In this case, a $V_H$ library was cloned from an immunised mouse and the library screened by ELISA both before and after it was selected on the immunising antigen. $V_H$ antibodies specific for the immunogen were identified by ELISA using $V_H$ purified from the periplasm of *E. coli*, following published methods (Antibody Engineering, Edited by Benny Lo, chapter 8, p 161-176, 2004). It is apparent that, ex-vivo the library contained a low frequency of immunogen binders. This is in keeping with the mining of the B cells, both responding and naive, within the transgenic mouse. Following phage selection the antigen-binding $V_H$ were enriched (FIG. 26). Indeed, as shown in FIG. 27, high diversity was apparent in the pre-selection library and following one round of stringent selection by phage display, the antigen-binding $V_H$ were found to belong to 50 sequence families, as grouped by CDR3 diversity. Moreover, evidence of somatic hypermutation was apparent from an examination of the CDR1, CDR2 and CDR3 sequences and many sibling sequences, presumably the result of in vivo somatic hypermutation within germinal centres, were isolated (see FIG. 27a)i)). That somatic hypermutation resulted in increased affinity for antigen is demonstrated for a select panel of four sibling sequences where binding to antigen is also shown (see FIG. 27a)i). Further evidence of somatic hypermutation leading to sequence diversification of the VH is shown in FIG. 34—Kabat and Wu of Antigen Binders. In this case, 105 VH that bound one of three antigens, were analysed and variation at each amino acid position, compared to germline sequence was plotted. By comparison with the similar plot from a naïve mouse (see FIG. 19), it is apparent that substantial mutations have accumulated, with mutations in the CDR1 and 2 regions being prevalent.

Further to isolation of the $V_H$ domains in accordance with known techniques and as described above, the $V_H$ domains were assayed to determine affinity for the target antigen (FIG. 28). This may be carried out by a number of techniques known in the art including but not limited to ELISA and BIAcore. In addition, binding to cell surface antigens can be measured by fluorescence activated cell sorting (FACS).

In addition to strength of binding to target antigen, the ability of a $V_H$ to influence the function of a given target may also be assayed (e.g. this would include inhibition of ligand: receptor binding). An example of the inhibition of a ligand/receptor interaction by inclusion of VH specific for the ligand is shown in FIG. 29.

Example 10: Properties of $V_H$

Transgenic mice carrying one of the YAC constructs described above offer a significant advantage for the discovery of high quality drug candidates. Unlike $V_H$ domains that are isolated from conventional sources (eg Human cDNA), the $V_H$ domains develop and are matured in the absence of a light chain. As such, the $V_H$ domains derived from the transgenic mice do not rely upon the presence of a partner light chain to stabilise their folding or retain their solubility. Evidence of this was derived from experiments comparing $V_H$ isolated from a naive transgenic mouse with those derived in vitro from a human cDNA library. Sequences for the $V_H$ were cloned into a phagemid vector as previously described and small scale (50 ml) expression studies in *E. coli* were undertaken. These were performed without optimisation of sequence and without use of specialised methods for maximising protein production. Following induction with IPTG, expression of soluble $V_H$ was determined. Using $V_H$ from matched V-gene families, it was observed that only 47% (15/32 clones) of the human cDNA-derived $V_H$ clones were able to provide at least 10 ug of soluble protein from *E. coli*-derived periplasmic extract. By comparison, 79% (27/34) of $V_H$ cloned from a naive transgenic YAC1/TKO mouse gave soluble expression yields in excess of 10 ug. Moreover, as the results represented in FIG. 30 show, on a population basis, higher yields were evident with $V_H$ that had developed in the absence of a light chain within a transgenic mouse (mean=176 ug/50 ml) compared to those that are derived from a human cDNA library (mean=37.6 ug/50 ml) which we assume had developed in association with a partner light chain. Thus, although $V_H$ from either source could be expressed in a soluble format, the population that developed within the transgenic mouse demonstrated enhanced solubility giving an overall approximately 5-fold greater yield of soluble protein. Enhanced yields were apparent for the in vivo affinity-matured $V_H$ that were cloned from the mice following immunisation. In this case, the small laboratory scale cultures gave rise to ~10 mg/litre, this being obtained using a phagemid expression system without any optimisation.

The melting temperature (Tm) of a protein can be used as a surrogate measure for the stability of that protein. Following their purification, Differential Scanning Fluorimetry (DSF) was used to measure the Tm of a selection of the above $V_H$ clones. Many of the human cDNA-derived $V_H$ could not be tested due to their exceptionally poor production yields and as such, the mean Tm value for this population of clones is likely to represent a best-case scenario. Briefly, this technique relies on detecting fluorescence from a reporter dye that emits signal upon successful binding to exposed hydrophobic residues. Thus, as a protein is heated and unfolds, the reporter dye is able to bind and fluorescence can be detected. The results depicted in FIG. 31 were generated using the Protein Thermal Shift Kit (Applied Biosytems, cat no 4461146) and analysis carried out using Protein Thermal Shift software (Cat. no. 4466037). The Tm values derived from the Boltzmann fit are reported (FIG. 31) and it is evident that the population of $V_H$ isolated from the transgenic mouse gave a significantly higher Tm compared to those that were isolated from human cDNA (57.9° C. for transgenic mouse-derived $V_H$ compared to 54.1° C. for $V_H$ cloned from human source). It should be noted that these data are from naïve mice and represent $V_H$ that are largely of germline sequence and have not undergone affinity maturation. Following immunisation, antigen-specific, affinity-matured $V_H$ frequently exhibit significantly elevated Tm compared to those shown here.

The $V_H$ from the immunised mice do not exhibit a propensity for aggregation (see FIG. 32). HPLC size exclusion analyses of purified $V_H$ was performed. Briefly, $V_H$ solutions were analysed using a Waters 2795 Separation Module on a TSK gel G2000SWXL (TOSOH) column with detection at 280 nM, using a mobile phase of 10% isoproponal, 90% PBS or 100 mM phosphate buffer pH6.8, 150 mM NaCl and a flow rate of 0.5-0.7 ml/min. For some $V_H$ preparations, the particular *E. coli* strain used permitted read-through into the gene III sequence within the phagemid vector and a small amount of $V_H$-gene III fusion product is apparent. However, negligible amounts dimeric or aggregated $V_H$ are found.

Overall, these experiments demonstrate that human $V_H$ that are derived from the transgenic mouse have enhanced solubility and stability compared to those that have developed in association with a rearranged partner light chain.

REFERENCES

Bébin A G, Carrion C, Marquet M, Cogné N, Lecardeur S, Cogné M, Pinaud E (2010). In vivo redundant function of the 3' IgH regulatory element HS3b in the mouse. J Immunol. 184:3710-7.

Brownstein B H, Silverman G A, Little R D, Burke D T, Korsmeyer S J, Schlessinger D, Olson M V (1989), Isolation of single-copy human genes from a library of yeast artificial chromosome clones. Science, 244:1348-51.

Chatterjee S, Ju Z, Hassan R, Volpi S A, Emelyanov A V, Birshtein B K (2011). Dynamic changes in binding of immunoglobulin heavy chain 3' regulatory region to protein factors during class switching. J Biol Chem. 286: 29303-12.

Cogné M, Lansford R, Bottaro A, Zhang J, Gorman J, Young F, Cheng H L, Alt F W (1994). A class switch control region at the 3' end of the immunoglobulin heavy chain locus. Cell. 1994 77:737-47.

Davies N P, Rosewell I R, Bruggemann M (1992). Targeted alterations in yeast artificial chromosomes for inter-species gene transfer. Nucleic Acids Res. 20:2693-8.

Garrett F E, Emelyanov A V, Sepulveda M A, Flanagan P, Volpi S, Li F, Loukinov D, Eckhardt L A, Lobanenkov V V, Birshtein B K (2005). Chromatin architecture near a potential 3' end of the Igh locus involves modular regulation of histone modifications during B-Cell development and in vivo occupancy at CTCF sites. Mol Cell Biol. 25:1511-25.

Gibson D G, Benders G A, Axelrod K C, Zaveri J, Algire M A, Moodie M, Montague M G, Venter J C, Smith H O, Hutchison C A 3$^{rd}$ (2008). One-step assembly in yeast of 25 overlapping DNA fragments to form a complete synthetic *Mycoplasma genitalium* genome. Proc Natl Acad Sci USA. 105:20404-9.

Hamer L, Johnston M, Green E D (1995). Isolation of yeast artificial chromosomes free of endogenous yeast chromosomes: construction of alternate hosts with defined karyotypic alterations. Proc Natl Acad Sci USA. 92:11706-10.

Lieberson R, Ong J, Shi X, Eckhardt L A (1995). Immunoglobulin gene transcription ceases upon deletion of a distant enhancer. EMBO J. 14:6229-38.

Manis J P, van der Stoep N, Tian M, Ferrini R, Davidson L, Bottaro A and Alt F W (1998). Class switching in B cells lacking 3' immunoglobulin heavy chain enhancers. J. Exp. Med. 188, 1421-1431

Markie D (2006). Markers, selection, and media in yeast artificial chromosome cloning. Methods Mol Biol. 349: 1-12.

Neuberger M S (1983). Expression and regulation of immunoglobulin heavy chain gene transfected into lymphoid cells. EMBO J. 2:1373-8.

Pettersson S, Cook G P, Bruggemann M, Williams G T, Neuberger M S (1990). A second B cell-specific enhancer 3' of the immunoglobulin heavy-chain locus. Nature. 344:165-8.

Sanchez C P and Lanzer M (2006). Construction of yeast artificial chromosome libraries from pathogens and nonmodel organisms. YAC protocols, 2$^{nd}$. Methods in Molecular Biology. Vol 349, 13-26.

Tosato V, Waghmare S K, Bruschi C V (2005). Non-reciprocal chromosomal bridge-induced translocation (BIT) by targeted DNA integration in yeast. Chromosoma. 114(1):15-27.

Vincent-Fabert C, Fiancette R, Pinaud E, Truffinet V, Cogné N, Cogné M, Denizot Y (2010). Genomic deletion of the whole IgH 3' regulatory region (hs3a, hs1,2, hs3b, and hs4) dramatically affects class switch recombination and Ig secretion to all isotypes. Blood. 116:1895-8.

Vincent-Fabert C, Truffinet V, Fiancette R, Cogné N, Cogné M, Denizot Y(2009). Ig synthesis and class switching do not require the presence of the hs4 enhancer in the 3' IgH regulatory region. J Immunol. 182:6926-32.

Zhang B, Alaie-Petrillo A, Kon M, Li F, Eckhardt L A (2007). Transcription of a productively rearranged Ig VDJC alpha does not require the presence of HS4 in the IgH 3' regulatory region. J Immunol. 178:6297-306.

The invention claimed is:

1. A transgenic mouse comprising in its genome a vector comprising:
   a) at least 10 functional human heavy chain V genes wherein at least 10 functional human heavy chain V genes are in their natural configuration;
   b) at least one human heavy chain D gene and at least one human heavy chain J gene;
   c) a murine μ enhancer;
   d) a murine switch μ element;
   e) a murine C gene which lacks the CH1 exon, wherein the C gene consists of a C gene selected from Cγ1, Cγ2b and/or Cγ2a; and
   f) a murine 3' enhancer region,
   wherein Cμ is absent in the mouse, or Cμ is partially absent to the extent that it is non-functional, and
   wherein the transgenic mouse is capable of expressing a chimeric immunoglobulin heavy chain encoded by the vector in response to antigen challenge.

2. A transgenic mouse according to claim 1 wherein said mouse comprises a disruption in one or more endogenous immunoglobulin loci, wherein the disruption renders the one or more endogenous immunoglobulin loci non-functional.

3. A transgenic mouse according to claim 2 wherein said mouse comprises a non-functional endogenous lambda light chain locus and/or a non-functional endogenous kappa light chain locus and/or a non-functional endogenous heavy chain locus.

4. A method for making an in vitro display library comprising the step of using a transgenic mouse according to claim 1 to produce an in vitro display library.

5. A method according to claim 4 wherein said library is a naïve library.

6. A method for making a library comprising the step of immunisation of a transgenic mouse according to claim 1.

7. A method according to claim 4, comprising the steps of;
   a) isolating a cell or tissue expressing a heavy chain antibody (HCAb),
   b) cloning the sequence encoding the $V_H$ domain from mRNA derived from the isolated cell or tissue,
   c) constructing a library from cloned transcripts, and
   d) isolating the $V_H$ domain.

8. A method according to claim 7, wherein the method comprises using next generation sequencing to construct the library of cloned transcripts.

9. A method according to claim 6, comprising the steps of;
   a) isolating a cell or tissue expressing a heavy chain antibody (HCAb),
   b) cloning the sequence encoding the $V_H$ domain from mRNA derived from the isolated cell or tissue,
   c) constructing a library from cloned transcripts, and
   d) isolating the $V_H$ domain.

10. A method according to claim 9, wherein the method comprises using next generation sequencing to construct the library of cloned transcripts.

11. The transgenic mouse according to claim 2, wherein the disruption is a partial deletion, a complete deletion, or an insertion.

* * * * *

SEQUENCE LISTING

```
<160> NUMBER OF SEQ ID NOS: 151

<210> SEQ ID NO 1
<211> LENGTH: 88
<212> TYPE: DNA
<213> ORGANISM: Artificial Sequence
<220> FEATURE:
<223> OTHER INFORMATION: Primer

<400> SEQUENCE: 1
gacattctgc cattgtgatt actactacta ctacggtatg gacgtctggg ggcaagggac      60
cacggtcacc gtctcctcag gtaagaat                                        88

<210> SEQ ID NO 2
<211> LENGTH: 31
<212> TYPE: DNA
<213> ORGANISM: Artificial Sequence
<220> FEATURE:
```

<223> OTHER INFORMATION: Primer

<400> SEQUENCE: 2
ttgaggacca gagagggata aaagagaaat g                                    31

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
agaggacgta tagggaggag gggttc                                          26

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
aacaccttca gcgatgcaga c                                               21

<210> SEQ ID NO 5
<211> LENGTH: 546
<212> TYPE: DNA
<213> ORGANISM: Artificial Sequence
<220> FEATURE:
<223> OTHER INFORMATION: Primer

<400> SEQUENCE: 5
tcatgcccct agagttggct gaagggccag atccacctac tctagaggca tctctccctg     60
tctgtgaagg cttccaaagt cacgttcctg tggctagaag cagctccat agccctgctg    120 cagtttcgtc ctgtatacca ggttcaccta ctaccatatc tagccctgcc tgccttaaga   180
gtagcaacaa ggaaatagca gggtgtagag ggatctcctg tctgacagga ggcaagaaga   240
cagattctta cccctccatt tctctttttat ccctctctgg tcctcagaag aggacgtata   300
gggaggaggg gttcactaga ggtgaggctc aagccattag cctgcctaaa ccaaccaggc   360
tggacagcca tcaccaggaa atggatctca gcccagaaga tcgaaagttg ttcttctccc   420
ttctggagat ttctatgtcc tttacactca ttggttaata tcctgggttg gattcccaca   480
catcttgaca aacagagaca attgagtatc accagccaaa agtcataccc aaaaacagcc   540
tggcat                                                              546

<210> SEQ ID NO 6
<211> LENGTH: 57
<212> TYPE: DNA
<213> ORGANISM: Artificial Sequence
<220> FEATURE:
<223> OTHER INFORMATION: Primer

<400> SEQUENCE: 6
gaacccctcc tccctatacg tcctctttga ggaccagaga gggataaaag agaaatg       57

<210> SEQ ID NO 7
<211> LENGTH: 26
<212> TYPE: DNA
<213> ORGANISM: Artificial Sequence
<220> FEATURE:
<223> OTHER INFORMATION: Primer

```
<400> SEQUENCE: 7
agaggacgta tagggaggag gggttc                                          26

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
atgccaggct gtttttgggt a                                               21

<210> SEQ ID NO 9
<211> LENGTH: 80
<212> TYPE: DNA
<213> ORGANISM: Artificial Sequence
<220> FEATURE:
<223> OTHER INFORMATION: Primer

<400> SEQUENCE: 9
tacatctttt ttcctctctg tctgcatcgc tgaaggtgtt tcgtcgccgc acttatgact     60
gtcttcttta tcatgcaact                                                 80

<210> SEQ ID NO 10
<211> LENGTH: 626
<212> TYPE: DNA
<213> ORGANISM: Artificial Sequence
<220> FEATURE:
<223> OTHER INFORMATION: Primer

<400> SEQUENCE: 10
acggctcagg aggaaaaggc actctgtgtg gagctcttca gtgggtatga atggtgatg      60 gagaagccca ggtgcactga aaatccagga gctgaatttg atcaccagga cgcatatggt   120
agagaggaaa atgaattgat tcccaaatgt tctcctctat gtgtgcaccg tggcatgtgc   180
atgcacacaa ttacacataa acacattcaa cataaataca acacacatat acacgctgca   240
cacacataca cacacagaac acacaccaca cacacacacc acacacaatc acacacatat   300
tccacacagt acaccacaaa catctataca caccacacac acagacacac acacacacac   360
acattcatac acagcacaac acaaacatct atacacaaca cacacacaat acacatagtc   420
acacgcatat tcactcacac acatattcac ccacacacaa tcatacatag acacattcaa   480
cataaacaca acaccacaca cacacacact tgcacacaca aatgtaatga tttttttaag   540
gactacatct ttttttcctct ctgtctgcat cgctgaaggt gttcaattgc caaaatcaca   600
ggtgagccca gatgcatacc cgggac                                        626

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
acggctcagg aggaaaaggc ac                                              22

<210> SEQ ID NO 12
<211> LENGTH: 43
<212> TYPE: DNA
```

```
<213> ORGANISM: Artificial Sequence
<220> FEATURE:
<223> OTHER INFORMATION: Primer

<400> SEQUENCE: 12
tcacctgtga ttttggcaat tgaacacctt cagcgatgca gac         43

<210> SEQ ID NO 13
<211> LENGTH: 43
<212> TYPE: DNA
<213> ORGANISM: Artificial Sequence
<220> FEATURE:
<223> OTHER INFORMATION: Primer

<400> SEQUENCE: 13
gtcccgggta tgcatctggg ctcacctgtg attttggcaa ttg         43

<210> SEQ ID NO 14
<211> LENGTH: 766
<212> TYPE: DNA
<213> ORGANISM: Artificial Sequence
<220> FEATURE:
<223> OTHER INFORMATION: Primer

<400> SEQUENCE: 14
gaggtacagg gggctcatgg gtttataagt tcaggtttat accaaggttt cgggggtag      60 cctgaggctc atgtaccttc ttgtggtagc cccaggttc tgtgcatggt actgctcagt     120
tactggcatg gcttctggga aggctgggct cccacgtccc ctgtggacac atggttacgc    180
caagaacaga actacaaagt taggagttac cattcccacc tgcacctgta tctccagtac    240
ctgggtttct aagacgtagt gagtcctctt gccaaccagg gtctgccaca atggtcaggc    300
acagctgtgg gccggtcagc cccatcaggt cacaccagca ggtcccagga gcacagagct    360
taaatgcccc ctagtgtccc tagtgaggct ccggtgcccg tcagtgggca gagcgcacat    420
cgcccacagt ccccgagaag ttgggggggag gggtcggcaa ttgaaccggt gcctagagaa    480
ggtggcgcgg ggtaaactgg gaaagtgatg tcgtgtactg gctccgcctt tttcccgagg    540
gtgggggaga accgtatata agtgcagtag tcgccgtgaa cgttcttttt cgcaacgggt    600
ttgccgccag aacacaggta agtgccgtgt gtggttcccg cgggcctggc ctctttacgg    660
gttatggccc ttgcgtgcct tgaattactt ccacctggct gcagtacgtg attcttgatc    720
ccgagcttcg ggttggaagt gggtgggaga gttcgaggcc ttgcgc                   766

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
gaggtacagg gggctcatgg gt                              22

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
agcctcacta gggacactag ggggcattta agc                  33
```

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
ccctagtgtc cctagtgagg ctccggtgcc cgt                                    33

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gcgcaaggcc tcgaactctc                                                   20

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
ggttggattc tatcttcgca tgg                                               23

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
tgggtcctgt ctttctacct ttg                                               23

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
gctccttgct gggtcttaat gtt                                               23

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
ttagaaccgt gtcttctaca attga                                             25

<210> SEQ ID NO 23
<211> LENGTH: 20
<212> TYPE: DNA
<213> ORGANISM: Artificial Sequence
<220> FEATURE:

-continued

```
<223> OTHER INFORMATION: Primer

<400> SEQUENCE: 23
gggtaggagg ttgttggtta                                                20

<210> SEQ ID NO 24
<211> LENGTH: 34
<212> TYPE: DNA
<213> ORGANISM: Artificial Sequence
<220> FEATURE:
<223> OTHER INFORMATION: Primer

<400> SEQUENCE: 24
cccgctgggc tctgcaagag aggagaatgt gtga                                34

<210> SEQ ID NO 25
<211> LENGTH: 31
<212> TYPE: DNA
<213> ORGANISM: Artificial Sequence
<220> FEATURE:
<223> OTHER INFORMATION: Primer

<400> SEQUENCE: 25
ctctcttgca gagcccagcg ggcccatttc a                                   31

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
gcttgttttt atatcgagct tgc                                            23

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
tcagtctcac ttgcctggtc gt                                             22

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
ctttgtagca catgcgtcat cc                                             22

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
tgaaggcatg aaggagttga gc                                             22
```

```
<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
acaaccccct atcctacaca tt                                              22

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
gggtcctggc aacattagcg                                                 20

<210> SEQ ID NO 32
<211> LENGTH: 34
<212> TYPE: DNA
<213> ORGANISM: Artificial Sequence
<220> FEATURE:
<223> OTHER INFORMATION: Primer

<400> SEQUENCE: 32
cactctgggc tctgcaagaa aggaggatgt gtga                                 34

<210> SEQ ID NO 33
<211> LENGTH: 32
<212> TYPE: DNA
<213> ORGANISM: Artificial Sequence
<220> FEATURE:
<223> OTHER INFORMATION: Primer

<400> SEQUENCE: 33
ctttcttgca gagcccagag tgcccataac ac                                   32

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
tggtgttcag caggctaatt tg                                              22

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
caggccccac ttctttacct aa                                              22

<210> SEQ ID NO 36
<211> LENGTH: 25
<212> TYPE: DNA
<213> ORGANISM: Artificial Sequence
<220> FEATURE:
<223> OTHER INFORMATION: Primer
```

<400> SEQUENCE: 36
ttgttagttc atcacagggc aattc                                        25

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
agagccccct gtctgataag aatctgg                                      27

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
gagtccccat ccccaaggct gg                                           22

<210> SEQ ID NO 39
<211> LENGTH: 32
<212> TYPE: DNA
<213> ORGANISM: Artificial Sequence
<220> FEATURE:
<223> OTHER INFORMATION: Primer

<400> SEQUENCE: 39
gatggtgaag gttaggatgt ctgtggaggg ac                                32

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
ccatcttccc accatccagt gagc                                         24

<210> SEQ ID NO 41
<211> LENGTH: 24
<212> TYPE: DNA
<213> ORGANISM: Artificial Sequence
<220> FEATURE:
<223> OTHER INFORMATION: Primer

<400> SEQUENCE: 41
gcaacagtgg taggtcgctt gtgg                                         24

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
ggagatcagg aatgagggac aaac                                         24

<210> SEQ ID NO 43
<211> LENGTH: 21

<212> TYPE: DNA
<213> ORGANISM: Artificial Sequence
<220> FEATURE:
<223> OTHER INFORMATION: Primer

<400> SEQUENCE: 43
gcctttccca tgctcttgct g                                      21

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
ggcaggaaag aagggttaag at                                     22

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
gagggagcac caatgagaag                                        20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
cagatgaggg gaatgcaaat                                        20

<210> SEQ ID NO 47
<211> LENGTH: 30
<212> TYPE: DNA
<213> ORGANISM: Artificial Sequence
<220> FEATURE:
<223> OTHER INFORMATION: Primer

<400> SEQUENCE: 47
cccaagcttg gtgcctctga tcccagggct                             30

<210> SEQ ID NO 48
<211> LENGTH: 27
<212> TYPE: DNA
<213> ORGANISM: Artificial Sequence
<220> FEATURE:
<223> OTHER INFORMATION: Primer

<400> SEQUENCE: 48
gctctagatc tgggctcaca ctcacct                                27

<210> SEQ ID NO 49
<211> LENGTH: 30
<212> TYPE: DNA
<213> ORGANISM: Artificial Sequence
<220> FEATURE:
<223> OTHER INFORMATION: Primer

<400> SEQUENCE: 49
cccaagcttg aagccagtca aggggggcttc                                    30

<210> SEQ ID NO 50
<211> LENGTH: 27
<212> TYPE: DNA
<213> ORGANISM: Artificial Sequence
<220> FEATURE:
<223> OTHER INFORMATION: Primer

<400> SEQUENCE: 50
gctctagagg ggttttcaca ctgtgtc                                        27

<210> SEQ ID NO 51
<211> LENGTH: 30
<212> TYPE: DNA
<213> ORGANISM: Artificial Sequence
<220> FEATURE:
<223> OTHER INFORMATION: Primer

<400> SEQUENCE: 51
cccaagcttg agtccagtcc agggagatct                                     30

<210> SEQ ID NO 52
<211> LENGTH: 27
<212> TYPE: DNA
<213> ORGANISM: Artificial Sequence
<220> FEATURE:
<223> OTHER INFORMATION: Primer

<400> SEQUENCE: 52
gctctagagg ggttttcaca ctgtgtc                                        27

<210> SEQ ID NO 53
<211> LENGTH: 28
<212> TYPE: DNA
<213> ORGANISM: Artificial Sequence
<220> FEATURE:
<223> OTHER INFORMATION: Primer

<400> SEQUENCE: 53
cccaagcttt cacagcagca ttcacaga                                       28

<210> SEQ ID NO 54
<211> LENGTH: 26
<212> TYPE: DNA
<213> ORGANISM: Artificial Sequence
<220> FEATURE:
<223> OTHER INFORMATION: Primer

<400> SEQUENCE: 54
ggaattcctg acttcccctc actgtg                                         26

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
ggggctggag ggagtaatag                                                20

<210> SEQ ID NO 56
<211> LENGTH: 20
<212> TYPE: DNA
<213> ORGANISM: Artificial Sequence

```
<220> FEATURE:
<223> OTHER INFORMATION: Primer

<400> SEQUENCE: 56
acttagctcg gaccacagga                                                   20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
atgatggagt ttgggctgag                                                   20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
ggaaatcagc cttcatctgc                                                   20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
gggtactgcc ttctcgtcag                                                   20

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
atttgcagat aggcgatgct                                                   20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
ccacgctggt cagttttgta                                                   20

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
gctgggaata ggggactctc                                                   20
```

```
<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
ggggtgagac acctgaagaa                                                   20

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
gagtgcagga aaatcatcca                                                   20

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
gcacaggttt gtggcattta                                                   20

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
tgcagcggta ggttttcttt                                                   20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
gcccttcaca gagtccacat                                                   20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
actccaaggc ctttccactt                                                   20

<210> SEQ ID NO 69
<211> LENGTH: 20
<212> TYPE: DNA
<213> ORGANISM: Artificial Sequence
<220> FEATURE:
<223> OTHER INFORMATION: Primer
```

<400> SEQUENCE: 69
atctcttccc ctgcacttcc                                               20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
ctaccaaacg acccagcaat                                               20

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
ccatcctcag caacatctga                                               20

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
gcatgaaagg tcctgctacc                                               20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
gggtggagag accagtgtgt                                               20

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
ttaggtgctg ggagctcatt                                               20

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
aggaccatgg acaagagtgc                                               20

<210> SEQ ID NO 76

```
<211> LENGTH: 20
<212> TYPE: DNA
<213> ORGANISM: Artificial Sequence
<220> FEATURE:
<223> OTHER INFORMATION: Primer

<400> SEQUENCE: 76
ttggaaggat gggctgtatc                                                      20

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
gggagaatcc cctagagcac                                                      20

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
gtggatgtcg atgcaaaatg                                                      20

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
agctccatgt aggctgtgct                                                      20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
atggactgga cctggaggat                                                      20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
ggagttcttg gcgttgtctc                                                      20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
```
aggactcacc atggagttgg                                                20

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
ctcaggctgt tcatttgcag                                                20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
gagctgggtt ttccttgttg                                                20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
ggcattttct ctggagatgg                                                20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
aggactcacc atggagttgg                                                20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
gagtcatcag ggtcggtgtc                                                20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
acgaccaccg tgagaaaaac                                                20

<210> SEQ ID NO 89
<211> LENGTH: 20
<212> TYPE: DNA

```
<213> ORGANISM: Artificial Sequence
<220> FEATURE:
<223> OTHER INFORMATION: Primer

<400> SEQUENCE: 89
gctggtgggt gtgatgtatg                                           20

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
cttcccttga ccgaagacag                                           20

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
ctgtggtagc caccataccc                                           20

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
tgggtaggga catagggaca                                           20

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
gctcttgtgc tcctggagag                                           20

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
aaaaggtatc cccaccttgc                                           20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
ggggagcatg gttttgtag                                            20
```

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
ctgctgctgg gaaaacaagt                    20

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
gcaggagaga ggttgtgagg                    20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
gctttccttc tgcctccttt                    20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
cctggtttgt tcaggcatct                    20

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
cggagacaga aggtctctgg                    20

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
agccttttca gtttcggtca                    20

<210> SEQ ID NO 102
<211> LENGTH: 21
<212> TYPE: DNA
<213> ORGANISM: Artificial Sequence
<220> FEATURE:

<223> OTHER INFORMATION: Primer

<400> SEQUENCE: 102
ctggtttcca agagaaaagg a                                             21

<210> SEQ ID NO 103
<211> LENGTH: 24
<212> TYPE: DNA
<213> ORGANISM: Artificial Sequence
<220> FEATURE:
<223> OTHER INFORMATION: Primer

<400> SEQUENCE: 103
caagtgtaca gtccccgaag caag                                          24

<210> SEQ ID NO 104
<211> LENGTH: 22
<212> TYPE: DNA
<213> ORGANISM: Artificial Sequence
<220> FEATURE:
<223> OTHER INFORMATION: Primer

<400> SEQUENCE: 104
tgatacacgc aacacgcttg tc                                            22

<210> SEQ ID NO 105
<211> LENGTH: 22
<212> TYPE: DNA
<213> ORGANISM: Artificial Sequence
<220> FEATURE:
<223> OTHER INFORMATION: Primer

<400> SEQUENCE: 105
gaggtacagg gggctcatgg gt                                            22

<210> SEQ ID NO 106
<211> LENGTH: 25
<212> TYPE: DNA
<213> ORGANISM: Artificial Sequence
<220> FEATURE:
<223> OTHER INFORMATION: Primer

<400> SEQUENCE: 106
cttggcccgc atttacaaga ctatc                                         25

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
cgtgcgtgga gtaaaaaggt                                               20

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
tgaacgcact ctcactacgg                                               20

```
<210> SEQ ID NO 109
<211> LENGTH: 26
<212> TYPE: DNA
<213> ORGANISM: Artificial Sequence
<220> FEATURE:
<223> OTHER INFORMATION: Primer

<400> SEQUENCE: 109
gcccaataga aagagaacaa ttgacc                                          26

<210> SEQ ID NO 110
<211> LENGTH: 23
<212> TYPE: DNA
<213> ORGANISM: Artificial Sequence
<220> FEATURE:
<223> OTHER INFORMATION: Primer

<400> SEQUENCE: 110
acacctccgc ttacatcaac acc                                             23

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
ggatcacgag gtcaggagat                                                 20

<210> SEQ ID NO 112
<211> LENGTH: 19
<212> TYPE: DNA
<213> ORGANISM: Artificial Sequence
<220> FEATURE:
<223> OTHER INFORMATION: Primer

<400> SEQUENCE: 112
acggagtctc gctctgtcg                                                  19

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
gacctcggga tcatccttgc                                                 20

<210> SEQ ID NO 114
<211> LENGTH: 17
<212> TYPE: DNA
<213> ORGANISM: Artificial Sequence
<220> FEATURE:
<223> OTHER INFORMATION: Primer

<400> SEQUENCE: 114
atggactgga cctggag                                                    17

<210> SEQ ID NO 115
<211> LENGTH: 22
<212> TYPE: DNA
<213> ORGANISM: Artificial Sequence
<220> FEATURE:
<223> OTHER INFORMATION: Primer
```

<400> SEQUENCE: 115
atggacacac tttgctccac gc                                    22

<210> SEQ ID NO 116
<211> LENGTH: 21
<212> TYPE: DNA
<213> ORGANISM: Artificial Sequence
<220> FEATURE:
<223> OTHER INFORMATION: Primer

<400> SEQUENCE: 116
atgaaacacc tgtggttctt c                                     21

<210> SEQ ID NO 117
<211> LENGTH: 21
<212> TYPE: DNA
<213> ORGANISM: Artificial Sequence
<220> FEATURE:
<223> OTHER INFORMATION: Primer

<400> SEQUENCE: 117
atgtctgtct ccttcctcat c                                     21

<210> SEQ ID NO 118
<211> LENGTH: 20
<212> TYPE: DNA
<213> ORGANISM: Artificial Sequence
<220> FEATURE:
<223> OTHER INFORMATION: Primer

<400> SEQUENCE: 118
atggarttkg grctgagctg                                       20

<210> SEQ ID NO 119
<211> LENGTH: 18
<212> TYPE: DNA
<213> ORGANISM: Artificial Sequence
<220> FEATURE:
<223> OTHER INFORMATION: Primer

<400> SEQUENCE: 119
gtcaggatgt gggttttc                                         18

<210> SEQ ID NO 120
<211> LENGTH: 21
<212> TYPE: DNA
<213> ORGANISM: Artificial Sequence
<220> FEATURE:
<223> OTHER INFORMATION: Primer

<400> SEQUENCE: 120
ggaggtgccc tgggctgtgt c                                     21

<210> SEQ ID NO 121
<211> LENGTH: 18
<212> TYPE: DNA
<213> ORGANISM: Artificial Sequence
<220> FEATURE:
<223> OTHER INFORMATION: Primer

<400> SEQUENCE: 121
gtgtctgggc acacactc                                         18

<210> SEQ ID NO 122
<211> LENGTH: 19

```
<212> TYPE: DNA
<213> ORGANISM: Artificial Sequence
<220> FEATURE:
<223> OTHER INFORMATION: Primer

<400> SEQUENCE: 122
ctcacactga cttcccctc                                                   19

<210> SEQ ID NO 123
<211> LENGTH: 50
<212> TYPE: DNA
<213> ORGANISM: Artificial Sequence
<220> FEATURE:
<223> OTHER INFORMATION: Primer

<400> SEQUENCE: 123
ggaacagacc accatggccc aggtbcagct ggtgcagtct ggggctgagg                 50

<210> SEQ ID NO 124
<211> LENGTH: 42
<212> TYPE: DNA
<213> ORGANISM: Artificial Sequence
<220> FEATURE:
<223> OTHER INFORMATION: Primer

<400> SEQUENCE: 124
ggaacagacc accatggccc aggtbcagct ggtgcagtct gg                         42

<210> SEQ ID NO 125
<211> LENGTH: 73
<212> TYPE: DNA
<213> ORGANISM: Artificial Sequence
<220> FEATURE:
<223> OTHER INFORMATION: Primer

<400> SEQUENCE: 125
gccgctggat tgttattact cgcggcccag ccggccatgg cccaggtgca gctggtgcag     60
tctggggctg agg                                                        73

<210> SEQ ID NO 126
<211> LENGTH: 73
<212> TYPE: DNA
<213> ORGANISM: Artificial Sequence
<220> FEATURE:
<223> OTHER INFORMATION: Primer

<400> SEQUENCE: 126
gccgctggat tgttattact cgcggcccag ccggccatgg cccaggtcca gctcgtgcag     60
tctggggctg agg                                                        73

<210> SEQ ID NO 127
<211> LENGTH: 73
<212> TYPE: DNA
<213> ORGANISM: Artificial Sequence
<220> FEATURE:
<223> OTHER INFORMATION: Primer

<400> SEQUENCE: 127
gccgctggat tgttattact cgcggcccag ccggccatgg cccaggttca gctggtgcag     60
tctggagctg agg                                                        73

<210> SEQ ID NO 128
<211> LENGTH: 73
<212> TYPE: DNA
```

```
<213> ORGANISM: Artificial Sequence
<220> FEATURE:
<223> OTHER INFORMATION: Primer

<400> SEQUENCE: 128
gccgctggat tgttattact cgcggcccag ccggccatgg cccaggtcca gctggtacag      60
tctggggctg agg                                                        73

<210> SEQ ID NO 129
<211> LENGTH: 65
<212> TYPE: DNA
<213> ORGANISM: Artificial Sequence
<220> FEATURE:
<223> OTHER INFORMATION: Primer

<400> SEQUENCE: 129
gccgctggat tgttattact cgcggcccag ccggccatgg cccagrtcac cttgaaggag      60
tctgg                                                                 65

<210> SEQ ID NO 130
<211> LENGTH: 42
<212> TYPE: DNA
<213> ORGANISM: Artificial Sequence
<220> FEATURE:
<223> OTHER INFORMATION: Primer

<400> SEQUENCE: 130
ggaacagacc accatggccc agatcacctt gaaggagtct gg                        42

<210> SEQ ID NO 131
<211> LENGTH: 48
<212> TYPE: DNA
<213> ORGANISM: Artificial Sequence
<220> FEATURE:
<223> OTHER INFORMATION: Primer

<400> SEQUENCE: 131
ggaacagacc accatggccs aggtgcagct ggtggagtct gggggagg                  48

<210> SEQ ID NO 132
<211> LENGTH: 71
<212> TYPE: DNA
<213> ORGANISM: Artificial Sequence
<220> FEATURE:
<223> OTHER INFORMATION: Primer

<400> SEQUENCE: 132
gccgctggat tgttattact cgcggcccag ccggccatgg ccgaggtgca gctggtggag      60
tctgggggag g                                                          71

<210> SEQ ID NO 133
<211> LENGTH: 71
<212> TYPE: DNA
<213> ORGANISM: Artificial Sequence
<220> FEATURE:
<223> OTHER INFORMATION: Primer

<400> SEQUENCE: 133
gccgctggat tgttattact cgcggcccag ccggccatgg ccgaagtgca gctggtggag      60
tctgggggag g                                                          71

<210> SEQ ID NO 134
<211> LENGTH: 71
```

```
<212> TYPE: DNA
<213> ORGANISM: Artificial Sequence
<220> FEATURE:
<223> OTHER INFORMATION: Primer

<400> SEQUENCE: 134
gccgctggat tgttattact cgcggcccag ccggccatgg cccaggtgca gctggtggag    60
tctgggggag g                                                          71

<210> SEQ ID NO 135
<211> LENGTH: 71
<212> TYPE: DNA
<213> ORGANISM: Artificial Sequence
<220> FEATURE:
<223> OTHER INFORMATION: Primer

<400> SEQUENCE: 135
gccgctggat tgttattact cgcggcccag ccggccatgg ccgaggtgca gctgttggag    60
tctgggggag g                                                          71

<210> SEQ ID NO 136
<211> LENGTH: 65
<212> TYPE: DNA
<213> ORGANISM: Artificial Sequence
<220> FEATURE:
<223> OTHER INFORMATION: Primer

<400> SEQUENCE: 136
gccgctggat tgttattact cgcggcccag ccggccatgg cccaggtgca gctgcaggag    60
tcggg                                                                 65

<210> SEQ ID NO 137
<211> LENGTH: 42
<212> TYPE: DNA
<213> ORGANISM: Artificial Sequence
<220> FEATURE:
<223> OTHER INFORMATION: Primer

<400> SEQUENCE: 137
ggaacagacc accatggccc aggtgcagct gcaggagtcg gg                        42

<210> SEQ ID NO 138
<211> LENGTH: 66
<212> TYPE: DNA
<213> ORGANISM: Artificial Sequence
<220> FEATURE:
<223> OTHER INFORMATION: Primer

<400> SEQUENCE: 138
gccgctggat tgttattact cgcggcccag ccggccatgg cccaggtgca gctacagcag    60
tggggc                                                                66

<210> SEQ ID NO 139
<211> LENGTH: 42
<212> TYPE: DNA
<213> ORGANISM: Artificial Sequence
<220> FEATURE:
<223> OTHER INFORMATION: Primer

<400> SEQUENCE: 139
ggaacagacc accatggccc aggtacagct gcagcagtca gg                        42

<210> SEQ ID NO 140
```

```
<211> LENGTH: 65
<212> TYPE: DNA
<213> ORGANISM: Artificial Sequence
<220> FEATURE:
<223> OTHER INFORMATION: Primer

<400> SEQUENCE: 140
gccgctggat tgttattact cgcggcccag ccggccatgg cccaggtaca gctgcagcag      60
tcagg                                                                  65

<210> SEQ ID NO 141
<211> LENGTH: 34
<212> TYPE: DNA
<213> ORGANISM: Artificial Sequence
<220> FEATURE:
<223> OTHER INFORMATION: Primer

<400> SEQUENCE: 141
gctaccgcca ccctcgagtg argagacrgt gacc                                  34

<210> SEQ ID NO 142
<211> LENGTH: 54
<212> TYPE: DNA
<213> ORGANISM: Artificial Sequence
<220> FEATURE:
<223> OTHER INFORMATION: Primer

<400> SEQUENCE: 142
ccgtggtgat ggtggtgatg gctaccgcca ccctcgagtg argagacrgt gacc            54

<210> SEQ ID NO 143
<211> LENGTH: 30
<212> TYPE: PRT
<213> ORGANISM: Homo sapiens
<220> FEATURE:
<221> NAME/KEY: MISC_FEATURE
<223> OTHER INFORMATION: Hypervariable region

<400> SEQUENCE: 143

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 144
<211> LENGTH: 14
<212> TYPE: PRT
<213> ORGANISM: Homo sapiens
<220> FEATURE:
<221> NAME/KEY: MISC_FEATURE
<223> OTHER INFORMATION: Hypervariable region

<400> SEQUENCE: 144

Trp Val Arg Gln Ala Pro Gly Lys Gly Leu Glu Trp Val Ala
1               5                   10

<210> SEQ ID NO 145
<211> LENGTH: 21
<212> TYPE: PRT
<213> ORGANISM: Homo sapiens
<220> FEATURE:
<221> NAME/KEY: MISC_FEATURE
<223> OTHER INFORMATION: Hypervariable region

<400> SEQUENCE: 145

Arg Phe Thr Ile Ser Arg Asp Asn Ala Lys Asn Ser Leu Tyr Leu Gln
```

Met Asn Ser Leu Arg
            20

<210> SEQ ID NO 146
<211> LENGTH: 11
<212> TYPE: PRT
<213> ORGANISM: Homo sapiens
<220> FEATURE:
<221> NAME/KEY: MISC_FEATURE
<223> OTHER INFORMATION: Hypervariable region

<400> SEQUENCE: 146

Ala Glu Asp Thr Ala Leu Tyr Tyr Cys Ala Arg
1               5                   10

<210> SEQ ID NO 147
<211> LENGTH: 11
<212> TYPE: PRT
<213> ORGANISM: Homo sapiens
<220> FEATURE:
<221> NAME/KEY: MISC_FEATURE
<223> OTHER INFORMATION: Hypervariable region

<400> SEQUENCE: 147

Trp Gly Gln Gly Thr Thr Val Thr Val Ser Ser
1               5                   10

<210> SEQ ID NO 148
<211> LENGTH: 98
<212> TYPE: PRT
<213> ORGANISM: Artificial Sequence
<220> FEATURE:
<223> OTHER INFORMATION: VH3 sequence

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 149
<211> LENGTH: 117
<212> TYPE: PRT
<213> ORGANISM: Artificial Sequence
<220> FEATURE:
<223> OTHER INFORMATION: P6C6 sequence

<400> SEQUENCE: 149

Glu Val Gln Leu Val Glu Ser Gly Gly Gly Leu Val Gln Pro Gly Arg
1               5                   10                  15

Ser Leu Arg Leu Ser Cys Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Pro Tyr Ser Tyr Gly Asp Ile Trp Gly Gln Gly Thr Met
                100                 105                 110

Val Thr Val Ser Ser
        115

<210> SEQ ID NO 150
<211> LENGTH: 125
<212> TYPE: PRT
<213> ORGANISM: Artificial Sequence
<220> FEATURE:
<223> OTHER INFORMATION: P6C3 sequence

<400> SEQUENCE: 150

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Gly Thr Gly Thr Thr Gly Phe Tyr Ser Tyr Gly Met
                100                 105                 110

Asp Val Trp Gly Gln Gly Thr Thr Val Thr Val Ser Ser
        115                 120                 125

<210> SEQ ID NO 151
<211> LENGTH: 121
<212> TYPE: PRT
<213> ORGANISM: Artificial Sequence
<220> FEATURE:
<223> OTHER INFORMATION: P6C11 sequence

<400> SEQUENCE: 151

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

```
Ala Arg Asp Met Asp Phe Trp Ser Gly Tyr Tyr Ser Asp Tyr Trp Gly
            100             105             110

Gln Gly Thr Leu Val Thr Val Ser Ser
        115             120
```

UNITED STATES PATENT AND TRADEMARK OFFICE
CERTIFICATE OF CORRECTION

PATENT NO. : 11,547,099 B2
APPLICATION NO. : 15/520627
DATED : January 10, 2023
INVENTOR(S) : Yumin Teng et al.

It is certified that error appears in the above-identified patent and that said Letters Patent is hereby corrected as shown below:

On the Title Page

Item (71):
"(71) Applicant: Crescendo Biologies Limited,
Cambridge (GB)"
Should read:
-- (71) Applicant: Crescendo Biologics Limited,
Cambridge (GB) --

Item (73):
"(73) Assignee: Crescendo Biologies Limited,
Cambridge (GB)"
Should read:
-- (73) Assignee: Crescendo Biologics Limited,
Cambridge (GB) --

Signed and Sealed this
Seventh Day of March, 2023

Katherine Kelly Vidal
*Director of the United States Patent and Trademark Office*